(12) United States Patent
Flatt et al.

(10) Patent No.: US 7,863,298 B2
(45) Date of Patent: Jan. 4, 2011

(54) BRIDGED RING STRUCTURES AS PHARMACEUTICAL AGENTS

(75) Inventors: Brenton T. Flatt, Poway, CA (US); Richard Martin, San Diego, CA (US); Raju Mohan, Encinitas, CA (US); Brett Murphy, Sandy, UT (US)

(73) Assignee: Exelixis, Inc., South San Francisco, CA (US)

( * ) Notice: Subject to any disclaimer, the term of this patent is extended or adjusted under 35 U.S.C. 154(b) by 887 days.

(21) Appl. No.: 10/576,228

(22) PCT Filed: Oct. 13, 2004

(86) PCT No.: PCT/US2004/033666

§ 371 (c)(1),
(2), (4) Date: Feb. 7, 2007

(87) PCT Pub. No.: WO2005/037755

PCT Pub. Date: Apr. 28, 2005

(65) Prior Publication Data

US 2007/0225377 A1      Sep. 27, 2007

Related U.S. Application Data

(60) Provisional application No. 60/511,457, filed on Oct. 14, 2003.

(51) Int. Cl.
*A61K 31/451* (2006.01)
*C07D 211/14* (2006.01)

(52) U.S. Cl. ............................ 514/331; 546/234

(58) Field of Classification Search ............... 514/713, 514/331; 568/47; 546/234
See application file for complete search history.

(56) References Cited

U.S. PATENT DOCUMENTS

| | | | |
|---|---|---|---|
| 4,717,760 | A | 1/1988 | Parker et al. |
| 5,210,353 | A | 5/1993 | Udovich et al. |
| 5,710,347 | A | 1/1998 | Nishibori et al. |
| 6,218,430 | B1 | 4/2001 | Allegretto et al. |
| 2006/0014811 | A1 | 1/2006 | Muto et al. |
| 2006/0035944 | A1 | 2/2006 | Muto et al. |

FOREIGN PATENT DOCUMENTS

| | | |
|---|---|---|
| CA | 1328880 C | 4/1994 |
| EP | 0438715 A2 | 7/1991 |
| EP | 0285160 B1 | 12/1993 |
| GB | 1095959 A | 12/1967 |
| GB | 1 410 275 | 10/1975 |
| JP | 3255067 A | 11/1991 |
| WO | WO 03/103655 | 12/2003 |
| WO | WO 03/103657 | 12/2003 |
| WO | WO 2004/048309 A1 | 6/2004 |
| WO | WO 2004/063345 A2 | 7/2004 |

OTHER PUBLICATIONS

Shimizu, I. et al.; "Molybdenum-Catalyzed Aromatic Substitution With Olefins and Alcohols"; Chemistry Letters 1997; May 2, 1997; pp. 851-852; The Chemical Society of Japan.

Perera et al. "Synthesis and thermal cyclopolymerization of heterocycle containing bis-ortho-diynyl arenes" Tetrahedron, vol. 58, Issue 51, pp. 10197-10203 (2002).

Sengupta et al. "Synthetic studies on tetraphenylmethane dendrimers" Tetrahedron Letters, vol. 40, Issue 51, pp. 9157-9161 (1999).

Pozdnyakovich et al. "Fluorine-containing carbocations. IV. The use of salt solutions of stable polyfluorinated α,α-difluorobenzyl and α-fluorodiphenylmethyl cations in antimony pentafluoride in the synthesis of polyfluorinated benzoic acids, benzophenones and diphenyldifluoromethanes" Journal of Fluorine Chemistry, vol. 4, Issue 3, pp. 317-326 (1974).

Tam-Chang et al. "Catalytic cylcopropanes. Part IX. A thiazolocyclophane as model for pyruvate oxidase and one-pot synthesis of aromatic esters by electrochemical oxidation of aldehydes mediated by bis(coenzyme) catalysis". Helvetica Chimica Acta, 76(7): 2616-2639 (1993).

Hixson et al. "arlycyclopropane photochemistry. Effects of electron-donating and electron-withdrawing aromatic substituents of the photochemical rearrangement of 1,1-diarylcyclopropanes". J. Organic Chem. 53(12): 2706-2711 (1988).

*Primary Examiner*—Taofiq A Solola
(74) *Attorney, Agent, or Firm*—McDonnell Boehnen Hulbert & Berghoff LLP

(57) ABSTRACT

The present invention is directed to 1α,25-dihydroxyvitamin D3 mimics which modulate the vitamin D receptor (VDR). The invention is further directed to pharmaceutical compositions and methods for the treatment, prevention or amelioration of one or more symptoms of disease or disorder related to the activity of the vitamin D receptor using an effective amount of a compound of formula (I).

31 Claims, 2 Drawing Sheets

BRIDGED RING STRUCTURES AS PHARMACEUTICAL AGENTS

FIELD OF THE INVENTION

1α,25-dihydroxyvitamin $D_3$ mimics and their compositions and methods are provided for modulating the activity of receptors and for the treatment, prevention, or amelioration of one or more symptoms of diseases or disorders related to the activity of the vitamin D receptor (VDR).

BACKGROUND OF THE INVENTION

Vitamin D Receptor

The vitamin D receptor (VDR or NR1I1) is a member of the classical endocrine receptor subgroup of the nuclear receptor superfamily, which also includes the retinoic acid receptor, thyroid hormone receptor, estrogen receptor, progesterone receptor, androgen receptor, mineralocorticoid receptor and the glucocorticoid receptor. The vitamin D receptor bears structural and functional similarities to other members of the superfamily, all of which are capable of binding to cis-acting elements in the promoters of their target genes to modulate gene expression in response to specific ligands.

The natural ligand for the vitamin D receptor is the vitamin $D_3$ metabolite, 1α,25-dihydroxyvitamin $D_3$ [1,25-$(OH)_2D_3$]. Vitamin D receptor associated with its ligand forms a heterodimeric complex with the retinoid X receptor (RXR), which binds to a vitamin D specific response element (VDRE) in the regulatory region of target genes to activate gene transcription. The classical target organs of 1α,25-dihydroxyvitamin $D_3$ are the bone, kidney, parathyroid gland and the intestine, where 1α,25-dihydroxyvitamin $D_3$ plays a role in the maintenance of calcium and phosphate homeostasis in the body and bone calcium mobilization and mineralization for bone development.

In addition, 1α,25-dihydroxyvitamin $D_3$ has been discovered to play a role in a diverse range of non-classical physiological functions such as parathyroid hormone synthesis and secretion, differentiation and proliferation of the skin, muscle and reproductive cells, regeneration of neuronal cells and liver cells, regulation of the immune response, secretion of insulin and reproductive organ development.

Many of these non-classical effects of 1α,25-dihydroxyvitamin $D_3$ are believed to be mediated via interaction with a putative membrane receptor which is coupled to signal transduction pathways which produce so-called rapid responses. These include, for example, effects on MAP kinase activation, release of insulin in rat islets, activation of P13 kinases in vascular endothelial cells and the opening of $Ca^{2+}$ and chloride channels.

The discovery of a wide range of physiological actions of 1α,25-dihydroxyvitamin $D_3$ has expanded the therapeutic use of vitamin D modulators to a wide variety of diseases and disorders mediated by, or otherwise affected by the vitamin D receptor or which the vitamin D receptor activity is implicated, including without limitation, hyperproliferative skin diseases, such as psoriasis (including pustulosis palmoplantaris, acrodermatitis continua and nail psoriasis), disturbances of keratinization and keratosis, disorders of sebaceous glands such as, acne, and seborrheic dermatitis, (U.S. Pat. Nos. 4,728,643 and 5,037,816); cancer, including without limitation, breast cancer, (J. NCl 89:212-218, (1997); Lancet 1: 188-191, (1989)); colon, (Lointier et al., Anticancer Res. (7:817-822, (1987), Niendorf, et al., J. Steroid Biochem. 27:815-828 (1987), Tanaka et al., Arch. Biochem. Biophys. 276:415-423 (1990), Halline et al., Endocrinology 134:1710-1717(1994)); prostrate cancer, (Urology 46:365-369 (1994)); brain glial tumours, (Baudet et al., Cancer Lett. 100:3 (1996)); squamous cell carcinoma, (Molecular and Cellular Differentiation 3:31-50, (1995)); ovarian cancer, (U.S. Pat. Nos. 6,444,658, 6,407,082); myeloid leukemia, (Blood 74:82-93 (1989), PNAS USA 80:201-204 (1983), U.S. Pat. No. 4,391,802); osteosarcoma; myelofibrosis; melanoma; diseases of, or imbalances in, the immune system, such as host versus graft and graft versus host reaction and transplant rejection, (U.S. Pat. No. 4,749,710); autoimmune diseases, including without limitation, discoid and systemic lupus erythematosus, type I diabetes mellitus, (Mathieu et al., Diabetologia 37:552-558 (1994), U.S. Pat. No. 5,665,387); multiple sclerosis, (U.S. Pat. No. 6,479,474); chronic dermatoses of auto-immune type, e.g. scleroderma and pemphigus vulgaris, and inflammatory diseases, such as inflammatory bowel disease (U.S. Pat. No. 6,358,939), asthma, (U.S. Pat. No. 6,603,031); rheumatoid arthritis, (U.S. Pat. No. 4,743,596); as well as a number of other disease states including without limitation, cognitive impairment or senile dementia (Alzheimers disease); (U.S. Pat. No. 6,573,255), hyperparathyroidism; (U.S. Pat. No. 6,376,479) and osteoporosis (U.S. Pat. No. 6,150,346).

The therapeutic application of 1α,25-dihydroxyvitamin $D_3$, and its analogs has been traditionally limited due to their hypercalcemic effect, i.e., the effect of elevating serum calcium, which can lead to the severe hypercalcemia leading to death. Previous efforts in the design of synthetic analogs of 1α,25-dihydroxyvitamin $D_3$ have therefore been made to separate the desired properties of 1α,25-dihydroxyvitamin $D_3$ from its calcemic effect, however to date efforts these have met with limited success.

Examples of synthetic 1α,25-dihydroxyvitamin $D_3$ analogs currently approved for use in patients include calcipotriol, (Dovonex®), marketed by Bristol-Meyers Squibb) for the treatment of psoriasis, paricalcitol, (Zemplar®, marketed by Abbott Laboratories), for the treatment of renal failure, doxercalciferol, (Hectorol®, Bone Care Int.) for hyperparathyroidism and 22-oxacalcitriol (also known as maxacalcitol; Chugai Pharmaceuticals). A recent study has shown Zemplar® to be effective in combination with radiation therapy for the treatment of prostate cancer, a non-classical target of 1α,25-dihydroxyvitamin $D_3$ (Dunlap et al., British Journal of Cancer 89:746-753 (2003)).

Other clinical drug candidates include ZK161422 and ZK15202 under development by Schering AG, RO27-2310 and RO23-7553, under development by Hoffman-La Roche and EB1089, under development by Leo Pharmaceuticals. Other 1α,25-dihydroxyvitamin $D_3$ analogs are described in the patent literature.

Although some current analogs of 1α,25-dihydroxyvitamin $D_3$ have shown some degree of separation between their calcium mobilization effect and their beneficial effects, there is an ongoing search for analogs that exhibit even better separation of these activities, particularly for use in treatments that require either acute of chronic dosing.

In one aspect of the current invention, a family of novel 1α,25-dihydroxyvitamin $D_3$ mimics are disclosed. The claimed compounds and compositions include compounds that are shown to be potent in inducing vitamin D receptor activity with reduced hypercalcemic effect. These compounds are potentially suitable for the treatment of diseases and disorders related to the activity of the vitamin D receptor, including without limitation, cancer, sarcoma, myeloma, hyperproliferative skin diseases such as psoriasis, vitamin D-related metabolic diseases such as hyperparathyroidism, chronic kidney disease and osteoporosis, autoimmune diseases such as type I diabetes, rheumatoid arthritis and multiple sclerosis, autoimmune conditions such as transplant rejection and Alzheimer's disease.

SUMMARY OF THE INVENTION

Compounds for use in pharmaceutical compositions and methods for modulating the activity of nuclear receptors are provided. In particular, compounds for use in compositions and methods for modulating the vitamin D receptor, are provided. In certain embodiments, the compounds are bis-aryl derivatives. In one embodiment, the compounds provided herein are agonists of the vitamin D receptor. In another embodiment, the compounds provided herein are antagonists of the vitamin D receptor. In another embodiment, the compounds provided herein are inverse agonists, partial agonists or partial antagonists of the vitamin D receptor. It is to be understood that partial agonists that exhibit low efficacy are, in certain embodiments, antagonists.

The compounds for use in the compositions and methods provided herein have the formula (I):

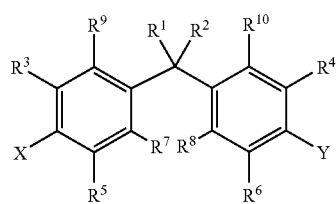

(I)

wherein:

$R^1$ and $R^2$ are each independently halo, haloalkyl, pseudohalo, optionally substituted alkyl, optionally substituted alkenyl, optionally substituted alkynyl, optionally substituted cycloalkyl, optionally substituted heterocyclyl, optionally substituted aryl or optionally substituted heteroaryl; or $R^1$ and $R^2$, together with the carbon atom to which they are attached, form an optionally substituted cycloalkyl consisting of:

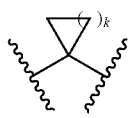

wherein k is an integer from 1 to 6; or $R^1$ and $R^2$, together with the carbon atom to which they are attached, form an optionally substituted heterocyclyl selected from a group consisting of:

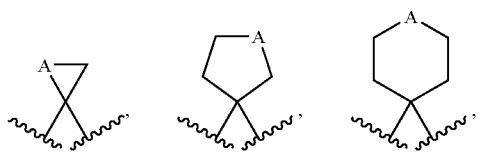

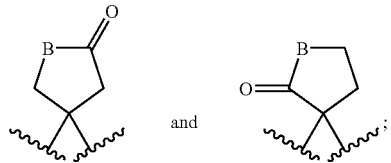

-continued and;

wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$—C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl; and wherein each p is independently 0 to 2;

$R^3$ and $R^4$ are each independently hydrogen, alkyl, alkenyl, alkynyl, cycloalkyl, heterocyclyl, aryl, heteroaryl, halo, pseudohalo, haloalkyl, nitro, cyano, azido, —R$^{14}$—OR$^{15}$, —R$^{14}$—N(R$^{18}$)R$^{19}$, —R$^{14}$—SR$^{15}$, —R$^{14}$—OC(J)R$^{15}$, —R$^{14}$—NR$^{17}$C(J)R$^{15}$, —R$^{14}$—OC(J)N(R$^{18}$)R$^{19}$, —R$^{14}$—NR$^{17}$C(J)N(R$^{18}$)R$^{19}$, —R$^{14}$-NR$^{17}$C(J)OR$^{15}$, —R$^{14}$—C(J)R$^{15}$, —R$^{14}$—C(J)OR$^{15}$, —R$^{14}$—C(J)SR$^{16}$, —R$^{14}$—C(J)N(R$^{18}$)R$^{19}$ or —R$^{14}$C(J)N(R$^{17}$)N(R$^{18}$)R$^{19}$;

$R^5$, $R^6$, $R^7$, $R^8$, $R^9$, $R^{10}$ are each independently hydrogen, halo, hydroxy, amino, pseudohalo, cyano, nitro, alkyl, haloalkyl, alkoxy or haloalkoxy;

X is $R^{25}$;

Y is independently $R^{30}$, —OR$^{31}$, —SR$^{32}$ or —N(R$^{33}$)(R$^{34}$);

$R^{25}$ and $R^{30}$ are each independently selected from (i) or (ii) as follows:

(i) optionally substituted alkyl that may be substituted with one to ten substituents each independently selected from a group consisting of halo, pseudohalo, nitro, cyano, thioxo, azido, amidino, guanidino, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$ and —C(=NR$^{17}$)N(R$^{18}$)R$^{19}$; or (ii) optionally substituted alkenyl or optionally substituted alkynyl, either of which may be substituted with one to ten substituents each independently selected from a group consisting of oxo, thioxo, halo, pseudohalo, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$, —C(=NR$^{17}$)N(R$^{18}$)R$^{19}$, alkyl, haloalkyl, cycloalkyl, heterocyclyl, aryl and heteroaryl;

$R^{31}$, $R^{32}$, $R^{33}$ and $R^{34}$ are each independently optionally substituted alkyl, optionally substituted alkenyl, optionally substituted alkynyl or optionally substituted cycloalkyl; all of which may be optionally substituted with one to ten substituents each independently selected from a group consisting of oxo, halo, pseudohalo, nitro, cyano, azido, amidino, guanidino, —$OR^{15}$, —$OR^{16}OR^{15}$, —$N(R^{18})R^{19}$, —$N(R^{17})N(R^{18})R^{19}$, —$SR^{15}$, —$SR^{16}SR^{15}$, —$S(O)_pR^{20}$, —$N(R^{17})S(O)_pR^{20}$, —$N(R^{17})N(R^{17})S(O)_pR^{20}$, —$OC(J)R^{15}$, —$NR^{17}C(J)R^{15}$, —$OC(J)N(R^{18})R^{19}$, —$NR^{17}C(J)N(R^{18})R^{19}$, —$NR^{17}C(J)OR^{15}$, —$OC(J)OR^{15}$, —$P(R^{21})_2$, —$P(O)(R^{21})_2$, —$OP(O)(R^{21})_2$, —$C(J)R^{15}$, —$C(J)OR^{15}$, —$C(J)SR^{16}$, —$C(J)N(R^{18})R^{19}$, —$C(J)N(R^{17})N(R^{18})R^{19}$, —$C(J)N(R^{17})S(O)_pR^{20}$, —$C(J)N(R^{17})N(R^{17})S(O)_pR^{20}$, —$C(R^{17})=NOR^{15}$, —$C(R^{17})=NR^{17}$, —$C(R^{17})=NN(R^{18})R^{19}$, —$C(=NR^{17})N(R^{18})R^{19}$, alkyl, cycloalkyl, heterocyclyl, aryl and heteroaryl, and $R^{34}$ can additionally be hydrogen;

where each $R^{14}$ is independently a direct bond or alkylene;

where each $R^{15}$ and $R^{17}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, cyano, hydroxy and amino;

where each $R^{16}$ and $R^{20}$ is independently optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino; and where each $R^{18}$ and $R^{19}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino;

or where $R^{18}$ and $R^{19}$, together with the nitrogen atom to which they are attached, form a heterocyclyl or heteroaryl;

each $R^{21}$ is independently alkyl, —$OR^{22}$ or —$N(R^{23})R^{24}$;

$R^{22}$ is hydrogen, alkyl, haloalkyl, alkenyl, alkynyl, cycloalkyl, heterocyclyl, aryl, heteroaryl or aralkyl;

$R^{23}$ and $R^{24}$ are each independently hydrogen, alkyl, haloalkyl, alkenyl, alkynyl or cycloalkyl;

or $R^{23}$ and $R^{24}$, together with the nitrogen atom to which they are attached, form a heterocyclyl or heteroaryl;

each J is independently O or S;

as a single isomer, a mixture of isomers, or as a racemic mixture of isomers; as a solvate or polymorph; or as a prodrug or metabolite; or as a pharmaceutically acceptable salt thereof;

provided that when $R^1$ and $R^2$ form a substituted cyclohexyl, said cyclohexyl, when substituted at the 4-position relative to the gem-diaryl substituents, is substituted with a substituent selected from the group consisting of halo, cyano, optionally substituted alkyl, optionally substituted alkenyl, optionally substituted alkynyl, optionally substituted aryl and optionally substituted heteroaryl; and provided that neither $R^{25}$ nor $R^{30}$ is:

—$CH_2COOH$;
—$CH_2$-5-tetrazolyl;
—$CH_2COOMe$;
—$CH_2COOEt$;
—$CH_2NH(CH_2COOH)$;
—$CH_2N(C(O)Me)(CH_2COOH)$;
—$CH_2$—N-pyrrolidin-2-one;
—$CH_2$-(1-methylpyrrolidin-2-one-3-yl);
—$CH_2COOH$;
—$CH_2C(O)NH_2$;
—$CH_2C(O)NMe_2$;
—$CH_2C(O)NHMe$;
—$CH_2C(O)$—N-pyrrolidine;
—$CH(OH)COOH$;
—$CH(OH)C(O)NH_2$;
—$CH(OH)C(O)NHMe$;
—$CH(OH)C(O)NMe_2$;
—$CH(OH)C(O)NEt_2$;
—$CH_2CH_2COOH$;
—$CH_2CH_2COOMe$;
—$CH_2CH_2COOEt$;
—$CH_2CH_2COOMe$;
—$CH_2CH_2COOEt$;
—$CH_2CH_2C(O)NH_2$;
—$CH_2CH_2C(O)NHMe$;
—$CH_2CH_2C(O)NMe_2$; or
—$CH_2CH_2$-5-tetrazolyl.

DETAILED DESCRIPTION OF THE INVENTION

A. Definitions

Figure 1:
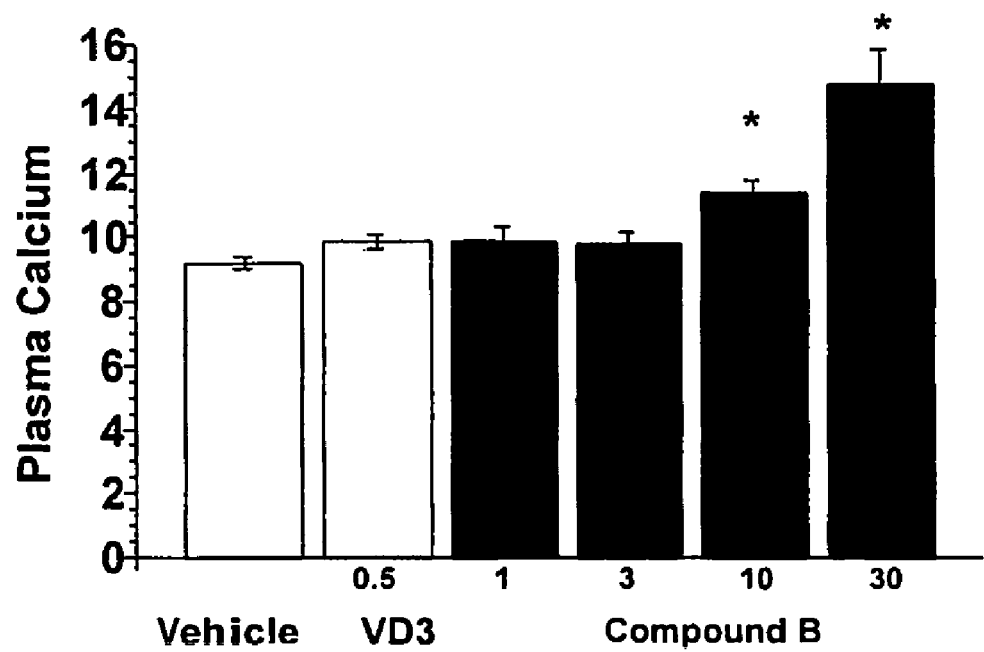
FIG. 1 shows the levels of plasma calcium (mg/dl) at Day 14 in athymic nude mice administered one selected compound of the current invention, Compound B, at four different doses (μg/kg) administered every other day for fourteen days.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, the term "nuclear receptor" refers to a member of a superfamily of regulatory proteins that are receptors for, e.g., steroids, retinoids, vitamin $D_3$ and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, farnesoid X receptor, fatty acids/peroxisome proliferators and ecdysone, that bind to HREs as heterodimers with a common partner, the retinoid X receptor (RXR). Belonging to the latter group is the vitamin D receptor.

As used herein, the term "vitamin D receptor" or "VDR" refers to all mammalian forms of such receptor including, for example, alternative splice isoforms and naturally occurring isoforms (see, e.g. Huber et al, Gene, 290,.:35-43 (2002)). Representative vitamin D receptor species include, without limitation the human (accession NM_005693), rat (accession NP_033530) and mouse (accession AAH06716) forms of the receptor.

As used herein the term, "pharmaceutically acceptable derivatives" refers to salts, esters, enol ethers, enol esters, acetals, ketals, orthoesters, hemiacetals, hemiketals, acids, bases, solvates, hydrates or prodrugs thereof of a compound. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, "treatment" means any manner in which one or more of the symptoms of a disease or disorder are ameliorated or otherwise beneficially altered. Treatment also encompasses any pharmaceutical use of the compositions herein, such as use for treating a nuclear receptor mediated diseases or disorders, or diseases or disorders in which nuclear receptor activity, including vitamin D receptor activity, is implicated.

As used herein, "amelioration of the symptoms" of a particular disorder by administration of a particular compound or pharmaceutical composition refers to any lessening, whether permanent or temporary, that can be attributed to or associated with administration of the composition.

As used herein, "$IC_{50}$" refers to an amount, concentration or dosage of a particular test compound that achieves a 50% inhibition of a maximal response, such as modulation of nuclear receptor, including the vitamin D receptor, activity, in an assay that measures such response.

As used herein, "$EC_{50}$" refers to a dosage, concentration or amount of a particular test compound that elicits a dose-dependent response at 50% of maximral expression of a particular response that is induced, provoked or potentiated by the particular test compound.

As used herein, the term "prodrug" refers to a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

When the compounds described herein contain olefinic double bonds or other centers of geometric asymmetry, and unless specified otherwise, it is intended that the compounds include both E and Z geometric isomers. Likewise, all tautomeric forms are also intended to be included.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−) or (R)- and (S)-isomers may be prepared using chiral synthons or chiral reagents, or resolved using conventional techniques, such as reverse phase HPLC.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkoxy" refers to refers to the radical of the formula —OR wherein R is an alkyl as defined above, e.g. methoxy, ethoxy, n-propoxy, 1-methylethoxy (iso-propoxy), n-butoxy, n-pentoxy, 1,1-dimethylethoxy (t-butoxy), and the like.

As used herein, "alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(O) and S(O)$_2$ groups, or optionally substituted nitrogen atoms, including —NR— and —N$^+$RR-groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "alkynyl" refers to a straight or branched hydrocarbon chain radical consisting solely of carbon and hydrogen atoms, containing at least one triple bond, having from two to eight carbon atoms, and which is attached to the rest of the molecule by a single bond or a triple bond, e.g. ethynyl, pro-1-ynyl, but-1ynyl, pent-1-ynyl, and the like.

As used herein, "amidino" refers to a radical having the formula —C(=NR)N(R')R" where R, R' and R" are each independently hydrogen or alkyl;

As used herein, "amino" refers to —NH$_2$, —NHR or —N(R—)R", where R, R' and R" are alkyl groups.

As used herein, "aralkyl" refers to an alkyl group in which one of the hydrogen atoms of the alkyl is replaced by an aryl group.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "azido" refers to the radical having the formula —N$_3$.

As used herein, "cycloalkyl" refers to a saturated mono- or multi-cyclic ring system, in certain embodiments of 3 to 10 carbon atoms, in other embodiments of 3 to 6 carbon atoms; all of which may optionally be substituted with oxo, thioxo, or exocyclic alkylidene. "Cycloalkenyl" and "cycloalkynyl" refer to mono- or multicyclic ring systems that include at least one double bond and at least one triple bond, respectively.

Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "formamidino" refers to a radical having the formula —C(=NH)NH$_2$.

As used herein, "guanidino" refers to a radical having the formula —N(R)C(=NR')NR"R'" wherein R, R', R" and R'" are each independently hydrogen or alkyl.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "heteroaralkyl" refers to an alkyl group in which one of the hydrogen atoms of the alkyl is replaced by a heteroaryl group.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. Examples of such heterocyclyl radicals include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl; carbazolyl, cinnolinyl, dioxolanyl, dibenzofuranyl, decahydroisoquinolyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thiophenyl, thiamorpholinyl, thiamorpholinyl sulfoxide, and thiamorpholinyl sulfone.

As used herein, "hydrazone" refers to a divalent group such as =NNR$_2$ which is attached to a carbon atom of another group, forming a double bond, wherein R is hydrogen or alkyl.

As used herein, "imide" refers to a cyclic group having the formula RC(=O)N(H)C(=O)R' wherein R and R' are each independently methylene, ethylene or propylene groups that are covalently bonded to form a ring.

As used herein, "imino" refers to a divalent group such as =NR, which is attached to a carbon atom of another group, forming a double bond, wherein R is hydrogen or alkyl.

As used herein, "optionally substituted alkyl", "optionally substituted alkenyl" and "optionally substituted alkynyl" refer to alkyl radicals, alkenyl radicals and alkynyl radicals, respectively, that may be optionally substituted by one or more substituents independently selected from the group consisting of nitro, halo, azido, cyano, cycloalkyl, heterocyclyl, heteroaryl, —OR$^x$, —N(R$^y$)(R$^z$), —SR$_x$, —C(J)R$^x$, —C(J)OR$^x$, —C(J)N(R$^y$)(R$^z$), —C(J)SR$^x$, —S(O)$_t$R$^x$ (where t is 1 or 2), —Si(R$^w$)$_3$, —N(R$^x$)S(O)$_2$R$^w$, and —S(O)$_2$N(R$^y$)(R$^z$), wherein:

R$^x$ is hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl; or R$^y$ and R$_z$, together with the nitrogen atom to which they are attached, form a heterocyclyl or heteroaryl;

R$^w$ is alkyl, alkenyl, alkynyl, cycloalkyl, cycloalkylalkyl, heterocyclyl, heterocyclylalkyl, aryl, aralkyl, heteroaryl, or heteroaralkyl;

R$^v$ is alkyl, alkenyl, alkynyl, cycloalkyl, cycloalkylalkyl, heterocyclyl, heterocyclylalkyl, aryl, aralkyl, heteroaryl, heteroaralkyl, hydroxy, —OR$^x$ or —N(R$^y$)(R$^z$); and J is O, NR$^x$ or S.

As used herein, "optionally substituted aryl", "optionally substituted cycloalkyl", "optionally substituted heteroaryl" and "optionally substituted heterocyclyl" refers to aryl, cycloalkyl, heterocyclyl and heteroaryl radicals, respectively, that are optionally substituted by one or more substituents selected from the group consisting of nitro, halo, haloalkyl, haloalkenyl, azido, cyano, oxo, thioxo, alkyl optionally substituted with halo, cyano, hydroxy, optionally substituted alkoxy, optionally substituted amino or optionally substituted sulfide, alkenyl, alkynyl, cycloalkyl, cycloalkylalkyl, heterocyclyl, heterocyclylalkyl, aryl, aralkyl, heteroaryl, heteroaralkyl, —R$^u$—OR$^x$, —R$^u$—N(R$^y$)(R$^z$), —R$^u$—SR$^x$, —R$^u$—C(J)R$^x$, —R$^u$—C(J)OR$^x$, —R$^u$—C(J)N(R$^y$)(R$^z$), —R$^u$—C(J)SR$^x$, —R$^u$—S(O)$_t$R$^x$ (where t is 1 or 2), —R$^u$—Si(R$^w$)$_3$, —R$^u$N(R$^x$)S(O)$_2$R$^w$, —R$^u$S(O)$_2$N(R$^y$)(R$^z$) wherein:

each R$^u$ is independently alkylene or a direct bond;

each R$^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —OR$^x$ or —N(R$^y$)(R$^z$);

R$^w$ is alkyl, alkenyl, alkynyl, cycloalkyl, cycloalkylalkyl, heterocyclyl, heterocyclylalkyl, aryl, aralkyl, heteroaryl, or heteroaralkyl;

each R$^x$ is independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$, together with the nitrogen atom to which they are attached, form a heterocyclyl or heteroaryl; and J is O, NR$^x$ or S.

As used herein, "oxime" refers to a divalent group such as =N—OH, which is attached to a carbon atom of another group, forming a double bond.

As used herein, "oxo" refers to an oxygen atom doubly bonded to a carbon.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "thioxo" refers to a sulfur atom doubly bonded to a carbon.

Where the number of any given substituent is not specified (e.g., haloalkyl), there may be one or more substituents present. For example, "haloalkyl" may include one or more of the same or different halogens. As another example, "C$_{1-3}$ alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 11:942-944 (1972)).

As employed herein, the following terms have their accepted meaning in the chemical literature.

AcOH acetic acid
anhyd anhydrous
CDI 1,1'-carbonyldiimidazole
CHCl$_3$ chloroform
conc concentrated
DCM dichloromethane
DOTAP N-[1-(2,3-Dioleoyloxy)]-N,N,N-trimethylammonium propane methylsulfate
DMF N,N-dimethylformamide
DMSO dimethyl sulfoxide
Et$_2$O diethyl ether
EtOAc ethyl acetate
EtOH ethanol (100%)
Hex hexanes
MeOH methanol
NH$_4$OAc ammonium acetate
Pd/C palladium on activated carbon
Pd[PPH$_3$]$_4$ Tetrakis(triphenylphosphine)palladium (0)
satd saturated
TBAF Tetrabutylammonium fluoride
TBSCl Tert-butyldimethylsilyl chloride
TEA triethylamine
THF tetrahydrofuran

B. Preferred Embodiments of the Compounds of the Invention

Compounds for use in compositions and methods for modulating the activity of nuclear receptors are provided. In particular, compounds for use in compositions and methods for modulating the vitamin D receptor are provided.

In the first embodiment, the compounds of the invention, as described above in the Summary of the Invention, are compounds of formula (I):

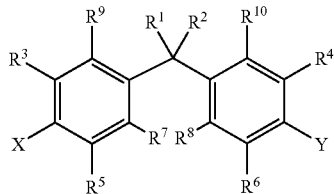

or pharmaceutically acceptable derivatives thereof, wherein:

$R^1$ and $R^2$ are each independently halo, haloalkyl, pseudohalo, optionally substituted alkyl, optionally substituted alkenyl, optionally substituted alkynyl, optionally substituted cycloalkyl, optionally substituted heterocyclyl, optionally substituted aryl or optionally substituted heteroaryl; or $R^1$ and $R^2$, together with the carbon atom to which they are attached, form an optionally substituted cycloalkyl consisting of:

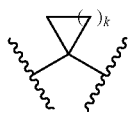

wherein k is an integer from 1 to 6; or $R^1$ and $R^2$, together with the carbon atom to which they are attached, form an optionally substituted heterocyclyl selected from a group consisting of:

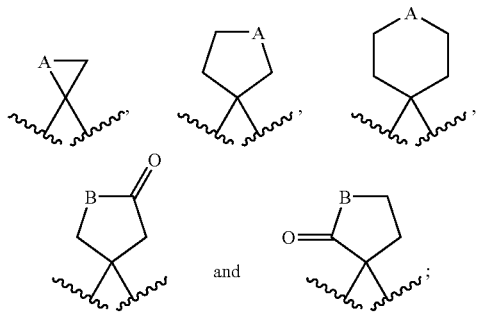

wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl; and wherein each p is independently 0 to 2;

$R^3$ and $R^4$ are each independently hydrogen, alkyl, alkenyl, alkynyl, cycloalkyl, heterocyclyl, aryl, heteroaryl, halo, pseudohalo, haloalkyl, nitro, cyano, azido, —R$^{14}$—OR$^{15}$, —R$^{14}$—N(R$^{18}$)R$^{19}$, —R$^{14}$—SR$^{15}$, —R$^{14}$—OC(J)R$^{15}$, —R$^{14}$—NR$^{17}$C(J)R$^{15}$, —R$^{14}$—OC(J)N(R$^{18}$)R$^{19}$, —R$^{14}$—NR$^{17}$C(J)N(R$^{18}$)R$^{19}$, —R$^{14}$—NR$^{17}$C(J)OR$^{15}$, —R$^{14}$—C(J)R$^{15}$, —R$^{14}$13 C(J)OR$^{15}$, —R$^{14}$C(J)SR$^{16}$, —R$^{14}$—C(J)N(R$^{18}$)R$^{19}$ or —R$^{14}$C(J)N(R$^{17}$)N(R$^{18}$)R$^{19}$;

$R^5$, $R^6$, $R^7$, $R^8$, $R^9$, $R^{10}$ are each independently hydrogen, halo, hydroxy, amino, pseudohalo, cyano, nitro, alkyl, haloalkyl, alkoxy or haloalkoxy;

X is $R^{25}$;

Y is independently $R^{30}$, —OR$^{31}$, —SR$^{32}$ or —N(R$^{33}$)(R$^{34}$);

$R^{25}$ and $R^{30}$ are each independently selected from (i) or (ii) as follows:

(i) optionally substituted alkyl that may be substituted with one to ten substituents each independently selected from a group consisting of halo, pseudohalo, nitro, cyano, thioxo, azido, amidino, guanidino, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{15}$, —OR$^{16}$OR$^{15}$, —N(R$^{18}$)R$^{19}$, —N(R$^{17}$)N(R$^{18}$)R$^{19}$1, —SR$^{15}$, —SR$^{16}$SR$^{15}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)N(R$^{17}$)S(O)$_p$R$^{20}$, —C(R$^{17}$)═NOR$^{15}$, —C(R$^{17}$)═NR$^{17}$, —C(R$^{17}$)═NN(R$^{18}$)R$^{19}$ and —C(═NR$^{17}$)N(R$^{18}$)R$^{19}$; or (ii) optionally substituted alkenyl or optionally substituted alkynyl, either of which may be substituted with one to ten substituents each independently selected from a group consisting of oxo, thioxo, halo, pseudohalo, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$—P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)═NOR$^{15}$, —C(R$^{17}$)═NR$^{17}$, —C(R$^{17}$)═NN(R$^{18}$)R$^{19}$, —C(═NR$^{17}$)N(R$^{18}$)R$^{19}$, alkyl, haloalkyl, cycloalkyl, heterocyclyl, aryl and heteroaryl;

$R^{31}$, $R^{32}$, $R^{33}$ and $R^{34}$ are each independently optionally substituted alkyl, optionally substituted alkenyl, optionally substituted alkynyl or optionally substituted cycloalkyl; all of which may be optionally substituted with one to ten substituents each independently selected from a group consisting of oxo, halo, pseudohalo, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)═NOR$^{15}$, —C(R$^{17}$)═NR$^{17}$, —C(R$^{17}$)═NN(R$^{18}$)R$^{19}$, —C(═NR$^{17}$)N(R$^{18}$)R$^{19}$, alkyl, cycloalkyl, heterocyclyl, aryl and heteroaryl, and $R^{34}$ can additionally be hydrogen;

where each $R^{14}$ is independently a direct bond or alkylene;

where each $R^{15}$ and $R^{17}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, cyano, hydroxy and amino;

where each $R^{16}$ and $R^{20}$ is independently optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino; and where each $R^{18}$ and $R^{19}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino;

or where $R^{18}$ and $R^{19}$, together with the nitrogen atom to which they are attached, form a heterocyclyl or heteroaryl;

each $R^{21}$ is independently alkyl, $-OR^{22}$ or $-N(R^{23})R^{24}$;

$R^{22}$ is hydrogen, alkyl, haloalkyl, alkenyl, alkynyl, cycloalkyl, heterocyclyl, aryl, heteroaryl or aralkyl;

$R^{23}$ and $R^{24}$ are each independently hydrogen, alkyl, haloalkyl, alkenyl, alkynyl or cycloalkyl;

or $R^{23}$ and $R^{24}$, together with the nitrogen atom to which they are attached, form a heterocyclyl or heteroaryl;

each J is independently O or S;

as a single isomer, a mixture of isomers, or as a racemic mixture of isomers; as a solvate or polymorph; or as a prodrug or metabolite; or as a pharmaceutically acceptable salt thereof;

provided that when $R^1$ and $R^2$ form a substituted cyclohexyl, said cyclohexyl, when substituted at the 4-position relative to the gem-diaryl substituents, is substituted with a substituent selected from the group consisting of halo, cyano, optionally substituted alkyl, optionally substituted alkenyl, optionally substituted alkynyl, optionally substituted aryl and optionally substituted heteroaryl; and provided that neither $R^{26}$ nor $R^{30}$ is:
$-CH_2COOH$; $-CH_2$-5-tetrazolyl; $-CH_2COOMe$; $-CH_2COOEt$; $-CH_2NH(CH_2COOH)$; $-CH_2N(C(O)Me)(CH_2COOH)$; $-CH_2$-N-pyrrolidin-2-one; $-CH_2$-(1-methylpyrrolidin-2-one-3-yl); $-CH_2COOH$; $-CH_2C(O)NH_2$; $-CH_2C(O)NMe_2$; $-CH_2C(O)NHMe$; $-CH_2C(O)$—N-pyrrolidine; $-CH(OH)COOH$; $-CH(OH)C(O)NH_2$; $-CH(OH)C(O)NHMe$; $-CH(OH)C(O)NMe_2$; $-CH(OH)C(O)NEt_2$; $-CH_2CH_2COOH$; $-CH_2CH_2COOMe$; $-CH_2CH_2COOEt$; $-CH_2CH_2COOMe$; $-CH_2CH_2COOEt$; $-CH_2CH_2C(O)NH_2$; $-CH_2CH_2C(O)NHMe$; $-CH_2CH_2C(O)NMe_2$; or $-CH_2CH_2$-5-tetrazolyl.

The first aspect of the of the first embodiment is a compound where:
X is $R^{25}$;
Y is $-SR^{32}$ or $-N(R^{33})(R^{34})$;
$R^1$ and $R^2$ are each independently alkyl or haloalkyl;
$R^3$ and $R^4$ are each independently hydrogen, halo, pseudohalo, alkyl or haloalkyl; and
$R^5, R^6, R^7, R^8, R^9, R^{10}$ are hydrogen.

The second aspect of the first embodiment is a compound where:
X is $R^{25}$;
Y is $-OR^{31}$;
$R^1$ and $R^2$ are each independently alkyl or haloalkyl;
$R^3$ and $R^4$ are each independently hydrogen, halo, pseudohalo, alkyl or haloalkyl; and
$R^5, R^6, R^7, R^8, R^9, R^{10}$ are hydrogen.

The third aspect of the first embodiment is a compound where:
X is $R^{25}$;
Y is $-OR^{31}$;
$R^1$ and $R^2$ are each independently alkyl or haloalkyl;
$R^3$ and $R^4$ are each independently hydrogen, halo, pseudohalo, alkyl or haloalkyl;
$R^{25}$ and $R^{31}$ are optionally substituted alkyl; and
$R^5, R^6, R^7, R^8, R^9, R^{10}$ are hydrogen.

The fourth aspect of the first embodiment is a compound where:
X is $R^{25}$;
Y is $-OR^{31}$;
$R^1$ and $R^2$ are each independently alkyl or haloalkyl;
$R^3$ and $R^4$ are each independently halo, alkyl or haloalkyl;
$R^{25}$ is optionally substituted alkenyl;
$R^{31}$ is optionally substituted alkyl; and
$R^5, R^6, R^7, R^8, R^9, R^{10}$ are hydrogen.

The fifth aspect of the first embodiment is a compound where:
X is $R^{25}$;
Y is $-OR^{31}$;
$R^1$ and $R^2$ are each independently alkyl or haloalkyl;
$R^3$ and $R^4$ are each independently halo, alkyl or haloalkyl;
$R^{25}$ is optionally substituted alkynyl;
$R^{31}$ is optionally substituted alkyl; and
$R^5, R^6, R^7, R^8, R^9, R^{10}$ are hydrogen.

The sixth aspect of the first embodiment is a compound where X is $R^{25}$ and Y is $R^{30}$.

The seventh aspect of the first embodiment is a compound where X is $R^{25}$; Y is $R^{30}$; and
$R^{25}$ and $R^{30}$ are each independently substituted alkyl, substituted alkenyl or substituted alkynyl.

The eighth aspect of the first embodiment is a compound where:
X is $R^{25}$;
Y is $R^{30}$; and
$R^{25}$ and $R^{30}$ are each independently substituted alkyl, substituted alkenyl or substituted alkynyl; and $R^3$ and $R^4$ are each independently alkyl or haloalkyl.

The ninth aspect of the second embodiment is a compound where:
X is $R^{25}$;
Y is $-N(R^{28})R^{29}$
$R^1$ and $R^2$ are ethyl;
$R^3$ and $R^4$ are methyl;
$R^{25}$ is optionally substituted alkyl, optionally substituted alkenyl or optionally substituted alkynyl;
$R^{28}$ and $R^{29}$ are selected from (i) and (ii) as follows:
$R^{28}$ and $R^{29}$ are optionally substituted alkyl,
one of $R^{28}$ and $R^{29}$ is optionally substituted alkyl and the other of $R^{28}$ and $R^{29}$ is hydrogen.

The tenth aspect of the second embodiment is a compound where:
X is $R^{25}$;
Y is $-N(R^{28})R^{29}$
$R^1$ and $R^2$ are ethyl;
$R^3$ and $R^4$ are methyl;
$R^{25}$ is optionally substituted alkyl selected from group (a) or group (b) as defined above, optionally substituted alkenyl selected from group (c) or group (d) as defined above or optionally substituted alkynyl selected from group (e) or group (e as defined above;
$R^{28}$ and $R^{29}$ are selected from (i) and (ii) as follows:
$R^{28}$ and $R^{29}$ are optionally substituted alkyl selected from group (a) or group (b) as defined above, one of $R^{28}$ and $R^{29}$ is optionally substituted alkyl and the other of $R^{28}$ and $R^{29}$ is hydrogen.

In another aspect of the first embodiment, the preferred compounds are:

3-(2-Methyl-4-{2,2,2-trifluoro-1-[4-(2-hydroxy-3,3-dimethyl-butoxy)-3-methyl-phenyl]-1-phenyl-ethyl}-phenoxy)-propane-1,2-diol;

3-(4-{4-[4-(2-Hydroxy-3,3-dimethyl-butoxy)-3-methyl-phenyl]-piperidin-4-yl}-2-methyl-phenoxy)-propane-1,2-diol;

3-(4-{4-[4-(2-Hydroxy-3,3-dimethyl-butoxy)-3-methyl-phenyl]-piperidin-4-yl}-2-methyl-phenoxy)-propane-1,2(S)-diol;

1-{4-[4-(2(S),3-Dihydroxy-propoxy)-3-methyl-phenyl]-4-[4-(2-hydroxy-3,3-dimethyl-butoxy)-3-methyl-phenyl]-piperidin-1-yl}-ethanone; and 1-(4-{1-Acetyl-4-[4-(3,3-dimethyl-2-oxo-butoxy) -3-methyl-phenyl]-piperidin-4-yl}-2-methyl-phenoxy)-3,3-dimethyl-butan-2-one.

The second embodiment of the invention is a compound of formula (I) wherein:

$R^1$ and $R^2$ are each independently halo, haloalkyl, pseudohalo, optionally substituted alkyl, optionally substituted alkenyl, optionally substituted alkynyl, optionally substituted cycloalkyl, optionally substituted heterocyclyl, optionally substituted aryl or optionally substituted heteroaryl; or $R^1$ and $R^2$, together with the carbon atom to which they are attached, form an optionally substituted cycloalkyl consisting of:

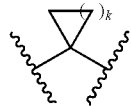

wherein k is an integer from 1 to 6; or $R^1$ and $R^2$, together with the carbon atom to which they are attached, form an optionally substituted heterocyclyl selected from a group consisting of:

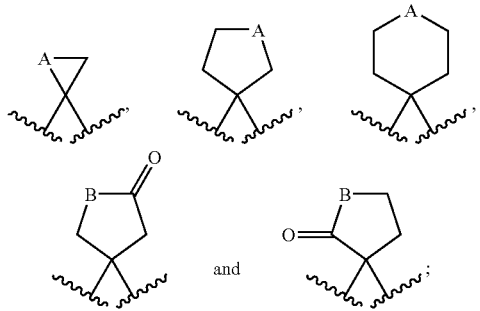

wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$—C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl; and wherein each p is independently 0 to 2;

$R^3$ and $R^4$ are each independently hydrogen, alkyl, alkenyl, alkynyl, cycloalkyl, heterocyclyl, aryl, heteroaryl, halo, pseudohalo, haloalkyl, nitro, cyano, azido, —R$^{14}$—OR$^{15}$, —R$^{14}$—N(R$^{18}$)R$^{19}$, —R$^{14}$—SR$^{15}$, —R$^{14}$—OC(J)R$^{15}$, —R$^{14}$—NR$^{17}$C(J)R$^{15}$, —R$^{14}$—OC(J)N(R$^{18}$)R$^{19}$, —R$^{14}$—NR$^{17}$C(J)N(R$^{18}$)R$^{19}$, —R$^{14}$—NR$^{17}$C(J)OR$^{15}$, —R$^{14}$—C(J)R$^{15}$, —R$^{14}$—C(J)OR$^{15}$, —R$^{14}$—C(J)SR$^{16}$, —R$^{14}$—C(J)N(R$^{18}$)R$^{19}$ or —R$^{14}$C(J)N(R$^{17}$)N(R$^{18}$)R$^{19}$;

$R^5$, $R^6$, $R^7$, $R^8$, $R^9$, $R^{10}$ are each independently hydrogen, halo, hydroxy, amino, pseudohalo, cyano, nitro, alkyl, haloalkyl, alkoxy or haloalkoxy;

$R^{25}$, $R^{30}$, $R^{31}$, $R^{32}$, $R^{33}$ and $R^{34}$ are each independently optionally substituted alkyl selected from group a) or group b), optionally substituted alkenyl selected from group c) or group d) or optionally substituted alkynyl selected from group e) or group f); and $R^{31}$, $R^{32}$, $R^{33}$ and $R^{34}$ can additionally be optionally substituted cycloalkyl selected from group g); and $R^{34}$ can additionally be hydrogen;

wherein group (a) consists of:

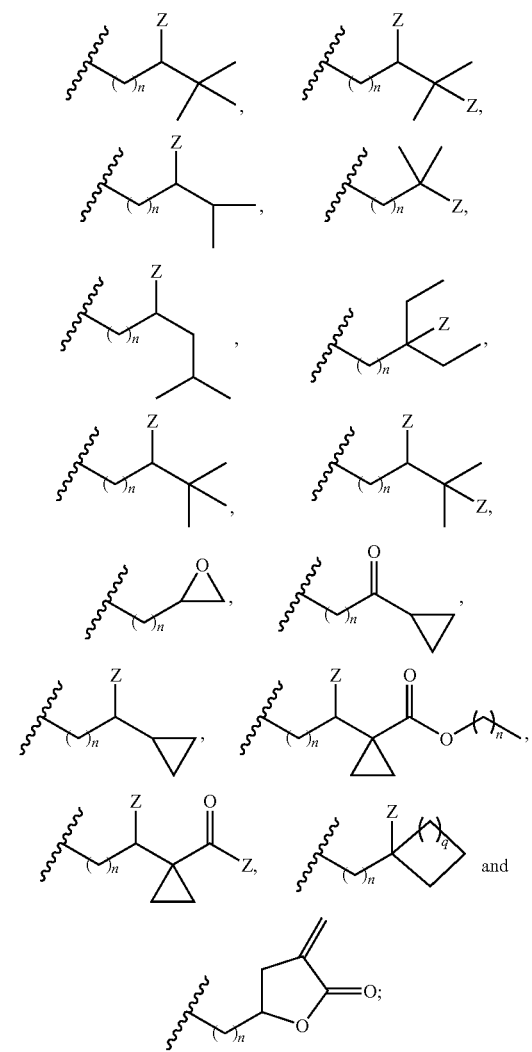

wherein group (b) consists of:
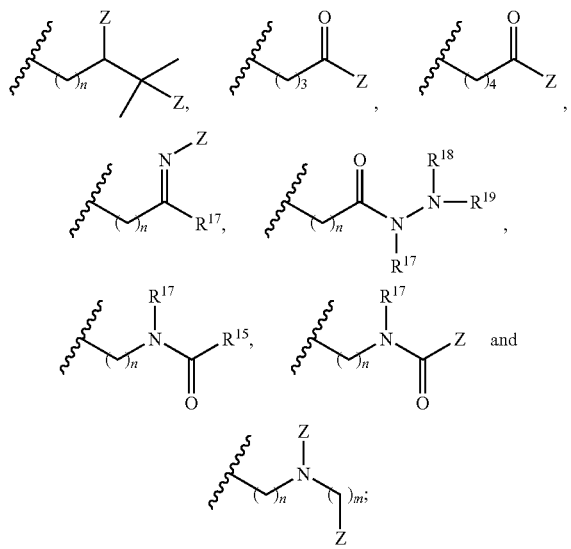
wherein group (c) consists of both cis and trans conformations of:
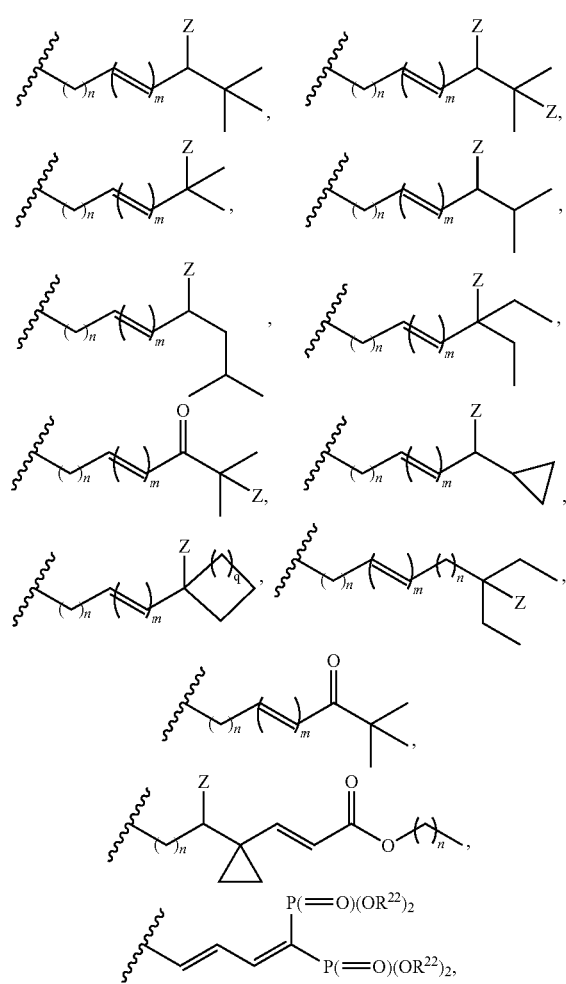
-continued
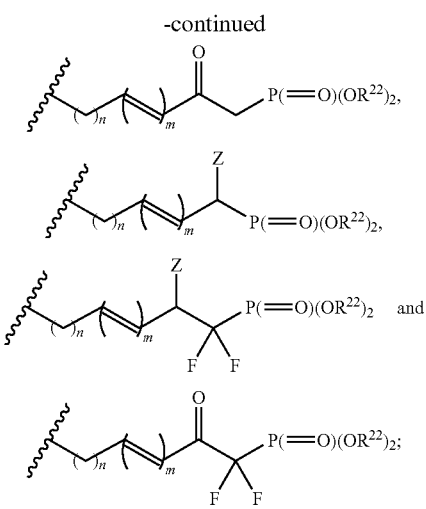
and group (d) consists of both cis and trans conformations of:
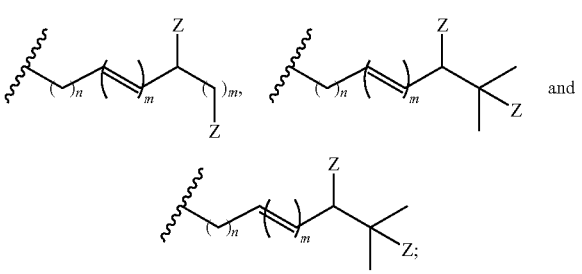
wherein group (e) consists of:
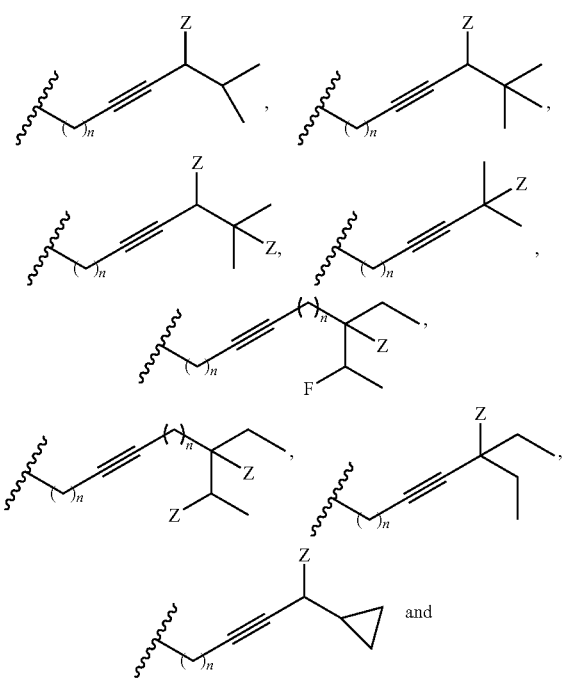

-continued

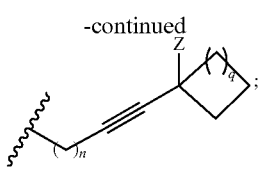

wherein group (f) consists of:

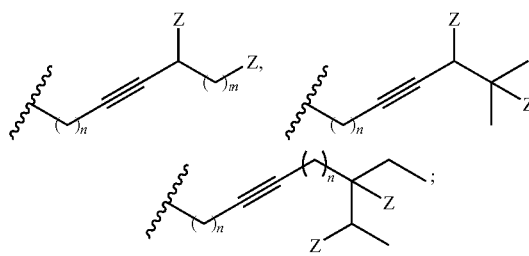

and wherein group (g) consists of:

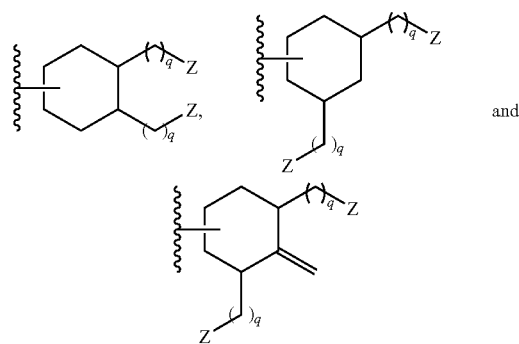

wherein each Z is independently OH, OR, $NH_2$, NHR, N(R)(R) wherein R is each independently alkyl or haloalkyl; each n is independently an integer from 0 to 4; each m is independently an integer from 1 to 2 and each q is independently an integer from 0 to 4;

wherein any member of groups a), b) c), d), e), f) and g) may optionally be halogenated; and wherein $R^{14}$-$R^{20}$ are defined in the Summary of the Invention.

The first aspect of the second embodiment is a compound having the formula (I) wherein:

X is $R^{25}$;

Y is —$OR^{31}$;

$R^1$ and $R^2$ are each independently alkyl or haloalkyl;

$R^3$ and $R^4$ are each independently hydrogen, halo, pseudohalo, alkyl or haloalkyl;

$R^5$, $R^6$, $R^7$, $R^8$, $R^9$, $R^{10}$ are hydrogen; and $R^{25}$ and $R^{31}$ are each independently optionally substituted alkyl, optionally substituted alkenyl, optionally substituted alkynyl or optionally substituted cycloalkyl.

The second aspect of the second embodiment is a compound having the formula (I) wherein:

X is $R^{25}$;

Y is —$OR^{31}$;

$R^1$ and $R^{21}$, together with the carbon atom to which they are attached, form an optionally substituted cycloalkyl or optionally substituted heterocyclyl, herein said cycloalkyl is

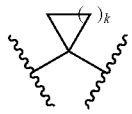

wherein k is an integer from 1 to 6;

and wherein said heterocyclyl is selected from a group consisting of:

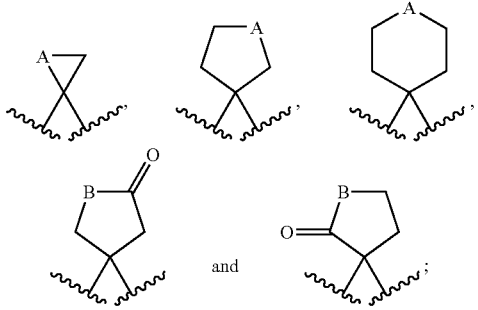

wherein A is —O—, —$NR^x$—, —S—, —S(O)— or —$S(O)_2$— wherein $R^x$ is hydrogen, alkyl, cycloalkyl, heterocyclyl, aryl, heteroaryl, amidino, guanidino, —$R^{14}$—C(J) $R^{15}$, —$R^{14}$—(J)$OR^{15}$, —$R^{14}$—C(J)$R^{16}OR^{15}$, —$R^{14}$—C(J) $SR^{16}$, —$R^{14}$-C(J)N($R^{18}$)$R^{19}$, —$R^{14}$—C(J)N($R^{17}$)N($R^{18}$) $R^{19}$, —$R^{14}$—(J)N($R^{17}$)$S(O)_pR^{20}$, —$R^{14}$—$S(O)_pN(R^{18})R^{19}$ or —$R^{14}$—$S(O)_pR^{20}$; wherein B is —O—, —S— or —$NR^y$—, $R^y$ is hydrogen, alkyl, aryl or heteroaryl; and each p is independently 0 to 2;

$R^3$ and $R^4$ are each independently hydrogen, halo, pseudohalo, alkyl or haloalkyl, $R^5$, $R^6$, $R^7$, $R^8$, $R^9$, $R^{10}$ are hydrogen; and $R^{25}$ and $R^{31}$ are each independently optionally substituted alkyl selected from group (a) or group (b) as defined above, optionally substituted alkenyl selected from group (c) or group (d) as defined above, optionally substituted alkynyl selected from group (e) or group (f) as defined above; optionally substituted cycloalkyl selected from group (g) as defined above, optionally substituted aryl selected from group (h) as defined above or optionally substituted heteroaryl;

wherein $R^{14}$-$R^{20}$ are defined in the Summary of the Invention.

The third aspect of the second embodiment is a compound where $R^{25}$ and $R^{31}$ are optionally substituted alkyl.

The fourth aspect of the second embodiment is a compound where $R^{25}$ is selected from group (a) and $R^{31}$ is selected from group (b).

The fifth aspect of the second embodiment, are the following compounds:

3-(4-{1-ethyl-1-[4-(3-hydroxy-3-methylbutyl)-3-methylphenyl]-propyl}-2-methylphenoxy)-propane-1,2(S)-diol;

3-(4-{1-ethyl-1-[4-(3-ethyl-3-hydroxypentyl)-3-methylphenyl]-propyl}-2-methyl-phenoxy)-propane-1,2(S)-diol;

3-(4-{1-ethyl-1-[4-(3-hydroxy-5-methylhexyl)-3-methylphenyl]-propyl}-2-methyl-phenoxy)-propane-1,2(S)-diol;

3-(4-{1-ethyl-1-[4-(3-hydroxy-4-methylpentyl)-3-methylphenyl]-propyl}-2-methyl-phenoxy)-propane-1,2(S)-diol;

3-(2-ethyl-4-{1-ethyl-1-[4-(3-hydroxy-4,4-dimethylpentyl)-3-methylphenyl]-propyl}-phenoxy)-propane-1,2(S)-diol;

3-(4-{1-ethyl-1-[4-(3-hydroxy-4,4-dimethylpentyl)-3-methylphenyl]-propyl}-2-methyl-phenoxy)-propane-1,2(S)-diol;

3-[4-(1-ethyl-1-{4-[3(S)-hydroxy-4,4-dimethylpentyl]-3-methylphenyl}-propyl)-2-methyl-phenoxy]-propane-1,2(S)-diol; and 3-[4-(1-ethyl-1-{4-[3(R)-hydroxy-4,4-dimethylpentyl]-3-methylphenyl}-propyl)-2-methyl-phenoxy]-propane-1,2(S)-diol.

The sixth aspect of the second embodiment is a compound where $R^{25}$ is selected from group (a); $R^{31}$ is selected from group (b); $R^3$ is hydrogen and $R^4$ is alkyl or haloalkyl.

The seventh aspect of the second embodiment is the compound 3-(4-{1-ethyl-1-[4-(3-hydroxy-4,4-dimethylpentyl)-phenyl]-propyl}-2-methylphenoxy)-propane-1,2(S)-diol.

The eighth aspect of the second embodiment is a compound where $R^{25}$ is selected from group (a); $R^{31}$ is selected from group (b); $R^3$ is alkyl or haloalkyl and $R^4$ is hydrogen.

The ninth aspect of the second embodiment is the compound 3-(4-{1-ethyl-1-[4-(3-hydroxy-4,4-dimethylpentyl)-phenyl]-propyl}-2-methylphenoxy)-propane-1,2(S)-diol.

The tenth aspect of the second embodiment is a compound where $R^{25}$ is optionally substituted alkenyl and $R^{31}$ is optionally substituted alkyl.

The eleventh aspect of the second embodiment is a compound where $R^{25}$ is selected from group (c) and group (d) and $R^{31}$ is selected from group (a) and group (b).

The twelfth aspect of the second embodiment are the compounds:

(Z)-3-(4-{1-ethyl-1-[4-(3-hydroxy-4,4-dimethylpent-1-enyl)-3-methylphenyl]-propyl}-2-methylphenoxy)-propane-1,2(S)-diol;

(E)-3-(4-{1-ethyl-1-[4-(3-hydroxy-4,4-dimethylpent-1-enyl)-3-methylphenyl]-propyl}-2-methylphenoxy)-propane-1,2(S)-diol; and (E)-3-(4-{1-ethyl-1-[4-(3-ethyl-3-hydroxypent-1-enyl)-3-methylphenyl]-propyl}-2-methylphenoxy)-propane-1,2(S)-diol.

The thirteenth aspect of the second embodiment is a compound where $R^{25}$ is optionally substituted alkynyl and $R^{31}$ is optionally substituted alkyl.

The fourteenth aspect of the second embodiment is a compound where $R^{25}$ is selected from group (e) and group (f) and $R^{31}$ is selected from group (a) and group (b).

The fifteenth aspect of the second embodiment, are the compounds:

3-(4-{1-ethyl-1-[4-(3-hydroxy-4,4-dimethylpent-1-ynyl)-3-methylphenyl]-propyl}-2-methylphenoxy)-propane-1,2 (S)-diol;

3-(4-{1-ethyl-1-[4-(3(R)-hydroxy-4,4-dimethylpent-1-ynyl)-3-methylphenyl]-propyl}-2-methylphenoxy)-propane-1,2(S)-diol;

3-(4-{1-ethyl-1-[4-(3(S)-hydroxy-4,4-dimethylpent-1-ynyl)-3-methylphenyl]-propyl}-2-methylphenoxy)-propane-1,2(S)-diol; and 3-(4-{1-ethyl-1-[4-(3-ethyl-3-hydroxypent-1-ynyl)-3-methyl-phenyl]-propyl}-2-methylphenoxy)-propane-1,2(S)-diol.

The sixteenth aspect of the second embodiment, is a compound having the formula (I) wherein:
$R^1$, $R^2$, $R^3$ and $R^4$ are alkyl;
X is $R^{25}$;
Y is —$OR^{31}$;

$R^{25}$ is optionally substituted alkyl, optionally substituted alkenyl or optionally substituted alkynyl;
and $R^{31}$ is optionally substituted alkyl.

The seventeenth aspect of the second embodiment, is a compound having the formula (I) wherein:
$R^1$ and $R^2$ are ethyl and $R^3$ and $R^4$ are methyl.

The eighteenth aspect of the second embodiment, is a compound wherein:
$R^1$ and $R^2$ are ethyl;
$R^3$ and $R^4$ are methyl;
$R^{25}$ and $R^{31}$ are substituted alkyl.

The nineteenth aspect of the second embodiment, is a compound where: $R^{25}$ is selected from:

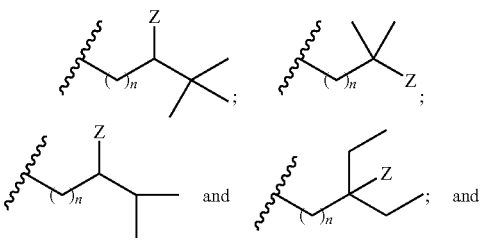

wherein $R^{31}$ is

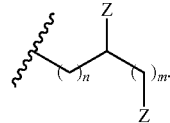

The twentieth aspect of the second embodiment is a compound where:
$R^1$ and $R^2$ are ethyl;
$R^3$ and $R^4$ are methyl;
$R^{25}$ is substituted alkenyl; and
$R^{31}$ is substituted alkyl.

The twenty-first aspect of the second embodiment is a compound where: $R^{25}$ is selected from both cis and trans conformations of:

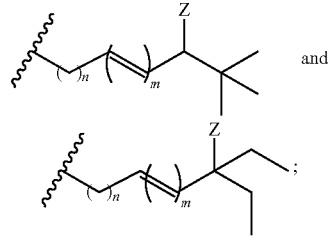

and wherein $R^{31}$ is selected from:

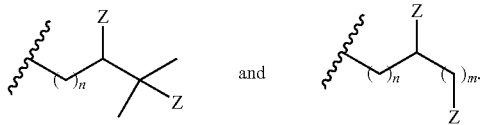

The twenty-second aspect of the second embodiment is a compound where:
$R^1$ and $R^2$ are ethyl;
$R^3$ and $R^4$ are methyl;
$R^{25}$ is substituted alkynyl; and
$R^{25}$ is substituted alkyl.

The twenty-third aspect of the second embodiment is a compound where:
$R^{25}$ is selected from

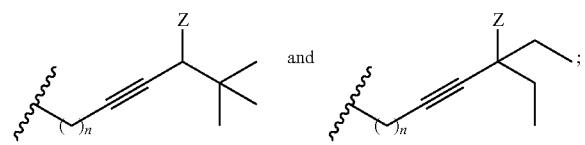

and wherein $R^{31}$ is selected from:

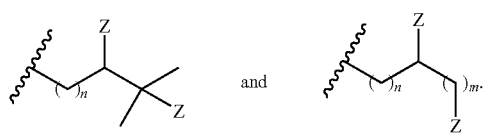

The twenty-fourth aspect of the preferred embodiment is a compound of the invention is a compound having the formula (I) wherein:
X is $R^{25}$;
Y is $R^{30}$;
$R^1$ and $R^2$ are each independently alkyl or haloalkyl;
$R^3$ and $R^4$ are each independently hydrogen, halo, pseudohalo, alkyl or haloalkyl,
$R^5$, $R^6$, $R^7$, $R^8$, $R^9$, $R^{10}$ are hydrogen; and
$R^{25}$ and $R^{30}$ are each independently optionally substituted alkyl, optionally substituted alkenyl, optionally substituted alkynyl or optionally substituted cycloalkyl.

The twenty-fifth aspect of the preferred embodiment, is a compound having the formula (I) wherein:
X is $R^{25}$;
Y is $R^{30}$;
$R^1$ and $R^2$, together with the carbon atom to which they are attached, form an optionally substituted cycloalkyl or optionally substituted heterocyclyl,
wherein said cycloalkyl is

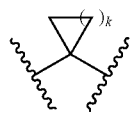

wherein k is an integer from 1 to 6;
and wherein said heterocyclyl is selected from a group consisting of:

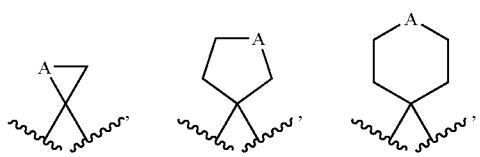

-continued

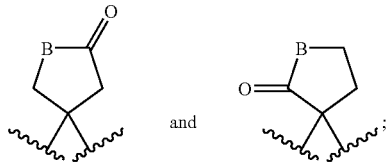

wherein A is —O—, —$NR^x$—, —S—, —S(O)— or —$S(O)_2$— wherein $R^x$ is hydrogen, alkyl, cycloalkyl, heterocyclyl, aryl, heteroaryl, amidino, guanidino, —$R^{14}$—C(J)$R^{15}$, —$R^{14}$—C(J)O$R^{15}$, —$R^{14}$—C(J)$R^{16}$O$R^{15}$, —$R^{14}$—C(J)S$R^{16}$, —$R^{14}$—C(J)N($R^{18}$)$R^{19}$, —$R^{14}$—C(J)N($R^{17}$)N($R^{18}$)$R^{19}$, —$R^{14}$—C(J)N($R^{17}$)S(O)$_p$$R^{20}$, —$R^{14}$—S(O)$_p$N($R^{18}$)$R^{19}$ or —$R^{14}$—S(O)$_p$$R^{20}$; and wherein B is —O—, —S— or —$NR^y$— wherein $R^y$ is hydrogen, alkyl, aryl or heteroaryl; and wherein each p is independently 0 to 2;
$R^3$ and $R^4$ are each independently hydrogen, halo, pseudohalo, alkyl or haloalkyl,
$R^5$, $R^6$, $R^7$, $R^8$, $R^9$, $R^{10}$ are hydrogen; and
$R^{25}$ and $R^{30}$ are each independently optionally substituted alkyl selected from group (a) or group (b) as defined above, optionally substituted alkenyl selected from group (c) or group (d) as defined above, optionally substituted alkynyl selected from group (e) or group (f as defined above; optionally substituted cycloalkyl selected from group (g) as defined above, optionally substituted aryl selected from group (h) as defined above or optionally substituted heteroaryl;
wherein $R^{14}$-$R^{20}$ are defined in the Summary of the Invention.

The twenty-sixth aspect of the second embodiment, is a compound where $R^{25}$ and $R^{30}$ are selected from group (a) and group (b).

The twenty-seventh aspect of the second embodiment, is a compound where $R^{25}$ is selected from group (c) and group (d) and $R^{30}$ is selected from group (a) and group (b).

The twenty-eighth aspect of the second embodiment, is a compound where $R^{25}$ is selected from group (e) and group (f) and $R^{30}$ is selected from group (a) and group (b).

The twenty-ninth aspect of the second embodiment is a compound where, $R^{25}$ and $R^{30}$ are selected from group (c) and group (d).

The thirtieth aspect of the second embodiment is a compound where $R^{25}$ is selected from group (c) or group (d) and $R^{30}$ is selected from group (e) or group (f).

The thirty-first aspect of the second embodiment is a compound where $R^{25}$ and $R^{30}$ are selected from group (e) or group (f).

The thirty-second aspect of the second embodiment is a compound where:
X is $R^{25}$;
Y is —$SR^{27}$
$R^1$ and $R^2$ are ethyl;
$R^3$ and $R^4$ are methyl;
$R^{25}$ is optionally substituted alkyl selected from group (a) or group (b) as defined above, optionally substituted alkenyl selected from group (c) or group (d) as defined above or optionally substituted alkynyl selected from group (e) or group (f) as defined above; and
$R^{27}$ is optionally substituted alkyl selected from group (a) or group (b) as defined above.

C. Preparation of the Compounds

Starting materials in the synthesis examples provided herein are either available from commercial sources or via literature procedures. All commercially available compounds were used without further purification unless otherwise indicated. $CDCl_3$ (99.8% D, Cambridge Isotope Laboratories), CD$_2$Cl$_2$ (99.9% D, Cambridge Isotope Laboratories), C$_6$D$_6$ (99.5% D, Cambridge Isotope Laboratories) and DMSO-d$_6$ (99.9% D, Cambridge Isotope Laboratories) were used in all experiments as indicated. Proton ($^1$H) nuclear magnetic resonance (NMR) spectra were recorded on a Bruker Avance 400 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid or 0.05% ammonium acetate). Flash chromatography was performed using Merck Silica Gel 60 (230-400 mesh) following standard protocol (Still et al. *J. Org. Chem.* 43, 2923 (1978)).

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Protecting groups may be added or removed in accordance with standard techniques, which are well known to those skilled in the art and as described herein. The use of protecting groups is described in detail in Green, T. W. and P. G. M. Wutz, *Protective Groups in Organic Synthesis* (1991), 2nd Ed., Wiley-Interscience.

The following illustrations depict general preparations of compounds claimed herein and consist of reactions typically known to one skilled in the art of chemical synthesis. The substituents R$^1$-R$^{34}$, X and Y are as defined above in the Summary of the Invention. One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent to one skilled in the art that many of the products could exist as one or more isomers, that is E/Z isomers, enantiomers and/or diastereomers.

In general, compounds of Formula I, such as diaryl compounds (3), can be prepared via acid-catalyzed reactions as depicted in Scheme 1. Thus, for example, when the aromatic compound (1) is phenol (e.g. X=OH), it can be condensed with an aralkyl alcohol (2) to yield the diaryl product, 3 (e.g. X=OH). Similar products 3 also can be achieved with substituted styrenes in place of 2 under conditions mediated by acid or Lewis acid. Thiophenols 1 (X=SH) also can undergo similar condensation reactions to afford thiophenol products, 3 (X=SH).

SCHEME 1

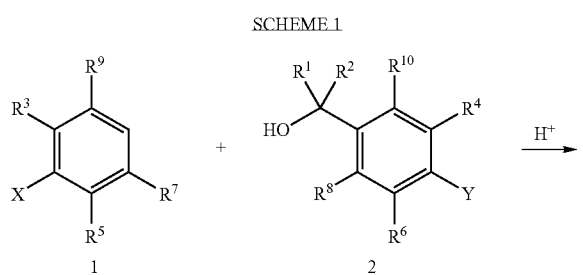

-continued

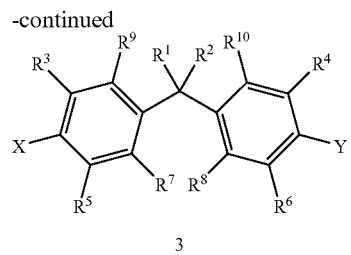

3

In addition, symmetric compounds, such as gem-diarylalkanes (5), can be prepared under similar conditions as depicted in Scheme 2. Thus, for example, when the aromatic compound (4) is an ortho-substituted phenol (X=OH), it can be condensed with ketones (e.g. R$^1$R$^2$CO) to yield diphenols, 5 (X=OH). Likewise cyclic and heterocyclic ketones can be condensed with 4 to give spiro-cyclic and spiro-heterocyclic diphenols, respectively, in which R$^1$ and R$^2$ together form cycloalkyl and heterocyclyl substituents. Thiophenols 4 (X=SH) also can undergo similar condensation reactions to afford dithiophenols, 5 (X=SH).

SCHEME 2

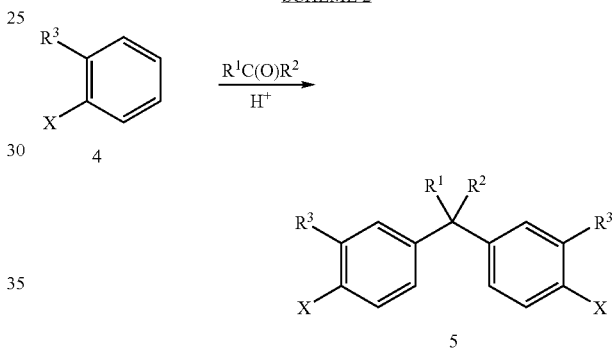

Additional compounds of Formula I can be achieved by producing derivatives of the above products, e.g. diphenols. Thus, for example, phenol 3 or diphenol 5 can react with an electrophile, e.g. alkyl halide, to yield the corresponding product, e.g. an alkyl aryl ether. Furthermore, for example, phenols (3 or 5) can react with aziridines, epoxides, isocyanates, isothiocyanates to afford aminoalkyl ethers, hydroxyalkyl ethers, carbamates and thiocarbamates, respectively. Thiophenols (3 or 5, X=SH) also can undergo similar reactions with electrophiles to form the corresponding products, e.g. thioethers from reactions with alkyl halides.

As depicted in Scheme 3, phenols (e.g. 3) can be transformed via the Ullmann ether synthesis (see, e.g. Marcoux et al. *J. Am. Chem. Soc.* 119, 10539 (1997)) into diaryl ethers (6).

SCHEME 3

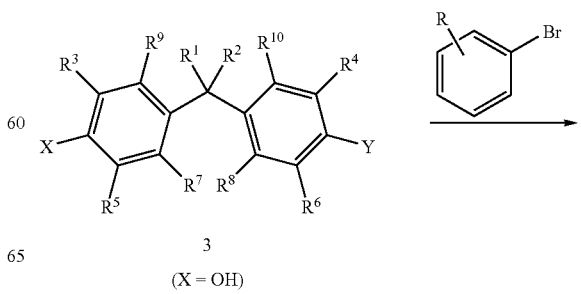

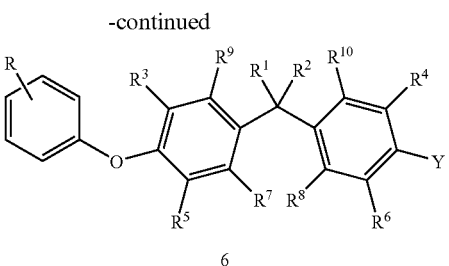

6

Phenols 3 (e.g. X=OH) can be converted to the corresponding aryl triflates 3 (e.g. X=OTf) and subsequently transformed via transition metal-catalyzed C—C, C—O or C—N bond-forming reactions into a wide variety of additional compounds, as depicted in Scheme 4. In addition, when the aromatic compound 3 is an aryl halide 3 (e.g. X=Br), it can undergo the same transformations. These cross-coupling reactions are well known to those skilled in the art and have been widely reported in the literature. Thus, aryl triflates, bromides, chlorides and iodides 3 can undergo cross-coupling reactions with the appropriate reagents, as depicted in Scheme 4 for selected sytheses, that include but are not limited to the following processes: Suzuki, Heck, Stille, Sonogashira, Negishi, aryl amination, aryl amidation, aryl acylation, aryl carbonylation and ketone arylation (for general review, see: (a) *Metal-catalyzed Cross-coupling Reactions*; Diederich, F., Stang, P. J., Eds.; Wiley-VCH: New York, 1998; (b) *Palladium Reagents and Catalysis: Innovations in Organic Synthesis*; Tsuji, J.; John Wiley & Sons: New York, 1995).

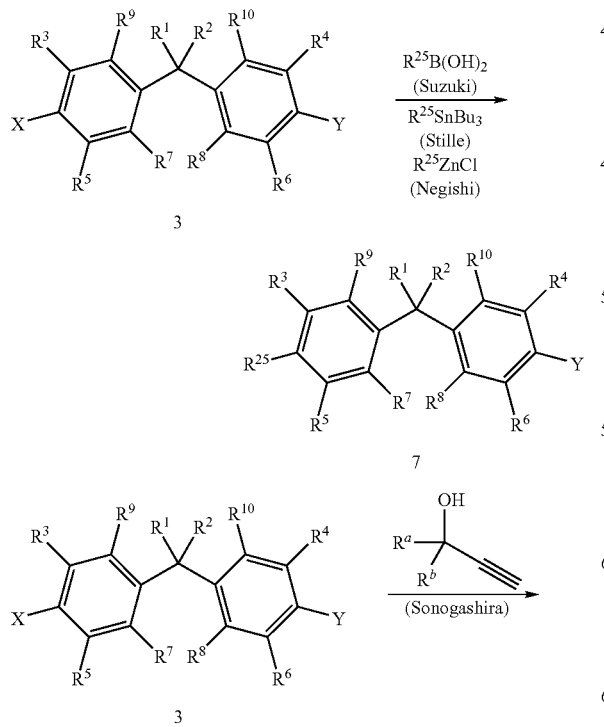

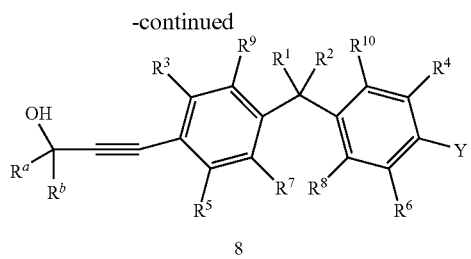

8

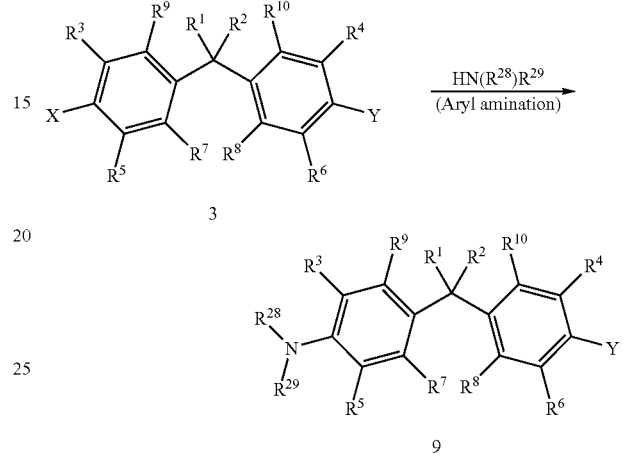

X = OTf, Br, Cl, I

Further elaboration of the above compounds also can be pursued in many different ways, which are known to one skilled in the art. For example, the alkyne 8 can be reduced partially via LiAlH$_4$ (see, e.g. Borden, W. T. *J. Am. Chem. Soc.* 92, 4898-4901(1970)) or Lindlar catalyst to yield the corresponding E- or Z-alkene, respectively. Scheme 5 depicts the preparation of E-alkene 10. Furthermore 8 can undergo complete reduction via Pd/C-catalyzed hydrogenation to give the corresponding alkane.

SCHEME 5

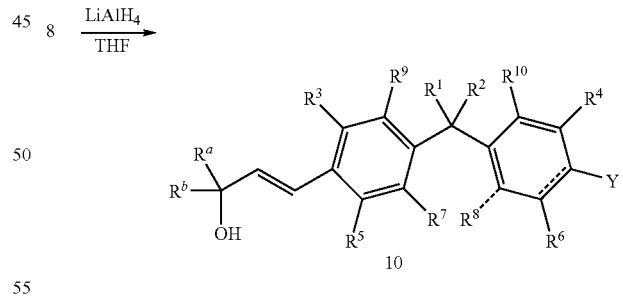

In addition, where R$^{28}$ is hydrogen, for example, aryl amine 9, can be reacted with various electrophiles, e.g. sulfonyl chloride to afford sulfonamide 9 (R$^{28}$=S(O)$_2$R). Also the same amine 9 can undergo numerous other reactions such as reductive amination with an aldehyde or further aryl amination with aryl bromides to yield diaryl amines.

Diaryl compounds (13), such that R$^1$ and R$^2$ of Formula I together form an oxo group, can be prepared under various conditions. For example, Scheme 6 depicts the production of ketones 13 via cross-coupling reactions of benzoyl chlorides (11) and aryl bromides (12) mediated by an active copper species (Stack, D. E., et al. *J. Am. Chem. Soc.* 113, 4672-4673 (1991)). The resulting diaryl ketones 13 can be converted to epoxides via addition of sulfur ylides or diazoalkanes, as widely reported in the literature. The resulting epoxide can be transformed into episulfides under conditions known to one skilled in the art. Ketone 13 also can undergo typical olefination reactions, i.e. Wittig or Horner-Emmons-Wadsworth olefinations, to yield the desired alkene (14), as shown in Scheme 6 (Maercker *Org. React.* 14: 270-490 (1965); Wadsworth, Jr. *Org. React.* 25:73-253 (1977)). In addition, 13 can be converted to alkene 14 via addition of an organolithium or Grignard reagent followed by dehydration of the resulting carbinol. Alkene 14 can be converted to products such as aziridines, epoxides and cyclopropanes. Thus, for example, aziridines can be prepared upon thermolysis or photolysis of a mixture of an azide and alkene 14.

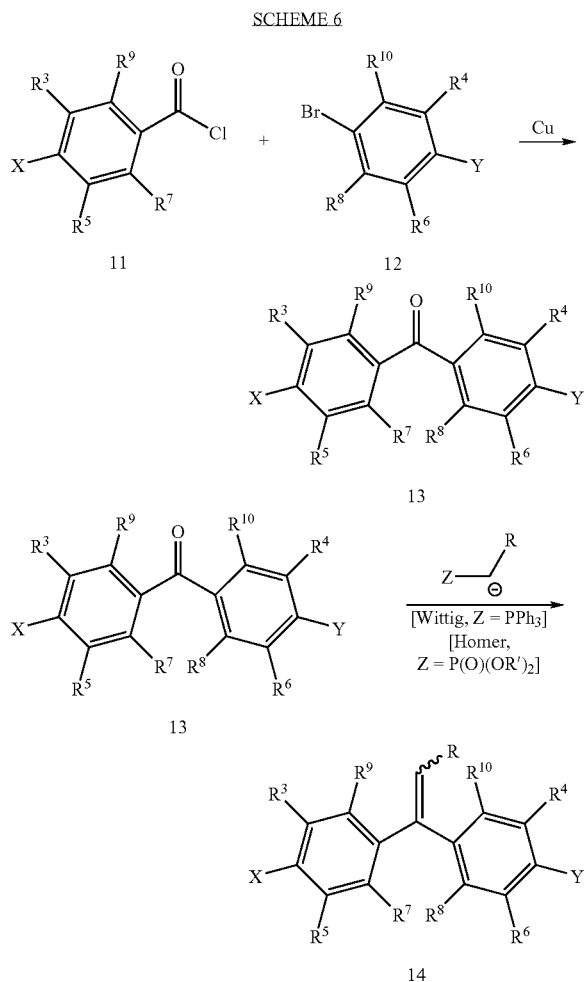

SCHEME 6

D. Evaluation of the Activity of the Compounds

Those of skill in the art recognize that various methods may be used to characterize and profile the activity of the claimed compounds and compositions. Preferably such compounds exhibit an $EC_{50}$ or $IC_{50}$ of 10 µM or less for the vitamin D receptor in one of the in vivo or in vitro assays described herein. Preferably such compounds exhibit an affinity, as measured via any of the methods disclosed herein, of at least 500 nM, preferably at least 200 nM, more preferably at least 100 nM, and most preferably at least 20 nM.

Suitable cell based assays for assaying the activity of the claimed compounds include, but are not limited to, the co-transfection assay, the use of LBD-Gal 4 chimeras and protein-protein interaction assays (see, for example, Lehmann. et al., *J. Biol Chem.*, 272, No. 6 3137-3140 (1997)).

In addition many biochemical screening formats exist for screening compound activities to identify high affinity ligands which include, but are not limited to, direct binding assays, ELISAs, fluorescence polarization assays, FRET and Time resolved FRET based coactivator recruitment assays (see, generally, Glickman et al., *J. Biomolecular Screening* 7, No. 1, 3-10 (2002)).

One method of characterizing vitamin D analogs or mimics is to measure their binding affinity to the serum VDR binding protein (VBP). There is believed to be a positive correlation between VBP binding affinity and its hypercalcemic activity, and a VBP binding assay may be used to assess the hypercalcemic properties of a given compound.

Standard methods for performing DBP competition binding assays are described in the literature (See, Boehm et al., *Chem. Biol* 6:265-275 (1999), Dusso et al. *Endocrinology* 128 (4): 1687-92 (1991)). In general the method involves using rat serum as the source of DBP and incubating diluted serum with $^3H$-1,25$(OH)_2D_3$ plus and minus cold competitor compounds. Bound and free $^3H$-1,25$(OH)_2D_3$ will be separated by dextran/charcoal, samples centrifuged, and supernatants collected and counted in a scintillation counter.

Direct binding assays can be established to determine the relative binding of the claimed compounds to the VDR. Binding to the VDR can be accomplished by expression of full length human VDR in a yeast expression plasmid as described previously (D. P. McDonnell et al. *Mol Cell Biol.* 9, 3517-3523 (1989)). Cell extracts from yeast transformants may be prepared and used for saturation and Scatchard analyses using tritiated 1,25$(OH)_2D_3$ (Amersham). Hydroxylapatite resin can be used to separate bound from unbound ligand as described previously (E. A. Allegretto et al. *J. Biol. Chem.*, 268, 26625-26633 (1993)).

Other binding assays employ fluorescent materials that are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture*, Part B, *Methods in Cell Biology*, vol. 30, ed. Taylor, D. L. & Wang, Y. L., San Diego: Academic Press, pp. 219-243 (1989); Turro, N. J., *Modern Molecular Photochemistry*, Menlo Park: Benjamin/Cummings Publishing Col, Inc. pp. 296-361 (1978).

Fluorescence in a sample can be measured using a fluorimeter, a fluorescent microscope or a fluorescent plate reader. In general, all of these systems have an excitation light source which can be manipulated to create a light source with a defined wavelength maxima and band width which passes through excitation optics to excite the sample.

Typically the excitation wavelength is designed to selectively excite the fluorescent sample within its excitation or absorption spectrum. For most FRET based assays the excitation wavelength is usually selected to enable efficient excitation of the donor while minimizing direct excitation of the acceptor. In response the sample (if fluorescent) emits radiation that has a wavelength that is different from the excitation wavelength. Collection optics then collect the emission from the sample, and direct it to one or more detectors, such as photomultiplier tubes or CCD cameras. Preferably the detector will include a filter to select specific wavelengths of light to monitor. For time resolved applications, for example time resolved FRET, the excitation and or emission optical paths include control mechanisms to precisely terminate illumination and then to wait for a precise period of time before collecting emitted light. By using compounds such as lanthanides that exhibit relatively long-lived light emission it is possible to gain significant enhancements in detection sensitivity and accuracy.

The detection devices can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, autofocusing feature, and electronics associated with imaging and data collection can be managed by an appropriately programmed digital computer. The computer also can transform the data collected during the assay into another format for presentation.

Suitable instrumentation for fluorescence microplate readers include without limitation the CytoFluor™ 4000 available from PerSeptive Biosystems. For 96-well based assays black walled plates with clear bottoms, such as those manufactured by Costar are preferred.

Suitable instrumentation for luminescence measurements include standard liquid scintillation plate readers, including without limitation the Wallac Microbeta, or PE Biosystems Northstar, or equivalents commercially available from Packard, Perkin Elmer and a number of other manufacturers.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a monomeric receptor, or a heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, a radiolabelled ligand such as tritiated $1\alpha,25$-dihydroxyvitamin $D_3$ (Amersham)) generates an optical signal when it is brought into close proximity to a scintillant such as a Ysi-copper containing bead, to which the VDR is bound. VDR can be prepared in CV-1 culture from pCMX-hVDR. The VDR containing CV-1 extract can then be incubated with anti-VDR rabbit antibody such that VDR will bind to the Yttrium SPA bead coated with anti-rabbit IgG through the antibody-antigen complex formation. The VDR and SPA bead mixture can then be incubated with both tritiated $1\alpha,25$-dihydroxyvitamin $D_3$ and the competing ligand of interest. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of a nuclear receptor can also be measured by fluorescence resonance energy transfer (FRET), or time resolved FRET, to monitor the ability of the compounds provided herein to bind to the nuclear receptor. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of lanthanide labeled streptavidin (Wallac Inc.), and the purified LBD of RXR, or alternate heterodimer, is labeled with a suitable fluorophore such as CY5™. Equimolar amounts of each modified LBD are mixed together and allowed to equilibrate for at least 1 hour prior to addition to either variable or constant concentrations of the test compound for which the activity is to be determined. After equilibration, the time-resolved fluorescent signal is quantitated using a fluorescent plate reader. The activity of the test compound can then be estimated from a plot of fluorescence versus concentration of test compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant epitope, or affinity tagged nuclear receptor ligand binding domain (LBD) fusion protein and a synthetic biotinylated peptide derived from the receptor interacting domain (-LXXLL motif) (SEQ ID NO: 1) of a co-activator peptide such as the steroid receptor coactivator 1 (SRC-1), TIF2, DRIP1 or AIB1. Typically the tagged-LBD is labeled with a lanthanide chelate such as europium (Eu), via the use of antibody specific for the tag, and the co-activator peptide is labeled with allophycocyanin via a streptavidin-biotin linkage.

In the presence of an agonist for the nuclear receptor, the peptide is recruited to the tagged-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit the activity of an agonist for the nuclear receptor.

In addition to the direct binding assays, a variety of cell based assay methodologies may be successfully used in screening assays to identify and profile the affinity of compounds of the present invention for VDR. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071,773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

In one embodiment of this method the host cell endogenously expresses the nuclear receptor heterodimer (typically with RXR) and appropriate co-factors. Typically such a situation may occur with a primary cell or cell lines derived directly from a primary cell type, is used to characterize compounds of the present invention. Accordingly creation of the assay system requires the transfection into the cell of a suitable reporter gene(s) as are described herein. Alternatively the expression of endogenous gene can be used to monitor VDR transcriptional activity in response to the addition of a test compound.

In another aspect the host cell may lack sufficient endogenous expression of a suitable nuclear receptor, in which case one may be introduced by transfection of the cell line with an expression plasmid, as described below.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or a fragment thereof, ligated to the promoter in sense orientation so that transcription from the promoter will produce a RNA that encodes a functional protein, and (3) a polyadenylation sequence. As an example not to be construed as a limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. *Genes & Development* 9:1033-1045(1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

In one aspect of these methods, full-length genes encoding the complete cDNA sequence of the vitamin D nuclear receptor can be used, these include, for example, human VDR (accession NM_005693), rat VDR (accession NP_033530), mouse VDR (accession AAH06716). Additionally VDR polymorphisms, such as those identified by restriction endonuclease digestion differences identified via differential susceptibility to the Fokl, Bsml, Apal and Taql restriction enzymes may also be useful for comparative analysis.

In another embodiment of these methods chimeras of these full-length genes are used in place of the full-length nuclear receptor. Such chimeras typically comprise the ligand binding domain (amino acids 235-422) of the VDR coupled to a heterologous DNA binding domain (DBD).

Typically for such chimeric constructs, heterologous DNA binding domains from distinct, well-defined nuclear receptors are used, for example including without limitation, the DBDs of the glucocorticoid receptor, GR (accession no. NM_000176)(amino acids 421-486), mineralocorticoid receptor, MR (accession no. NM_055775) (amino acids 603-668), androgen receptor, AR (accession no XM_010429_NM_055775) (amino acids 929-1004), progesterone receptor, PR (amino acids 622-695), and estrogen receptor alpha, ERα (accession no. XM_045967) (amino acids 185-250).

Alternatively DNA binding domains from yeast or bacterially derived transcriptional regulators such as members of the GAL 4 and Lex A (GenBank accession number ILEC)/ Umud super families may be used.

GAL4 (GenBank Accession Number P04386,) is a positive regulator for the expression of the galactose-induced genes. (see for example, Keegan et al., *Science* 231: 699-704 (1986)). Preferably the first 96 amino acids of the Gal4 protein are used, most preferably the first 147 amino acid residues of yeast Gal4 protein are used.

For those receptors that can function as heterodimers with RXR, such as the VDR, the method typically includes the use of expression plasmids for both the nuclear receptor of interest and RXR. Such sequences include, but are not limited to the following members of the RXR gene family, including RXRα; (GenBank Accession No. NM_002957), RXRβ, (GenBank Accession No. XM_042579) and RXRγ (GenBank Accession No. XM_053680).

To identify compounds that act to modulate co-factor, or nuclear receptor heterodimerization, a mammalian two-hybrid assay can be used (see, for example, U.S. Pat. Nos. 5,667,973, 5,283,173 and 5,468,614). This approach identifies protein-protein interactions in vivo through reconstitution of a strong transcriptional activator upon the interaction of two proteins, a "bait" and "prey" (Fields S and Song O *Nature* 340: 245 (1989); Willey et al., *Gene & Development* 9 1033-1045 (1995)).

This system relies on functional dimeric interactions between two fusion proteins, one carrying the GAL4 DNA-binding domain fusion with the ability to bind to a GAL4$_{UAS}$-containing reporter gene. The other carries the VP16 transactivation domain fusion. When expressed together, DNA binding and transcriptional activation is reconstituted in a single complex. Functional interaction, for example between a GAL-SRC-1 fusion protein and VP16-VDR fusion protein should lead to constitutive activation of a suitable reporter plasmid, such as luciferase reporter construct comprising GAL4 upstream Activating Sequences (UAS).

Such reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., *Mol. Cell. Biol.* 7 725-735 (1987)) down stream from the herpes virus thymidine kinase promoter (located at nucleotides residues-105 to +51 of the thymidine kinase nucleotide sequence, pBLCAT2 (Luckow & Schutz *Nucl. Acid. Res.* 15 5490-5494 (1987))) which is linked in turn to the appropriate response elements.

Transactivation domains are well known in the art and can be readily identified by the artisan. Examples include the GAL4 activation domain, TAT, VP16, and analogs thereof.

Response elements are well known and have been thoroughly described in the art. Such response elements can include direct repeat structures or inverted repeat structures based on well defined hexad half sites, as described in greater detail below. Exemplary hormone response elements are composed of at least one direct repeat of two or more half sites, separated by a spacer having in the range of 0 up to 6 nucleotides. The spacer nucleotides can be randomly selected from any one of A, C, G or T. Each half site of response elements contemplated for use in the practice of the invention comprises the sequence: -RGBNNM-, wherein R is selected from A or G; B is selected from G, C, or T; each N is independently selected from A, T, C, or G; and M is selected from A or C; is with the proviso that at least 4 nucleotides of said -RGBNNM- sequence are identical with the nucleotides at corresponding positions of the sequence -AGGTCA-. Response elements employed to profile the compounds of the present invention can optionally be preceded by N, wherein x falls in the range of 0 up to 5. Preferred response elements useful in the methods of the present invention include DR3 types response elements.

The choice of hormone response element is dependent upon the type of assay to be used. In the case of the use of the full length VDR a known VDR RE would typically be used. In the case of a VDR-LBD-Gal4 fusion, a GAL4 UAS would be used. Typically the GAL4 UAS would comprise the sequence 5' CGGRNNRCYNYNCNCCG-3' (SEQ ID NO: 2), where Y=C or T, R=A or G, and N=A, C, T or G, and would be present as a tandem repeat of 4 copies.

Numerous reporter gene systems are known in the art and include, for example, alkaline phosphatase (see, Berger, J., et al., *Gene*, 66, 1-10 (1988); and Kain, S. R., *Methods. Mol. Biol.* 63, 49-60 (1997)), β-galactosidase (See, U.S. Pat. No. 5,070,012, issued Dec. 3, 1991 to Nolan et al., and Bronstein, I., et al., *J. Chemilum. Biolum.* 4, 99-111 (1989)), chloramphenicol acetyltransferase (See, Gorman et al., *Mol. Cell Biol.* 21044-51 (1982)), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., *Annu. Rev. Biochem.* 67509-44 (1998)).

Numerous methods of co-transfecting the expression and reporter plasmids are known to those of skill in the art and may be used for the co-transfection assay to introduce the plasmids into a suitable cell type.

These screening approaches enable the selection of compounds that interaction with the VDR with high affinity. Preferably such compounds exhibit an affinity, as measured via any of the methods disclosed herein, of at least 500 nM, preferably at least 200 nM, more preferably at least 100 nM, and most preferably at least 20 nM.

Any compound which is a candidate for activation of VDR may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by VDR and other nuclear receptors in vivo, using Northern-blot, RT PCR or oligonucleotide microarray analysis to analyze RNA levels. Western-blot analysis can be used to measure expression of proteins encoded by VDR target genes. Genes that are known to be regulated by the VDR include without limitation IGF binding protein-3 (IGFBP-3), calbindin-D(28 k), calbindin-D(9 k), 25(OH)D(3) 24-hydroxylase and CCAAT enhancer binding protein beta (C/EBPbeta), osteocalcin, osteopontin, NF-kβ ligand (RANKL).

All methods discussed thus far may be adapted for use in high throughput screening. High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., *Biomol. Screen*, 5, No. 5, 297 (2000)), scintillation proximity assays (SPA) (see, for example, Carpenter et al., *Methods Mol. Biol.* 190, 31-49 (2002)) and fluorescence resonance energy transfer energy transfer (FRET) or time resolved FRET based coactivator recruitment assays (Mukherjee et al., *J. Steroid Biochem. Mol. Biol.* 81, No. 3, 217-25 (2002); (Zhou et al., *Mol. Endocrinol.* 12, No. 10, pp. 1594-604 (1998)).

Established animal models exist for a number of diseases of direct relevance to the claimed compounds and these can be used to further profile and characterize the claimed compounds. These model systems include Zucker (fa/fa) rats or (db/db) mice for studying diabetic dyslipidemia, nude mice transplanted with tumor cells for tumor growth studies, non-obese diabetic mouse (NOD) for type-1 diabetes studies and ovariectimized rats (OVX) for osteoporosis studies.

Additionally VDR animal models (e.g., knockout mice) can be used to further evaluate the present compounds and compositions in vivo (see, for example, Li et al *Proc. Natl. Acad. Sci. USA* 94, 9831-9835 1997)

E. Formulation of Pharmaceutical Compositions

The pharmaceutical compositions provided herein contain therapeutically effective amounts of one or more of the compounds or compositions, or pharmaceutically acceptable derivatives thereof, provided herein that are useful in the prevention, treatment, or amelioration of human and veterinary diseases, disorders and conditions mediated by, or otherwise affected by the vitamin D receptor, or in which VDR activity, is implicated, as defined herein.

The compounds, compositions, or pharmaceutically acceptable derivatives thereof are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms*, Fourth Edition 1985, 126; Remington's Pharmaceutical Sciences, Mack Publishing Company, Easton, Pa., 15th Edition, 1975).

In the pharmaceutical compositions, effective concentrations of one or more compounds or pharmaceutically acceptable derivatives thereof is (are) mixed with at least one suitable pharmaceutical carrier, vehicle, diluent, or solvent. Dosage forms or compositions containing active ingredient in the range of 0.005% to 100% with the balance made up from non-toxic carrier may be prepared. The contemplated compositions may contain 0.001%-100% active ingredient, preferably 0.1-85%, typically 75-95%. In addition, the compounds may be formulated as the sole pharmaceutically active ingredient in the composition or may be combined with other active ingredients.

The active compound is included in the pharmaceutically acceptable carrier in an amount sufficient to exert a therapeutically useful effect in the absence of undesirable side effects on the patient treated. The therapeutically effective concentration may be determined empirically by testing the compounds using in vitro and in vivo systems described herein and in International Patent Application Publication Nos. 99/27365 and 00/25134 and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time by a suitable route, including orally, parenterally, rectally, topically and locally. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses that are not segregated in packaging.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, celluloses, polyvinyl pyrrolidone, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol, carboxymethylcellulose and dicalcium phosphate. Glidants include, but are not limited to, colloidal silicon dioxide. Disintegrating agents include croscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether.

In all embodiments, tablets and capsules formulations may be coated as known by those of skill in the art in order to modify or sustain dissolution of the active ingredient. If oral administration is desired, the compound could be provided in a composition that protects it from the acidic environment of the stomach. Thus, for example, they may be coated with a conventional enterically digestible coating, such as phenylsalicylate, waxes and cellulose acetate phthalate. Emetic-coatings also include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active ingredient can also be mixed with other materials which do not impair the desired action, or with materials that supplement the desired action, such as antacids, H2 blockers, and diuretics. The active ingredient is a compound or pharmaceutically acceptable derivative thereof as described herein.

Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, generally characterized by injection, either subcutaneously, intramuscularly or intravenously is also contemplated herein. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Sustained Release Formulations

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Compositions for other Routes of Administration

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010,715; 5,985,317; 5,983,134; 5,948,433; and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated corn pound, pelleted by centrifugation, and then resuspended in PBS.

Articles of Manufacture

The compounds or pharmaceutically acceptable derivatives may be packaged as articles of manufacture comprising packaging material, a compound or composition, or pharmaceutically acceptable derivative thereof provided herein, and a label that indicates that the compound or composition, or pharmaceutically acceptable derivative thereof, is used for modulating the activity of a steroid nuclear receptor, or for treatment, prevention or amelioration of one or more symptoms of a steroid nuclear receptor mediated diseases or disorder, or diseases or disorders in which steroid nuclear activity is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

F. Methods of Treatment and Combination Therapy

The present compounds and compositions are intended for use in pharmaceutical compositions which are useful in the local or systemic treatment or prophylaxis of human and veterinary disorders and disease, including without limitation, (a) skin tissue function, including hyperproliferative skin diseases, such as psoriasis (including pustulosis palmoplantaris, acrodermatitis continua and nail psoriasis), disturbances of keratinization and keratosis, such as atopic dermatitis, eczema, rosacea, actinic keratosis, atrophic skin, skin aging, medicinally induced skin atrophy, wound healing and congenital keratinization disorders, disorders of sebaceous glands such as, acne, sebonheic dermatitis, (U.S. Pat. Nos. 4,728,643 and 5,037,816), disorders related to disrupted hair growth such as androgenetic alopecia, alopecia areata/totalis, and chemotherapy —induced alopecia;

(b) cancer, including cancer initiation, progression and cancer associated angiogenesis and metastasis. Specific cancers include without limitation, cancers of the breast, (*J. NCI* 89:212-218, (1997); *Lancet* 1: 188-191, (1989)); colon, (Lointier et al., *Anticancer Res.* 7:817-822, (1987), Niendorf, et al., *J. Steroid Biochem.* 27:815-828, (1987), Tanaka et al., *Arch. Biochem. Biophys.* 276: 415-423, (1990), Halline et al., *Endocrinology* 134:1710-1717, (1994)); prostrate, including benign prostatic hypertrophy, (*Urology* 46:365-369, (1994)); brain glial tumours, (Baudet, C. et al., *Cancer Lett.*, 100, 3 (1996)); squamous cell carcinoma, (*Molecular and Cellular Differentiation* 3: 31-50, (1995)); ovarian cancer, (U.S. Pat. Nos. 6,444,658, 6,407,082); myeloid leukemia, (*Blood* 74:82-93, (1989), *Proc. Natl. Acad. Sci* USA 80: 201-204, (1983), U.S. Pat. No. 4,391,802); osteosarcoma; adenocarcinomas of the lung, and pancreas, transitional cell carcinoma of the bladder, myelofibrosis, and melanoma;

(c) diseases of, or imbalances in, the immune system, such as host versus graft and graft versus host reactions, transplant rejection, (U.S. Pat. No. 4,749,710) and autoimmune and inflammatory diseases, including without limitation, discoid and systemic lupus erythematosus, type I diabetes mellitus, (C. Mathieu, et al., *Diabetologia* 37:552-558, (1994), U.S. Pat. No. 5,665,387); multiple sclerosis, (U.S. Pat. No. 6,479, 474); chronic dermatoses of auto-immune type, e.g. scleroderma and pemphigus vulgaris, and inflammatory diseases, such as intestinal bowel disease (U.S. Pat. No. 6,358,939), asthma, (U.S. Pat. No. 6,603,031); rheumatoid arthritis, (U.S. Pat. No. 4,743,596) and cognitive impairment or senile dementia (Alzheimers disease), (U.S. Pat. No. 6,573,255);

(d) diseases related to the hormonal and metabolic regulatory functions of vitamin D on calcium homeostasis including without limitation hyperparathyroidism, (U.S. Pat. No. 6,376,479); chronic kidney disease (Friedman and Norris, *Trends Endo. & Met.* 13 (5) 189-194 (2002)) and osteoporosis, (U.S. Pat. No. 6,150,346).

Skin Tissue Function $1\alpha,25$-dihydroxyvitamin $D_3$ plays a vital role in skin-tissue function through its effects on proliferation and the differentiation of keratinocytes (U.S. Pat. No. 6,603,031). Additionally $1\alpha,25$-dihydroxyvitamin $D_3$ acts to suppress the activation and proliferation of inflammatory T-cells thereby inhibiting the production of inflammatory mediators that contribute to the pathogenesis of psoriasis and related disorders.

Accordingly, in one aspect the present invention also provides a method of preventing the occurrence of, or treating a subject suffering from, a disorder of skin tissue function associated with the proliferation and or differentiation of keratinocytes, in which any compound or composition of the present invention is administered to the subject in need of such treatment.

In one aspect, the invention further provides a method of preventing the occurrence of, or treating a subject suffering from psoriasis, acne, atopic dermatitis, eczema, rosacea, actinic keratosis, seborrheic dermatitis, and congenital keratinization disorders in which any compound or composition of the present invention is administered to the subject in need of such treatment. In one aspect of treatment, a compound or composition of the present invention is topically administered to the subject.

In another aspect the present invention further provides a method of preventing the occurrence of, or treating a subject suffering from atrophic skin due to natural skin aging, light exposure, or medicinally-induced skin atrophy by treatment with glucocorticoids, by application of any of the claimed compounds or compositions to the subject in need of such treatment. In one aspect of treatment a compound or composition of the present invention is topically administered to the subject.

In another aspect the present invention further provides a method of accelerating wound healing by topical application of the claimed compounds or compositions to the subject in need of such treatment.

From clinical observations, it is known that alopecia often accompanies vitamin $D_3$-resistant rickets, which develops in early infancy suggesting a role for $1\alpha,25$-dihydroxyvitamin $D_3$ in the regulation of hair growth.

Accordingly, the present invention thus also provides methods for the treatment of diseases which accompany disrupted hair growth (androgenetic alopecia, alopecia areata/totalis, chemotherapy-induced alopecia) or for supporting physiological hair growth without causing the side-effects of calcitriol (especially hypercalcemia), comprising applying to the affected areas of the skin any compound or composition of the present invention.

Cancer

Studies in animals have shown that certain $1\alpha,25$-dihydroxyvitamin $D_3$ compounds and analogues are potent inhibitors of malignant cell proliferation and are inducers/stimulators of cell differentiation and, or, apoptosis. Additionally evidence exists to support the proposition that $1\alpha,25$-dihydroxyvitamin $D_3$ plays a role in the prevention of cancer progression, inhibits cancer-induced angiogenesis (Circulation Research, 4: 214-220 (2000)) and can act to inhibit cancer metastasis (Hansen C. M. et al. In: *Vitamin D, Proceedings of the Ninth Workshop on Vitamin D, Orlando, Fla., Walter de Gruyter, Berlin* 508-509 (1994)) and is effective in treating benign prostatic hypertrophy, (*Urology* 46: 365-369 (1994)).

Accordingly the present invention also provides methods for the treatment or prevention of cancer, including cancer initiation, progression and cancer associated angiogenesis, metastasis and invasion. In one aspect of these methods of treatment or prevention, the claimed compounds and compositions produce a reduced hypercalcemic effect compared to the same dose of $1\alpha,25$-dihydroxyvitamin $D_3$. In one aspect the cancer is selected from the group consisting breast cancer, colon cancer, prostrate cancer, brain glial tumors, squamous cell carcinoma, ovarian cancer, myeloid leukemia, osteosarcoma; adenocarcinomas of the lung, and pancreas, transitional cell carcinoma of the bladder, myelofibrosis; and melanoma.

Cancer Prevention

Cancer prevention strategies may be divided into three categories primary, secondary, and tertiary, depending on where in the carcinogenic process the preventive measure is supposed to intervene (Bertram et al. *Cancer Res.* 47:3012-3031, (1987)). Primary prevention effects the initiation of carcinogenesis and represents the very first step intervention may occur. If the carcinogenic process has already begun and an attempt is made to interrupt it by decreasing cancer promotion, it may be termed secondary prevention. The subjects in primary and secondary prevention trials do not have detectable lesions, although they may be chosen to be at high risk for developing cancer. After precancerous lesions are present, tertiary prevention may begin, which goal is to alter these lesions either by making them regress or disappear, or by preventing their development into cancer.

Accordingly the present invention also provides a primary prevention strategy to prevent or avert the initiation of carcinogenesis in a subject by administering a sufficient amount of any compound or composition of the present invention to the subject. In one aspect of the strategy, the claimed compounds and compositions produce a reduced hypercalcemic effect compared to the same dose of $1\alpha,25$-dihydroxyvitamin $D_3$. In a preferred embodiment the cancer to be prevented is selected from the group consisting of breast cancer, colon cancer, prostrate cancer, brain glial tumors, squamous cell carcinoma, ovarian cancer, myeloid leukemia, osteosarcoma; adenocarcinomas of the lung, and pancreas, transitional cell carcinoma of the bladder, myelofibrosis; and melanoma.

In another embodiment, the present invention also provides a secondary prevention strategy to prevent or avert cancer promotion in a subject by administering a sufficient amount of any compound or composition of the present invention to the subject. In one aspect of the strategy the claimed compounds and compositions produce a reduced hypercalcemic effect compared to the same dose of 1α,25-dihydroxyvitamin $D_3$. In a preferred embodiment the cancer to be prevented is selected from the group consisting of breast cancer, colon cancer, prostrate cancer, brain glial tumors, squamous cell carcinoma, ovarian cancer, myeloid leukemia, osteosarcoma; adenocarcinomas of the lung, and pancreas, transitional cell carcinoma of the bladder, myelofibrosis; and melanoma.

In another embodiment, the present invention also provides a tertiary prevention strategy to cause lesion regression or disappearance in a subject by administering a sufficient amount of any composition of the present invention to the subject. In one aspect of the strategy, the claimed compounds and compositions produce a reduced hypercalcemia compared to the same dose of 1α,25-dihydroxyvitamin $D_3$. In a preferred embodiment the cancer to be prevented is selected from the group consisting of breast cancer, colon cancer, prostrate cancer, brain glial tumors, squamous cell carcinoma, ovarian cancer, myeloid leukemia, osteosarcoma; adenocarcinomas of the lung, and pancreas, transitional cell carcinoma of the bladder, myelofibrosis; and melanoma.

Cancer Treatment

The ability of 1α,25-dihydroxyvitamin $D_3$ to regulate cell growth and differentiation has been well established in many systems including (but not limited to) prostate (reviewed in Johnson et al., *Cancer & Metastasis*) 21:147-158 (2002), breast (Colston et al., *Biochem Pharmacol* 44: 693-702 (1992); Colston and Hansen, *Endocr Relat Cancer* 9:45-59 (2002)), colon (Shabahang et al., *Cancer Research*) 54 (15): 4057-4064 (1994), pancreas (;Zugmaier et al., *Br J Cancer* 73:1341-1346 (1996), myeloid leukemia (Mangelsdorf et al., *J Cell Biol.* 98 (2):391-8 (1984), Zhou et al., *Proc. Natl. Acad. Sci* USA) 87: 3929-3932 (1990)), human carcinoma cells (Hansen et al., In: *Vitamin D, Proceedings of the Ninth Workshop on Vitamin D*, Orlando, Fla., (1994) pp. 508-509). and melanoma (Colston et al., *Endocrinology* 108 (3) 1083-6 (1981)). It has been shown that vitamin D inhibits cancer cell growth by arresting cell cycle progression in the G0/G1 phase (Colston and Hansen *Endocr. Relat. Cancer* 9 (1) 45-59 (2002)). Research has shown that VDR regulates cell cycle related genes such as the cyclin dependent kinase inhibitors p21 and p27 (Liu et al., *Genes & Dev* 10:142-153 (1996), Muto et al., *Blood* 93: 2225-2233 (1999)), Wang et al., *Cancer Res* 57: 2851-2855 (1997).

Vitamin D is also believed to have inhibitory effects on growth factors such as retinoblastoma protein and insulin-like growth factor binding protein-3 (IGFBP-3), and therefore may play a role in interfering with malignant cell growth (Boyle et al. *J Urol* 165: 1319-1324 (2001)). It has also been shown that vitamin D compounds can halt cell growth by inducing apoptosis in a number of different cancer cell types, with one likely mechanism being the down regulation of the anti-apoptotic factor Bcl-2 by vitamin D and its analogs (Blutt et al. *Endocrinology* 141:10-17 (2000)).

Accordingly the present invention also provides a method to inhibit cancer invasion or metastasis in a subject by administering a sufficient amount of any compound or composition of the present invention to the subject. In one aspect of the method, the claimed compounds and compositions produce a reduced hypercalcemic effect compared to the same dose of 1α,25-dihydroxyvitamin $D_3$. In a preferred embodiment the cancer to be prevented is selected from the group consisting of breast cancer, colon cancer, prostrate cancer, brain glial tumors, squamous cell carcinoma, ovarian cancer, myeloid leukemia, osteosarcoma; adenocarcinomas of the lung, and pancreas, transitional cell carcinoma of the bladder, myelofibrosis, and melanoma.

In another aspect of the invention, the present invention provides a method of inducing apoptosis in a cell by administering to a subject an effective amount of any of the claimed compositions to the subject.

Diseases of, or Imbalances in, the Immune System

Vitamin D is produced in activated macrophages and is a significant regulator of the immune system, where it plays a key role in moderating inflammatory responses. Recent studies suggest that VDR promotes $CD4^+$ T helper 2 cell mediated antibody responses to cutaneous antigens, and plays a role in the establishment and or maintenance of immunological self tolerance (Hayes et al. *Cell. Mol. Biol.* 49 (2): 277-300 (2003)).

Accordingly, the present invention provides a method of preventing the development of, or reducing an inflammatory, immune or autoimmune response in a subject by administering to the subject in need of such treatment any compound or composition of the present invention. In one aspect of the method, the claimed compounds and compositions produce a reduced hypercalcemic effect compared to the same dose of 1α,25-dihydroxyvitamin $D_3$. Preferably the inflammatory immune or autoimmune response is selected from arthritis, intestinal bowel disease, type I diabetes, asthma, lupus, transplantation rejection and multiple sclerosis.

Arthritis relates generally to a class of disorders characterized by inflammation of joints, significant members of this class being rheumatoid arthritis and osteoarthritis. Rheumatoid arthritis (RA) is a chronic syndrome characterized by nonspecific, usually symmetric inflammation of the peripheral joints, potentially resulting in progressive destruction of articular and periarticular structures. Osteoarthritis (OA) is the most common form of arthritis and is characterized by degenerative loss of articular cartilage, subchondral bony sclerosis, cartilege and bone proliferation at the joint margins with subsequent osteophyte formation and, commonly, secondary synovial inflammation.

Accordingly, the present invention also provides a method of treating or preventing arthritis in a subject by administering to the subject in need of such treatment any compound or composition of the present invention. Intestinal Bowel Disease (IBD) encompasses both Crohn's Disease (CD) and Ulcerative Colitis (UC), which are distinct, but related polygenic disorders. Recently, an IBD susceptibility locus was mapped to the same region as the vitamin D receptor and the 25-hydroxyvitamin $D_3$-1-a-hydroxylase genes (Labuda et al., *J. Bone Min. Res.* 7:1447-53 (1992)). Accordingly it is believed that there may be a genetic defect in calcitriol synthesis, transport, or utilization which underlies a dual phenotype of decreased bone mineralization and susceptibility to IBD in some individuals. As such, the therapeutic affect of the administration of 1α,25-dihydroxyvitamin $D_3$ to patients may be achieved (at least in part) by compensating for these genetic defects.

Accordingly, the present invention also provides a method of treating or preventing intestinal bowel disease in a subject by administering to the subject in need of such treatment any compound or composition of the present invention. In one aspect of the method, the claimed compounds and compositions do not cause, or are administered to eliminate or reduce, the occurrence of hypercalcemia.

Type I Diabetes

Type I diabetes is characterized by hyperglycemia (fasting blood sugar greater than 140 mg/dl), increased thirst and urine production, increased cholesterol in the blood, and increased blood triglyceride concentration. Type I diabetes is believed to have an autoimmune origin, and is not usually associated with obesity. A patient at risk of developing type I diabetes is someone with a family history of developing type I diabetes or an individual that is identified to possess circulating antibodies to insulin or pancreatic cells, or who exhibits elevated fasting blood sugar levels.

The non-obese diabetic (NOD) mouse is used as a model of human Type I diabetes because destruction of the islet cells occurs via an autoimmune reaction in both systems. Development of Type I diabetes in the NOD mouse is T-cell mediated, involving the participation of both CD8$^+$ and CD4$^+$ cells (Wicker et al., *Annu. Rev. Immunol.* 13:179-200 (1995)). In this model, 70-80% of chow-fed NOD females develop diabetes and 20% of chow-fed males develop the disease (Makino et al., *Exp. Anim.* 30:137-140 (1981)). In this model system, administration of 1α,25-dihydroxyvitamin $D_3$ reduced the incidence, and delayed the onset, of diabetes in female NOD mice (Mathieu et al., *Diabetologia* 37:552-558 (1994)).

Accordingly in one embodiment, the present invention includes a method of delaying the onset of diabetes in a human patient, comprising the step of administering to a patient at risk of developing type I diabetes, an effective amount of any of the compounds or compositions of the present invention such that the onset of diabetes or diabetic symptoms (i.e. hyperglycemia) is slowed or eliminated. In one aspect of the method, the claimed compounds and compositions produce a reduced hypercalcemic effect compared to the same dose of 1α,25-dihydroxyvitamin $D_3$.

In another embodiment the present invention is a method of reducing the severity of diabetes symptoms comprising administering to a human type I diabetes patient an effective amount of any of the compounds or compositions of the present invention such that diabetes symptoms (i.e. hyperglycemia) are lessened. In one aspect of the method, the claimed compounds and compositions do not cause, or are administered to eliminate or reduce, the occurrence of hypercalcemia.

Hyperparathyroidism

The disease of hyperparathyroidism is a generalized disorder resulting from excessive secretion of parathyroid hormone by one or more parathyroid glands. The disease is characterized by elevated blood parathyroid hormone levels, and parathyroid glandular enlargement which can lead to abnormal calcium, phosphorus and bone metabolism, eventually resulting in high bone turnover, bone loss, mineralization defects, hip and other fractures.

Hyperparathyroidism is subcategorized into primary, secondary and tertiary hyperparathyroidism. In primary hyperparathyroidism, the growth of the parathyroid glands is autonomous in nature, and is usually due to tumors, e.g., parathyroid adenomas. Secondary hyperparathyroidism, is associated, with 1,25-dihydroxyvitamin $D_3$ deficiency and/or resistance, and typically occurs in patients, e.g., with renal failure, osteomalacia, and intestinal malabsorption syndrome. Tertiary hyperparathyroidism is characterized by an autonomous proliferation state of the parathyroid glands with biological hyperfunction. Tertiary hyperparathyroidism can occur in patients with secondary hyperparathyroidism, wherein the reversible hyperplasia associated with secondary hyperparathyroidism converts to an irreversible growth defect, the enlarged tissue having vitamin D receptors. In all forms of hyperparathyroidism, bone abnormalities, e.g., the loss of bone mass or decreased mineral content, are common and renal damage is possible.

Accordingly the present invention also provides a method of treating or preventing hyperparathyroidism in a subject by administering a sufficient amount of any compound or composition of the present invention to the subject. Preferably the hyperparathyroidism is secondary hyperparathyroidism associated with vitamin D deficiency.

Osteoporosis

Osteoporosis is a generic description for a group of diverse diseases which are characterized by a reduction in the mass of bone per unit volume with a histologically normal ratio of osteoid to bone. The effects of these diseases are particularly severe when the mass per unit volume decreases to a level below that required for adequate mechanical support. Osteoporosis is a particularly important cause of morbidity in the elderly. The most frequent symptoms are back pain and deformity of the spine resulting from a collapse of the vertebrae, especially in the lumbar and thoracic spine regions.

Because vitamin D plays an important role in bone metabolism, it has been the subject of research for the treatment of osteoporosis. Vitamin D analogs that have been developed for the treatment of osteoporosis include 1α,25-dihydroxy-2beta-(3-hydroxypropoxy)vitamin D3 (known as ED-71, developed by Chugai Pharmaceuticals) and 2-methylene-19-nor-(20S)-1α,25-dihydroxyvitamin $D_3$ (known as 2MD, developed by Wisconsin Alumni Research Foundation). 2MD has been shown to be a highly potent and bone-specific vitamin D analog which stimulates osteoblast-mediated bone calcium mobilization to a greater extent than intestinal calcium transport (deLuca et al., PNAS (2002) 99(21):13487-13491. Currently undergoing human clinical trial is ED-71, which has been shown to increase bone mass in the ovariectomized rat model (Tsurukami *Calcif Tissue Int* 54:142-149 (1994). More traditional agents used for the prevention and treatment of bone loss and osteoporosis include e.g. estrogen, 1α,25-dihydroxyvitamin $D_3$ and bisphosphonates, such as alendronate (for a review, see: *Osteoporosis* (Marcus, R., Feldman, D. and Kelsey, F., Eds.) Academic Press, San Diego, 1996).

In another aspect, the present compounds and compositions are intended to treat, or prevent the occurrence of all diseases classified as osteoporosis, particularly post-menopausal osteoporosis, senile osteoporosis, idiopathic osteoporosis, immobilization osteoporosis, post-partum osteoporosis, juvenile osteoporosis, and osteoporosis secondary to gonadal insufficiency, malnutrition, hyperprolactinemia, prolactinoma, disorders of the gastrointestinal tract, liver, or kidneys, and osteoporosis that is a sequella of prior osteomalacia, chronic acidosis, thyrotoxicosis, hyperparathyroidism, glucocorticoid excess or chronic disorders involving the bone marrow, and heritable forms of osteoporosis such as osteogenesis imperfecta and its variants, and other heritable disorders of connective tissue.

Combination and Pulsatile Therapies

In another embodiment, the claimed compounds and compositions may be administered to the subject as a therapeutically effective pulsed dose of the compound or composition in a sufficient amount to have a therapeutic effect, without inducing hypercalcemia, particularly symptomatic hypercalcemia, as set forth for in Examples 1, 2, 3 and 4 of the written description in U.S. Pat. No. 6,521,608, (which is hereby incorporated by reference).

"Hypercalcemia" refers to a calcium plasma concentration greater than the normal range for example greater than about 10.5 mg/dL in humans. Hypercalcemia can be broken into various grades, as set in column 6, second and third full paragraphs and Appendix II of U.S. Pat. No. 6,521,608, (which is hereby incorporated by reference).

"Symptomatic hypercalcemia" refers to hypercalcemia associated with one of more of the signs or symptoms of hypercalcemia. Early manifestations of hypercalcemia include weakness, headache, somnolence, nausea, vomiting, dry mouth, constipation, muscle pain, bone pain, or metallic taste. Late manifestations include polydypsia, polyuria, weight loss, pancreatitis, photophobia, pruritis, renal dysfunction, aminotransferase elevation, hypertension, cardiac arrhythmias, psychosis, stupor, or coma.

A "pulse" dose refers to administration of the drug in a sufficient amount to increase the blood or tissue level of the D drug to a supraphysiologic concentration for a sufficient period of time to have a therapeutic benefit, but with a sufficient period between doses to avoid hypercalcemia, given the pharmacological half life of the drug, its rate of elimination from the body, and its calcemic index.

Briefly in such a method the patient is placed and maintained on a reduced calcium diet prior to treatment, to help minimize intestinal absorption and allow maximal doses of the compounds and compositions to be used. Typically the diet is designed to restrict daily calcium intake to 400-500 mg, and promote adequate oral hydration by requiring the subject to drink additional water.

Baseline laboratory tests are typically initiated to determine serum levels of calcium, phosphate, and $1\alpha,25$-dihydroxyvitamin $D_3$ and subjects are treated with the once a week pulse dose of the claimed compounds until disease progression or 4 weeks, whichever comes first, and are followed for 2 months from enrollment. If significant toxicity is encountered, the treatment is stopped. The subject is monitored daily for symptoms of hypercalcemia for at least 2-3 days following administration. The patient may have a variety of laboratory tests performed to monitor the presence of hypercalcemia, or any physiological consequences of hypercalcemia. Such tests may include calcium at 0, 24, 48 hours, and baseline levels of creatinine, total billirubin, ALT, alkaline phosphatase, and a complete blood count. Other possible laboratory tests include phosphate, $1\alpha,25$-dihydroxyvitamin $D_3$ levels at 0, 6, 24, 48 hours, and 24 hour urine collection for calcium and hydroxyproline on day 2.

An initial dose may be chosen from safe doses documented in the literature, or animal studies, followed by a multistage escalation scheme, such as the one described by Gordon and Willson (Statistic in Medicine 11:2063-2075, 1992).

In the case of $1\alpha,25$-dihydroxyvitamin $D_3$ for example, the pulse dose may be given to each subject weekly, and the subject monitored for early signs and symptoms of hypercalcemia, such as weakness, headache, somnolence, nausea, vomiting, dry mouth, constipation, muscle pain, bone pain, metallic taste. The patient may also be monitored for any more serious manifestations, such as polydypsia, polyuria, weight loss, pancreatitis, photophobia, pruritis, renal dysfunction, aminotransferase elevation, hypertension, cardiac arrhythmias, psychosis, stupor, coma, and ectopic calcification. Appropriate treatment is instituted for any patient who demonstrates hypercalcemic toxicity, and treatment is stopped until serum calcium returns to normal.

Combination Therapy for the Treatment of Cancer

There are promising reports of co-treatment of vitamin D analogs with other anticancer drugs resulting in a dramatic increase of anti-tumor activity (reviewed in Johnson et al., *Clinical Cancer Research* 7:4164-4173 (2001)). Additionally, combination with the glucocorticoid dexamethasone demonstrates a synergistic effect on inhibiting proliferation and inducing apoptosis of prostate cancer cells while reducing the hypercalcemia of $1\alpha,25$-dihydroxyvitamin $D_3$ (Yu et al., *J. Natl. Acad. Inst.* 21 90 (2) 134-41 (1998)). These studies have been extended to clinical trials for metastatic androgen-independent prostate cancer (AIPC) in which high dose calcitriol (oral $1\alpha,25$-dihydroxyvitamin $D_3$) is administered weekly with docetaxel for 6 weeks. The results of this trial indicated an enhanced response to the combination therapy when compared to docetaxel alone (Beer et al., *Journal of Clinical Oncology*, 21(1): 123-128 (2003)).

For treatment for malignant conditions in accordance with the present Invention, a compound or composition of the present invention is suitably administered alone as an active ingredient in a pharmaceutical composition, or is co-administered with an anticancer agent. In certain embodiments a composition of the present invention and the anticancer agent are part of a single therapeutic composition (e.g. such that the administration may be accomplished with a single composition). In other embodiments, a composition of the present invention and the anticancer agent are separate compositions (e.g. such that each composition may be administered separately to the subject). In preferred embodiments, a composition of the present invention and the anticancer agent are administered to the subject at about the same time (e.g., within a few seconds, minutes, or hours of each other).

Further, included within the scope of the present invention is the co-administration of a compound or composition of the present invention with an anticancer agent. Such agents suitably include anti-metabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, Cl-973), anthracyclines (e.g., doxrubicin, daunorubicin), antibiotics (e.g., mitomycin, idarubicin, adriamycin, daunomycin), topoisomerase inhibitiors (e.g., etoposide, camptothecins) or any other cytotoxic agents, (estramustine phosphate, prednimustine), hormones or agents acting on nuclear hormone receptors (steroids and anti-steroids, estrogens, anti-estrogens, androgens, anti-androgens, glucocorticoids, dexamethasone, etc.).

Another example of combination therapy claimed herein is the co-administration of the claimed compounds or compositions provided herein with radiation therapy in the treatment of prostate cancer. (Dunlap et al., *British Journal of Cancer* 89:746-753 (2003)).

It is anticipated that a compound or composition of the present invention used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

In another aspect, the invention is a pharmaceutical composition which includes an anticancer agent which is a compound or composition of the present invention; an agent selected from the group consisting of (i) an anticancer agent, (ii) a bone agent, and combinations thereof; and a physiologically acceptable carrier.

Also included within the scope of the present invention is the co-administration of effective dosages of any of the claimed compounds or compositions in conjunction with administration of nuclear receptor ligands, or other agents, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron.

Antiestrogens, such as Tamoxifen™, are also known bone agents and may be suitably used in conjunction with the compounds and compositions of the present invention.

Combination Therapy for Immunosuppression

In particular embodiments, the present invention provides methods for treatment, comprising: a) providing: i) a subject with symptoms of at least one $1\alpha,25$-dihydroxyvitamin $D_3$ responsive disease, ii) a compound or composition of the present invention, and iii) an anti-autoimmune agent; and b) administering a therapeutically effective amount of a composition of the present invention, and a therapeutically effective amount of the an anti-autoimmune agent, to the subject under conditions such that the symptoms are reduced.

Anti-autoimmune agents include without limitation interleukin-10, interleukin-4, TNFα inhibitors, immunosuppressive drugs such as cyclosporin A and anti-inflammatory drugs such as non-steroidal anti-inflammatory drugs (NSAIDs) and steroids.

In another embodiment, the present invention provides methods for treatment, comprising: a) providing: i) a subject with symptoms of at least one $1\alpha,25$-dihydroxyvitamin $D_3$ responsive disease, ii) a compound or composition of the present invention, and iii) interleukin-4; and b) administering a therapeutically effective amount of a composition of the present invention, and a therapeutically effective amount of the interleukin-4, to the subject under conditions such that the symptoms are reduced.

In certain embodiments a composition of the present invention and the interleukin-4 are part of a single therapeutic composition (e.g. such that the administration may be accomplished with a single composition). In other embodiments, a composition of the present invention and interleukin-4 are separate compositions (e.g. such that each composition may be administered separately to the subject). In preferred embodiments, a composition of the present invention and the interleukin-4 are administered to the subject at about the same time (e.g., within a few seconds, minutes, or hours of each other).

In certain embodiments, the present invention provides methods of treatment comprising: a) providing; i) a subject at risk for at least one $1\alpha,25$-dihydroxyvitamin $D_3$ responsive disease, ii) a compound or composition of the present invention, and iii) an anti-autoimmune agent; and b) prophylactically administering the composition of the present invention and the an anti-autoimmune agent to the subject.

Combination Therapy for the Treatment of Osteoporosis

The present invention also comprises a combination therapy for the administration, to a human afflicted with osteoporosis, comprising a combination of a parathyroid hormone (PTH) or physiologically active fragment thereof, (hPTHF 1-34) for example with any of the compounds or compositions claimed herein.

In another embodiment the combination therapy further comprises a dietary calcium supplement and any of the compounds or compositions claimed herein. The invention also comprises pharmaceutical compositions intended for use in this method.

In certain embodiments a compound or composition of the present invention and the parathyroid hormone or calcium supplement are part of a single therapeutic composition (e.g. such that the administration may be accomplished with a single composition). In other embodiments, a compound or composition of the present invention and the parathyroid hormone or calcium supplement are separate compositions (e.g. such that each composition may be administered separately to the subject). In preferred embodiments, a composition of the present invention and the parathyroid hormone or calcium supplement are administered to the subject at about the same time (e.g., within a few seconds, minutes, or hours of each other).

Ranges of administration of parathyroid hormone hPTHF 1-34, may be used, for example, 100-700 units/day, more preferably 200-600 units/day, and most preferably 400-500 units/day, wherein "units" are defined in terms of the International Reference Preparation of hPTHF 1-34 and comparative bioassays in one of the established PTH bioassays. Potency ratios of different PTH analogues differ in different assays. The "units" are expressed in the chick hypercalcemic assay For other PTHF molecules, the ranges of administration are those high enough to stimulate bone remodeling in humans, yet not so high as to produce net bone resorption nor enough bone mineral mobilization to produce hypercalcemia or hypercalciuria. For compounds other than hPTH 1-34, dosage can be quantitated on a weight basis, or in terms of an appropriately established reference standard.

By "dietary calcium supplement" as used in this invention is meant supplementing the normal diet with calcium at a level greater than that level which is recommended as the daily dietary allowance. Accordingly, a dietary calcium supplement for an adult would involve the administration of sufficient calcium to increase the total oral intake of diet plus supplement to 38-50 millimoles/day. When a dietary calcium supplement is used, the calcium is administered in a non-toxic form. The dosage rates mentioned herein refer to the amounts of calcium present, and the dosage rate of the actual compound used can be easily calculated therefrom using the formula weight of the compound being administered. Milk or any non-toxic salt of calcium may be utilized provided that the counter ion is not toxic to the human in which it is being administered. Typical suitable non-toxic counter ions include carbonate, citrate, phosphate, gluconate, lactate, chloride, and glycerol phosphate. The upper limit of the dietary calcium supplement is determined by the toxic effects of calcium, which varies slightly from patient to patient, as is well understood by those skilled in the art. Typically, in humans, the maximum allowance per day is 2000 mg calcium per day.

Combination Therapy for the Treatment of Arthritis

For treatment for arthritis in accordance with the present invention, a compound or composition of the present invention is suitably administered alone as an active ingredient in a pharmaceutical composition, or is co-administered with at least one anti-arthritic compound selected from a matrix metalloproteinase inhibitor, an inhibitor of pro-inflammatory cytokines (e.g., anti-TNF molecules, TNF soluble receptors, and IL1 beta, non-steroidal anti-inflammatory drugs (NSAIDs) such as prostaglandin synthase inhibitors (e.g., choline magnesium salicylate, salicylsalicyclic acid), or corticosteroids, such as methylprednisone, prednisone, or cortisone.

In certain embodiments a compound or composition of the present invention and the anti-arthritic compound are part of a single therapeutic composition (e.g. such that the administration may be accomplished with a single composition). In other embodiments, a compound or composition of the present invention and the anti-arthritic compound are separate compositions (e.g. such that each composition may be administered separately to the subject). In preferred embodiments, a composition of the present invention and the anti-arthritic compound are administered to the subject at about the same time (e.g., within a few seconds, minutes, or hours of each other). In certain embodiments it may also be advantageous to administer the active compound together with an analgesic or other pain killer medication such as acetaminophen or ibuprofen.

Combination Therapy for the Treatment of Intestinal Bowel Disease

For treatment for intestinal bowel disease in accordance with the present invention, a compound or composition of the present invention is suitably administered alone as an active ingredient in a pharmaceutical composition, or is co-administered with at least one anti-inflammatory compound selected from a matrix metalloproteinase inhibitor, an inhibitor of pro-inflammatory cytokines (e.g., anti-TNF molecules, TNF soluble receptors, and IL1RA., non-steroidal anti-inflammatory drugs (NSAIDs) such as prostaglandin synthase inhibitors (e.g., choline magnesium salicylate, salicylsalicyclic acid), COX-1 or COX-2 inhibitors, or corticosteroids, such as methylprednisone, prednisone, or cortisone.

In certain embodiments a composition of the present invention and the anti-inflammatory compound are part of a single therapeutic composition (e.g. such that the administration may be accomplished with a single composition). In other embodiments, a composition of the present invention and the anti-inflammatory compound are separate compositions (e.g. such that each composition may be administered separately to the subject). In preferred embodiments, a compound or composition of the present invention and the anti-inflammatory compound are administered to the subject at about the same time (e.g., within a few seconds, minutes, or hours of each other). In certain embodiments it may also be advantageous to administer the active compound together with an analgesic or other pain killer medication such as acetaminophen or ibuprofen.

EXAMPLE 1

Preparation of 3,3-bis[4-hydroxy-3-methylphenyl]-pentane

A. A mixture of o-cresol (9.8 g, 100 mmol), 3-pentanone (4.3 g, 50 mmol) and $H_2O$ (4 mL) was chilled to 0° C. and then charged dropwise with conc $H_2SO_4$ (18 g). After 15 min, the reaction mixture was stirred at ambient temperature 16 h. The resulting mixture was diluted with water (150 mL) and extracted with EtOAc (3×75 mL). Combined organic layers were washed with satd $NaHCO_3$ (3×50 mL), brine (1×75 mL), dried (anhyd $Na_2SO_4$), and concentrated under reduced pressure. The resulting residue was chromatographed (silica, EtOAc/Hex, 0:100 to 20:80) to provide the title compound (4.1 g, 29%) as a white solid. $^1$H-NMR (CDCl$_3$) δ 6.85-6.90 (4H, m), 6.65 (2H, d), 4.59 (2H, s), 2.19 (6H, s), 2.00 (4H, q), 0.59 (6H, t).

Preparation of 4-{1-[4-(tert-butyl-dimethylsiloxy)-3-methylphenyl]-1-ethylpropyl}-2-methylphenol B. To a solution of 3,3-bis[4-hydroxy-3-methylphenyl]-pentane (5.75 g, 20.2 mmol) in anhyd DMF (50 mL) was added imidazole (1.3 g, 22.2 mmol) and TBSCI (3.0 g, 20.2 mmol). After 16 h the reaction mixture was diluted with $H_2O$ (100 mL) and extracted with EtOAc (3×75mL). Combined organic layers were washed with $H_2O$ (3×75 mL), brine and dried (anhyd $Na_2SO_4$). After concentrating under reduced pressure, the crude material was purified by chromatography (silica, EtOAc/Hex, 0:100 to 20:80) to afford the title compound (5.8 g, 72%). $^1$H-NMR (CDCl$_3$) δ 6.81-6.92 (4H, m), 6.65 (1H, d), 6.63 (1H, d), 4.51 (1H, s), 2.19 (3H, s), 2.15 (3H, s), 2.0 (4H, q), 1.00 (9H, s), 0.59 (6H, t), 0.20 (6H, s).

Preparation of trifluoromethanesulfonic acid 4-1-[4-(tert-butyl-dimethylsiloxy)-3-methylphenyl]-1-Ethyl-propyl}-2-methylphenyl ester C. To a solution of 41-[4-(tert-butyl-dimethylsiloxy)-3-methylphenyl]-1-ethylpropyl}-2-methylphenol (1.6 g, 4.0 mmol) and 2,6-lutidine (0.70 mL, 6.0 mmol) in anhyd DCM (20 mL) chilled to −10° C. was added dropwise triflic anhydride (0.84 mL, 5.0 mmol). After stirring 3 h, the reaction mixture was diluted with DCM (100 mL) and washed with 1N HCl (2×30 mL) and brine, then dried (anhyd $Na_2SO_4$) and concentrated under reduced pressure to yield the title compound (2.15 g, quant), which was used in the following step without purification. $^1$H-NMR (CDCl$_3$) δ 7.02-7.14 (3H, m), 6.86 (1H, d, J=2.3), 6.80 (1H, dd, J=2.3, 8.3), 6.65 (1H, d, J=8.3), 2.32 (3H, s), 2.16 (3H, s), 2.03 (4H, q, J=7.3), 1.01 (9H, s), 0.59 (6H, t, J=7.3), 0.21 (6H, s); $R_f$=0.90 (silica, DCM).

Preparation of 4-(4-{1-[4-(tert-butyl-dimethylsiloxy)-3-methylphenyl]-1-ethylpropyl}-2-methylphenyl)-2-methylbut-3-yn-2-ol D. To an oven-dried, argon-sparged flask was added Pd[PPh$_3$]$_4$ (46 mg) and anhyd CuI (15 mg). To the flask under argon was added a solution of trifluoromethanesulfonic acid 4-{1-[4-(tert-butyl-dimethylsiloxy)-3-methylphenyl]-1-ethyl-propyl}-2-methylphenyl ester (0.42 g, 0.80 mmol) in anhyd DMF (2.5 mL), TEA (0.56 mL, 4.0 mmol) and 2-methyl-3-butyn-2-ol (0.12 mL, 1.2 mmol). After heating at 65° C. for 15 h, the reaction mixture was diluted with Et$_2$O (50 mL), washed with $H_2O$ (2×30 mL) and brine, then dried (Na$_2$SO$_4$) and concentrated under reduced pressure. The crude material was chromatographed (silica, EtOAc/Hex, 0:100 to 10:90) to afford the title compound (0.12 g, 32%) as an orange oil. $^1$H-NMR (CDCl$_3$) δ 7.26 (1.4H, d, J=8.1), 7.01 (1H, d, J=1.8), 6.94 (1H, dd, J=1.8, 8.1), 6.85 (1H, d, J=2.3), 6.80 (1H, dd, J=2.3, 8.3), 6.63 (1H, d, J=8.3), 2.36 (3H, s), 2.14 (3H, s), 2.03 (4H, q, J=7.3), 1.63 (6H, s), 1.01 (9H, s), 0.59 (6H, t, J=7.3), 0.20 (6H, s); $R_f$=0.10 (silica, 1:9 EtOAct/Hx).

E. In a similar manner as described for Example 1D, but replacing 2-methyl-3-butyn-2-ol with the appropriate alkyne, the following compounds were prepared:

5-(4-{1-[4-(tert-butyl-dimethylsiloxy)-3-methylphenyl]-1-ethylpropyl}-2-methylphenyl)-3-ethylpent-4-yn-3-ol: $^1$H-NMR (C$_6$D$_6$) δ 7.44 (1H, d, J=8.1), 7.14 (1H, d, J=1.8), 7.06 (1H, d, J=2.3), 7.00 (1H, dd, J=1.8, 8.1), 6.93 (1H, dd, J=2.3, 8.3), 6.76 (1H, d, J=8.3), 2.34 (3H, s), 2.19 (3H, s), 2.01 (4H, q, J=7.3), 1.69 (4H, q, J=7.3), 1.10 (6H, t, J=7.3), 1.01 (9H, s), 0.66 (6H, t, J=7.3), 0.12 (6H, s);

5-(4-{1-[4-(tert-butyl-dimethylsiloxy)-3-methylphenyl]-1-ethylpropyl}-2-methylphenyl)-4,4-dimethylpent-1-yn-3-ol;

5-(4-{1-[4-(tert-butyl-dimethylsiloxy)-3-methylphenyl]-1-ethylpropyl}-2-methylphenyl)-5-methylhex-1-yn-3-ol: $^1$H-NMR (CDCl$_3$) δ 7.27 (1.2H, d, J=8.1), 7.01 (1H, d, J=1.8), 6.94 (1H, dd, J=1.8, 8.1), 6.86 (1H, d, J=2.3), 6.81 (1H, dd, J=2.3, 8.3), 6.63 (1H, d, J=8.3), 4.67 (1H, t, J=7.1), 2.37 (3H, s), 2.14 (3H, s), 2.03 (4H, q, J =7.3), 1.94 (1H, sept, J=6.8), 1.63-1.77 (2H, overlapping ddd, J=7), 1.00 (9H, s), 0.97 (6H, app t, J=6.8), 0.59 (6H, t, J=7.3), 0.20 (6H, s).

Preparation of 4-(4-{(-[4-(tert-butyl-dimethylsiloxy)-3-methylphenyl]-1-ethylpropyl}-2-methylphenyl)-2-methylbutan-2-ol F. A solution of 4-(4-{1-[4-(tert-butyl-dimethylsiloxy)-3-methylphenyl]-1-ethylpropyl}-2-methylphenyl)-2-methylbut-3-yn-2-ol (0.30 g, 0.65 mmol) in anhyd MeOH (30 mL) was prepared in a pressure flask, sparged with a stream of nitrogen (5 min), then charged with 5% Pd/C (200 mg) and transferred to the Parr hydrogenation apparatus. The flask was evacuated briefly and back-filled with nitrogen (2 cycles), evacuated briefly and back-filled with hydrogen (2 cycles) and then pressurized with hydrogen (60 psi). After shaking 12 h, the flask was evacuated briefly and back-filled with nitrogen (2 cycles). The reaction mixture was filtered through Celite, and the filter agent was washed with EtOAc (50 mL). The combined filtrates were concentrated under reduced pressure to give the title compound (0.25 g, 83%) as a white tacky solid, which was used without purification in the next step: $^1$H-NMR (CD$_2$Cl$_2$) δ 7.03 (1H, d, J=8.1), 6.92-6.97 (3H, m), 6.86 (1H, dd, J=2.3, 8.3), 6.67 (1H, d, J=8.3), 2.64 (2H, m), 2.27 (3H, s), 2.16 (3H, s), 2.06 (4H, q, J=7.3), 1.70 (2H, m), 1.29 (6H, s), 1.03 (9H s), 0.60 (6H, t, J=7.3), 0.22 (6H, s).

Preparation of 4-{1-ethyl-1-[4-(3-hydroxy-3-methylbutyl)-3-methyl-phenyl]-propyl}-2-methylphenol G. To a solution of 4-(4-{1-[4-(tert-butyl-dimethylsiloxy)-3-methylphenyl]-1-ethylpropyl}-2-methylphenyl)-2-methylbutan-2-ol (0.25 g, 0.50 mmol) in anhyd THF (1.5 mL) was added a 1.0M solution of TBAF in THF (0.70 mL, 0.70 mmol). After 1.5 h the reaction mixture was diluted with EtOAc (30 mL), washed with satd NH$_4$Cl (20 mL) and brine, then dried (Na$_2$SO$_4$) and concentrated under reduced pressure. The crude material was chromatographed (silica, EtOAc/Hex, 0:100 to 40:60) to yield the title compound (0.14 g, 74%) as a white tacky solid: $^1$H-NMR (C$_6$D$_6$) δ 7.23-7.28 (2H, m), 7.16-7.22 (2H, m), 7.11 (1H, dd, J=2.3, 8.3), 6.64 (1H, d, J=8.3), 5.39 (1H, br s), 2.66 (2H, m), 2.25 (6H, s), 2.21 (4H, q, J=7.3), 1.62 (2H, m), 1.14 (6H, t, J=7.3).

Preparation of 3-(4-{1-ethyl-1-[4-(3-hydroxy-3-methylbutyl)-3-Methylphenyl]-propyl}-2-methylphenoxy)-propane-1,2(S)-diol H. To a solution of 4-{1-ethyl-1-[4-(3-hydroxy-3-methylbutyl)-3-methyl-phenyl]propyl}-2-methylphenol (0.14 g, 0.40 mmol) in anhyd DMF (2 mL) was added CsF (67 mg, 0.44 mmol), Cs$_2$CO$_3$ (26 mg, 80 □ mol) and (S)-glycidol (29 µL, 0.44 mmol). The reaction mixture was heated at 80° C. for 4 h. After cooling, the mixture was diluted with DCM (40 mL), washed with H$_2$O (2×40 mL), 1 N HCl (20 mL) and brine, then dried (Na$_2$SO$_4$) and concentrated under reduced pressure. The crude material was chromatographed (silica, EtOAc/DCM, 0:100 to 75:25) to provide the title compound (80 mg, 47%) as a white powdered solid: $^1$H-NMR (CD$_2$Cl$_2$) δ 7.01 (1H, d, J=8.1), 6.96 (1H, dd, J=2.3, 8.3), 6.88-6.94 (3H, m), 6.73 (1H, d, J=8.3), 3.97-4.11 (3H, m), 3.77-3.84 (1H, m), 3.69-3.76 (1H, m), 2.62 (2H, m), 2.53 (1H, d, J=5.1), 2.24 (3H, s), 2.16 (3H, s), 2.05 (4H, q, J=7.3), 1.99 (1H, t, J=6.1), 1.67 (2H, m), 1.27 (6H, s), 0.58 (6H, t, J=7.3); $^{13}$C-NMR (CD$_2$Cl$_2$) δ 155.0, 147.2, 142.0, 138.4, 135.7, 131.2, 130.4, 128.5, 126.9, 126.3, 126.2, 110.9, 71.4, 71.3, 70.1, 64.6, 49.3, 45.2, 29.8, 29.6, 28.3, 20.0, 17.0, 8.9.

I. In a similar manner as described in the syntheses of Examples 1F-1H, the following compounds were prepared from respective intermediates of Example 1E:

3-(4-{1-ethyl-1-[4-(3-ethyl-3-hydroxypentyl)-3-methylphenyl]-propyl}-2-methyl-phenoxy)-propane-1,2(S)-diol: $^1$H-NMR (CD$_2$Cl$_2$) δ 7.01 (1H, d, J=8.1), 6.97 (1H, dd, J=2.3, 8.6), 6.88-6.94 (3H, m), 6.73 (1H, d, J=8.6), 3.98-4.10 (3H, m), 3.69-6.84 (2H, m), 2.51-2.59 (3H, m), 2.25 (3H, s), 2.16 (3H, s), 2.05 (4H, q, J=7.3), 1.99 (1H, app t, J=5.6), 1.62 (2H, m), 1.53 (4H, q, J=7.3), 0.89 (6H, t, J=7.3), 0.58 (6H, t, J=7.3); $^{13}$C-NMR (CD$_2$Cl$_2$) δ 155.0, 147.1, 142.0, 138.6, 135.6, 131.1, 130.4, 128.6, 126.9, 126.3, 126.2, 110.9, 75.1, 71.3, 70.1, 64.6, 49.3, 39.7, 31.7, 29.6, 27.5, 20.1, 17.0, 8.9, 8.4;

3-(4-{1-ethyl-1-[4-(3-hydroxy-4,4-dimethylpentyl)-3-methylphenyl]-propyl}-2-methyl-phenoxy)-propane-1,2(S)-diol: $^1$H-NMR (C$_6$D$_6$) δ 7.03 (1H, d, J=8.3), 6.97 (1H, dd, J=2.3, 8.3), 6.89-6.94 (3H, m), 6.73 (1H, d, J=8.6), 4.03-4.11 (1H, m), 3.98-4.02 (2H, m), 3.80 (1H, ddd, J=3.8, 6.6, 11.1), 3.69-3.76 (1H, m), 3.22 (1H, dd, J=1.5, 5.3), 2.84 (1H, ddd, J=5.1, 10.6, 13.9), 2.54 (1H, ddd, J=6.1, 10.4, 13.9), 2.52 (1H, d, J=5.1), 2.25 (3H, s), 2.16 (3H, s), 2.05 (4H, q, J=7.3), 1.97 (1H, app t), 1.73-1.82 (1H, m), 1.42-1.52 (1H, m), 0.88 (9H, s), 0.58 (6H, t, J=7.3);

3-(4-{1-ethyl-1-[4-(3-hydroxy-5-methylhexyl)-3-methylphenyl]-propyl}-2-methyl-phenoxy)-propane-1,2(S)-diol: $^1$H-NMR (CDCl$_3$) δ 7.00 (1H, d, J=8.3), 6.96 (1H, dd, J =2.3, 8.3), 6.88-6.94 (3H, m), 6.70 (1H, d, J=8.3), 4.08-4.14 (1H, m), 4.04 (2H, m), 3.86 (1H, dd, J=3.8, 11.4), 3.78 (1H, dd, J=5.3, 11.4), 3.72 (1H, m), 2.74 (1H, ddd, J =5.8, 10.4, 13.9), 2.60 (1H, ddd, J=6.1, 10.1, 13.9), 2.25 (3H, s), 2.17 (3H, s), 2.03 (4H, q, J=7.3), 1.86 (1H, br s), 1.60-1.82 (2H, m), 1.38-1.46 (1H, m), 1.24-1.32 (1H, m), 0.91 (6H, overlap d, J=6.6), 0.59 (6H, t, J=7.3); $^{13}$C-NMR (CDCl$_3$) δ 153.7, 146.0, 141.1, 136.8, 134.5, 130.4, 129.6, 127.6, 126.1, 125.4, 125.1, 109.8, 70.2, 69.6, 69.0, 63.6, 48.4, 46.6, 38.0, 28.9, 28.7, 24.4, 23.1, 21.9, 19.4, 16.3, 8.2.

EXAMPLE 2

Preparation of 4-{1-ethyl-1-[4-(3-hydroxy-4,4-dimethylpent-1-ynyl)-3-methylphenyl]-propyl}-2-methylphenol In a manner similar to that described in Example 1G, the title compound was prepared from 5-(4-{1-[4-(tert-butyl-dimethylsiloxy)-3-methylphenyl]-1-ethylpropyl}-2-methylphenyl)-4,4-dimethylpent-1-yn-3-ol: $^1$H-NMR (CDCl$_3$) δ 7.28 (1H, d, J=8.1), 7.00 (1H, d, J=1.8), 6.94 (1H, dd, J=1.8, 8.1), 6.82-6.87 (2H, m), 6.65 (1H, d, J=8.1), 4.51 (1H, s), 4.26 (1H, d, J=6.1), 2.38 (3H, s), 2.19 (3H, s), 2.03 (4H, q, J=7.3), 1.77 (1H, d, J=6.1), 1.07 (9H, s), 0.59 (6H, t, J=7.3).

Preparation of 3-(4-{1-ethyl-1-[4-(3-hydroxy-4,4-dimethylpent-1-ynyl)-3-methylphenyl]-propyl}-2-methylphenoxy)-propane-1,2(S)-diol B. In a manner similar to that described for Example 1H, the title compound was prepared from 4-{1-ethyl-1-[4-(3-hydroxy-4,4-dimethylpent-1-ynyl)-3-methylphenyl]-propyl}-2-methylphenol: $^1$H-NMR (CDCl$_3$) δ 7.29 (1H, d, J=8.1), 7.00 (1H, d, J=2), 6.92-6.97 (2H, m), 6.88 (1H, d, J=2.3), 6.71 (1H, d, J=8.3), 4.27 (1H, s), 4.13 (1H, m), 4.03-

4.07 (2H, m), 3.87 (1H, dd, J=3.8, 11.4), 3.79 (1H, dd, J=5.3, 11.4), 2.39 (3H, s), 2.17 (3H, s), 2.04 (4H, q, J=7.3), 1.07 (9H, s), 0.60 (6H, t, J=7.3).

The two diastereomers of 3-(4-{1-ethyl-1-[4-(3-hydroxy-4,4-dimethylpent-1-ynyl)-3-methylphenyl]-propyl}-2-methylphenoxy)-propane-1,2(S)-diol were resolved via chiral HPLC (Chiralcel AD column, 1.0 cm×25 cm), eluting with 1:9 IPA-Hex at 5 mL/min. The first isomer (Rf. 16.04 min, de>96%) and second isomer (Rf: 21.79 min, de>96%) were obtained as white powdered solids. Retention time and diastereomeric excess were determined by HPLC (Chiralcel AD, 0.46 cm×25 cm; 1:9 IPA-Hex at 1 mL/min). Absolute stereochemistry has not been assigned for each of the isolated products. One of the two diastereomers was submitted as CompoundB for the mice study shown in FIGS. 1 and 2.

Preparation of 3-(4-{1-ethyl-1-[4-(3-ethyl-3-hydroxypent-1-ynyl)-3-methyl-phenyl]-propyl}-2-methylphenoxy)-propane-1,2(S)-diol C. In a manner similar to that described in Examples 2A-B, the title compound was prepared from 5-(4-{1-[4-(tert-butyl-dimethylsiloxy)-3-methylphenyl]-1-ethylpropyl}-2-methylphenyl)-3-ethylpent-4-yn-3-ol: $^1$H-NMR (CDCl$_3$) δ 7.27 (1H, d, J=8.6), 6.99 (1H, d, J=1.8), 6.91-6.99 (2H, m), 6.86 (1H, d, J=2.3), 6.70 (1H, d, J=8.6), 4.08-4.15 (1H, m), 4.04 (2H, m), 3.86 (1H, dd, J=3.8, 11.4), 3.78 (1H, d, J=5.3, 11.4), 2.55 (1H, br s), 2.37 (3H, s), 2.16 (3H, s), 2.04 (4H, q, J=7.3), 1.96 (1H, br s), 1.77 (4H, m), 1.11 (6H, t, J=7.3), 0.59 (6H, t, J=7.3).

EXAMPLE 3

Preparation of (E)-4-{1-ethyl-1-[4-(3-hydroxy-4,4-dimethylpent-1-enyl)-3-methylphenyl]-propyl}-2-methylphenol A. To a solution of 1-(4-{1-[4-(tert-butyl-dimethylsiloxy)-3-methylphenyl]-1-ethylpropyl}-2-methylphenyl)-4,4-dimethylpent-1-yn-3-ol (0.22 g, 0.45 mmol) in anhyd THF (2 mL) was added LiAlH$_4$ (19 mg, 0.49 mmol). The reaction mixture was heated at 65° C. for 6 h. After cooling to ambient temperature, the reaction mixture was quenched sequentially with H$_2$O (0.21 mL), 15% NaOH (0.21 mL) and then H$_2$O (0.63 mL). The resulting mixture was diluted with Et$_2$O, filtered through Celite, washed with brine, dried (Na$_2$SO$_4$) and concentrated to yield (E)-1-(4-{1-[4-(tert-butyl-dimethylsiloxy)-3-methylphenyl]-1-ethylpropyl}-2-methylphenyl)-4,4-dimethylpent-1-en-3-ol (0.15 g, 68%), which was used without purification in the next step.

In a manner similar to that described for Example 1G, (E)-1-(4-{1-[4-(tert-butyl-dimethylsiloxy)-3-methylphenyl]-1-ethylpropyl}-2-methylphenyl)-4,4-dimethylpent-1-en-3-ol was deprotected and the crude material was purified via normal-phase preparative chromatography (YMC column, 5-35% EtOAc/Hex) to afford the title compound (74 mg, 36%): $^1$H-NMR (CDCl$_3$) δ 7.31 (1H, d, J=8.6), 6.93-6.98 (2H, m), 6.84-6.92 (2H, m), 6.74 (1H, d, J=15.7), 6.65 (1H, d, J=8.1), 6.13 (1H, dd, J=7.3, 15.7), 4.49 (1H, s), 3.92 (1H, dd, J=3.0, 7.3), 2.30 (3H, s), 2.19 (3H, s), 2.04 (4H, q, J=7.3), 1.50 (1H, d, J=4.0), 0.97 (9H, s), 0.61 (6H, t, J=7.3).

Preparation of (E)-3-(4-{1-ethyl-1-[4-(3-hydroxy-4,4-dimethylpent-1-enyl)-3-methylphenyl]-propyl}-2-methylphenoxy)-propane-1,2(S)-diol B. In a manner similar to that described for Example 1H, the title compound was prepared from (E)-4-{1-ethyl-1-[4-(3-hydroxy-4,4-dimethylpent-1-enyl)-3-methylphenyl]-propyl}-2-methylphenol: $^1$H-NMR (CDCl$_3$) δ 7.31 (1H, d, J=8.8), 6.90-6.99 (4H, m), 6.74 (1H, d, J=15.9), 6.70 (1H, d, J=8.8), 6.13 (1H, dd, J=7.3, 15.9), 4.08-4.15 (1H, m), 4.04 (2H, m), 3.92 (1H, d, J=7.3), 3.86 (1H, dd, J=3.8, 11.4), 3.78 (1H, dd, J=5.3, 11.4), 2.57 (1H, br s), 2.30 (3H, s), 2.17 (3H, s), 2.05 (4H, q, J=7.3), 0.97 (9H, s), 0.61 (6H, t, J=7.3); $^{13}$C-NMR (CDCl$_3$) δ 154.3, 148.5, 141.3, 134.7, 133.2, 130.9, 130.3, 130.1, 130.0, 126.5, 126.2, 125.7, 125.2, 110.3, 81.6, 70.7, 69.4, 64.1, 49.1, 35.4, 29.3, 26.0, 20.4, 16.8, 8.6.

Preparation OF (E)-3-(4-{1-ethyl-1-[4-(3-ethyl-3-hydroxypent-1-enyl)-3-methylphenyl]-propyl}-2-methylphenoxy)-propane-1,2(S)-diol C. As described in Examples 3-A-B, the title compound was prepared from 5-(4-{1-[4-(tert-butyl-dimethylsiloxy)-3-methylphenyl]-1-ethylpropyl}-2-methylphenyl)-3-ethylpent-4-yn-3-ol: $^1$H-NMR (CDCl$_3$) δ 7.29 (1H, d, J=8.8), 6.91-6.99 (4H, m), 6.74 (1H, d, J=15.9), 6.70 (1H, d, J=8.6), 6.01 (1H, d, J=15.9), 4.08-4.14 (1H, m), 4.04 (2H, m), 3.75-3.89 (2H, m), 2.54 (1H, d, J=5.3), 2.31 (3H, s), 2.17 (3H, s), 2.05 (4H, q J=7.3), 2.00 (1H, t, J=6.1), 1.64 (4H, overlap q), 1.42 (1H, s), 0.92 (6H, t, J=7.3), 0.61 (6H, t, J=7.3); MS(ESI): 472 (M+NH$_4$$^+$).

Preparation of (Z)-4-{1-ethyl-1-[4-(3-hydroxy-4,4-dimethylpent-1-enyl)-3-methylphenyl]-propyl}-2-methylphenol D. A solution of 1-(4-{1-[4-(tert-butyl-dimethylsiloxy)-3-methylphenyl]-1-ethylpropyl}-2-methylphenyl)-4,4-dimethylpent-1-yn-3-ol (0.4 g, 0.8 mmol) in anhyd MeOH (10 mL) was sparged with a stream of nitrogen (5 min) and then charged with 5% Pd/C (17 mg). Next an atmosphere of hydrogen (ambient pressure) was introduced into the reaction flask via a hydrogen-filled balloon with an inlet needle. After sparging briefly with hydrogen (5 min), the reaction mixture was stirred 3 h at ambient pressure. The reaction mixture was diluted with EtOAc (30 mL) and filtered through Celite. The filter agent was rinsed with EtOAc, and the combined filtrates were concentrated to yield (Z)-1-(4{-1-[4-(tert-butyl-dimethylsiloxy)-3-methylphenyl]-1-ethylpropyl}-2-methylphenyl)-4,4-dimethylpent-1-en-3-ol (0.28 g, 71%), which was used without purification in the next step.

In a manner similar to that described for Example 1G, (Z)-1-(4-{1-[4-(tert-butyl-dimethylsiloxy)-3-methylphenyl]-1-ethylpropyl}-2-methylphenyl)-4,4-dimethylpent-1-en-3-ol was deprotected and the crude material was purified via normal-phase preparative chromatography (YMC column, 0-25% EtOAc/Hex) to afford the title compound (46 mg, 60%). $^1$H-NMR (C$_6$D$_6$) δ 7.39 (1H, d, J=8.3), 7.08-7.14 (2H, m), 7.02 (1H, d, J=2.3), 6.93 (1H, dd, J=2.3, 8.3), 6.47 (1H, d, J=11.6), 6.30 (1H, d, J=8.3), 5.64 (1H, dd, J=9.9, 11.6), 4.14 (1H, d, J=9.9), 3.93 (1H, br s), 2.11 (3H, s), 2.06 (4H, q, J=7.3), 2.04 (3H, s), 0.86 (9H, s), 0.68 (6H, t, J=7.3).

Preparation of (Z)-3-(4-{1-ethyl-1-[4-(3-hydroxy-4,4-dimethylpent-1-ENYL)-3-methylphenyl]-propyl}-2-methylphenoxy)-propane-1,2(S)-diol E. In a manner similar to that described for Example 1H, the title compound was prepared from (Z)-4-{1-ethyl-1-[4-(3-hydroxy-4,4-dimethylpent-1-enyl)-3-methylphenyl]-propyl}-2-methylphenol: $^1$H-NMR (CDCl$_3$) δ 7.14 (1H, d, J=8.6), 6.90-6.99 (4H, m), 6.71 (1H, d, J=8.6), 6.63 (1H, d, J=11.6), 5.77 (1H, dd, J=9.6, 11.6), 4.08-4.15 (1H, m), 4.04 (3H, m), 3.74-3.90 (2H, m), 2.59 (1H, br s), 2.19 (3H, s), 2.17 (3H, s), 2.13 (1H, br s), 2.05 (4H, q, J=7.3), 1.41 (1H, br s), 0.87 (9H, s), 0.60 (6H, t, J =7.3); $^{13}$C-NMR (CDCl$_3$) δ 154.1, 148.0, 141.2, 135.1, 133.0, 132.1, 130.7, 130.6, 129.4, 128.2, 126.3, 125.4, 125.3, 110.1, 75.0, 70.4, 69.2, 63.9, 48.9, 34.9, 29.1, 25.5, 20.3, 16.6, 8.4.

EXAMPLE 4

Preparation of
4-[1-(4-bromophenyl)-1-ethylpropyl]-2-methylphenol

A. A solution of ethyl 4-bromobenzoate (1.6 mL, 10 mmol) in anhyd THF (50 mL) was chilled to 0° C. and then charged dropwise with a 3.0 M solution of ethylmagnesium bromide in Et$_2$O (7.0 mL, 21 mmol). After 15 min, the reaction mixture was removed from the ice-bath and stirred at ambient temperature. After 18 h the opaque mixture was quenched with satd ammonium chloride (50 mL) and extracted with Et$_2$O (2×50 mL). The combined extracts were washed with brine, dried (anhyd Na$_2$SO$_4$) and concentrated under reduced pressure to give 3-(4-bromophenyl)-pentan-3-ol (2.45 g, quant) as a colorless liquid, which was used without purification in the next step: $^1$H-NMR (CDCl$_3$) δ 7.46 (2H, d, J=8.3), 7.26 (2.3H, d, J=8.3), 1.78-1.86 (4H, overlapping quartets, J=7), 0.76 (6H, t, J=7.3).

To a stirred suspension of 3-(4-bromophenyl)-pentan-3-ol (2.45 g, 10 mmol) and o-cresol 1.05 mL, 10.2 mmol) in H$_2$O (1.0 mL) chilled to 0° C. was added conc H$_2$SO$_4$ (4.0 g) dropwise. After 1.5 h the reaction mixture was diluted with H$_2$O (50 mL) and extracted with Et$_2$O (2×50 mL). The combined extracts were washed with water, satd NaHCO$_3$, and brine, then dried (anhyd Na$_2$SO$_4$) and concentrated under reduced pressure. The resulting crude product was chromatographed (silica, EtOAC/Hex, 0:100 to 10:90) to afford the title compound (2.1 g, 64% non-optimized) as a colorless liquid: $^1$H-NMR (CDCl$_3$) δ 7.36 (2H, d, J=8.6), 7.05 (2H, d, J=8.6), 6.83-6.88 (2H, m), 6.67 (1H, d, J=8.1), 4.52 (1H, br s), 2.20 (3H, s), 2.04 (4H, q, J=7.3), 0.61 (6H, t, J=7.3).

Preparation of 1-{4-[1-(4-benzyloxy-3-methylphenyl)-1-ethylpropyl]-phenyl}-4,4-dimethylpent-1-yn-3-ol B. To a solution of 4-[1-(4-bromophenyl)-1-ethylpropyl]-2-methylphenol (2.1 g, 6.3 mmol) in anhyd MeCN (30 mL) added anhyd K$_2$CO$_3$ (2.9 g, 21 mmol) and benzyl bromide (0.83 mL, 7.0 mmol). The reaction mixture was heated at reflux. After 20 h, the reaction mixture was cooled, diluted with Et$_2$O (100 mL) and filtered. The filtrate was washed with H$_2$O (2×50 mL) and brine, dried (anhyd Na$_2$SO$_4$), concentrated under reduced pressure and chromatographed (silica, EtOAC/Hex, 0:100 to 15:85) to give 5-[1-(4-bromophenyl)-1-ethylpropyl]-2-benzyloxytoluene (2.2 g, 82%), as a colorless liquid: $^1$H-NMR (CDCl$_3$) δ 7.43-7.48 (2H, m), 7.31-7.42 (5H, m), 7.06 (2H, d, J=8.6), 6.94 (1H, dd, J=2.3, 8.3), 6.89 (1H, d, J=2.3), 6.79 (1H, d, J=8.3), 5.05 (2H, s), 4.23 (1H, s), 2.23 (3H, s), 2.05 (4H, q, J=7.3), 0.62 (6H, t, J=7.3).

In a manner similar to that described for Example 1D, but replacing 2-methyl-3-butyn-2-ol with 4,4-dimethylpent-1-yn-3-ol, the title compound was prepared from 5-[1-(4-bromophenyl)-1-ethylpropyl]-2-benzyloxytoluene: $^1$H-NMR (CDCl$_3$) δ 7.44-7.48 (2H, m), 7.37-7.42 (2H, m), 7.31-7.36 (3H, m), 7.14 (2H, d, J=8.6), 6.94 (1H, dd, J=2.3, 8.3), 6.90 (1H, d, J=2.3), 6.79 (1H, d, J=8.3), 5.05 (2H, s), 2.22 (3H, s), 2.07 (4H, q, J=7.3), 1.07 (9H, s), 0.62 (6H, t, J=7.3).

Preparation of 4-{1-ethyl-1-[4-(3-hydroxy-4,4-dimethylpentyl)-phenyl]-propyl}-2-methylphenol C. In a manner similar to that described for Example 1F, the title compound was prepared from 1-{4-[1-(4-benzyloxy-3-methylphenyl)-1-ethylpropyl]-phenyl}-4,4-dimethylpent-1-yn-3-ol: $^1$H-NMR (CDCl$_3$) δ 7.09 (4H, s), 6.92 (1H, d, J=2.3), 6.88 (1H, dd, J=2.3, 8.3), 6.66 (1H, d, J=8.3), 3.23 (1H, dd, J=1.8, 10.4), 2.89 (1H, m), 2.59 (1H, m), 2.20 (3H, s), 2.05 (4H, q, J=7.3), 1.84 (1H, m), 1.57 (1H, m), 0.89 (9H, s), 0.61 (6H, t, J=7.3); $^{13}$C-NMR (CDCl$_3$) δ 151.7, 146.8, 141.4, 139.5, 131.1, 128.4, 128.1, 127.2, 122.9, 114.4, 80.0, 49.2, 35.4, 33.8, 33.3, 29.7, 26.1, 16.4, 8.8.

Preparation of 3-(4-{1-ethyl-1-[4-(3-hydroxy-4,4-dimethylpentyl)-phenyl]-propyl}-2-methylphenoxy)-propane-1,2(S)-diol D. In a manner similar to that described for Example 1H, the title compound was prepared from 4-{1-ethyl-1-[4-(3-hydroxy-4,4-dimethylpentyl)-phenyl]-propyl}-2-methylphenol: $^1$H-NMR (CDCl$_3$) δ 7.08 (4H, m), 6.97 (1H, dd, J=2.3, 8.3), 6.92 (1H, d, J=2.3), 6.63 (1H, d, J=8.3), 4.08-4.15 (1H, m), 4.04 (2H, m), 3.86 (1H, dd, J=3.8, 11.4), 3.78 (1H, dd, J=5.3, 11.4), 3.22 (1H, dd, J=1.8, 10.4), 2.88 (1H, ddd, J=5.1, 10.1, 13.9), 2.58 (1H, ddd, J=6.6, 9.6, 13.9), 2.16 (3H, s), 2.05 (4H, q, J=7.3), 1.92 (1H, br s), 1.77-1.88 (1H, m), 1.50-1.62 (1H, m), 0.88 (9H, s), 0.60 (6H, t, J=7.3); $^{13}$C-NMR (CDCl$_3$) δ 154.4, 146.7, 141.7, 139.6, 131.1, 128.4, 128.1, 126.7, 125.8, 110.5, 80.0, 70.8, 69.6, 64.3, 49.3, 35.4, 33.7, 33.3, 29.6, 26.1, 16.9, 8.8.

Preparation of 3-(4-{1-ethyl-1-[4-(3-HYDROXY-4-methylpentyl)-3-methyl-phenyl]-propyl}-2-methylphenoxy)-propane-1,2(S)-diol E. In a manner similar to that described for Examples 4A-D, the title compound was prepared by replacing ethyl 4-bromobenzoate with methyl 4-bromo-3-methylbenzoate and by replacing 2-methyl-3-butyn-2-ol with 4-methylpent-1-yn-3-ol: $^1$H-NMR (CDCl$_3$) δ 7.02 (1H, d, J=8.6), 6.96 (1H, dd, J=2.3, 8.3), 6.89-6.94 (3H, m), 6.70 (1H, d, J=8.6), 4.11 (1H, m), 4.02-4.05 (2H, m), 3.74-3.89 (2H, m), 3.42 (1H, br s), 2.77 (1H, ddd, J=5.1, 10.4, 13.9), 2.53-2.63 (2H, m), 2.25 (3H, s), 2.17 (3H, s), 2.04 (4H, q, J=7.3), 1.84 (1H, br s), 1.60-1.79 (3H, m), 1.34 (1H, br s), 0.92 (6H, overlap d), 0.59 (6H, t, J=7.3); MS(ESI): 443 (MH$^+$).

Preparation of 3-(2-ethyl-4-{1-ethyl-1-[4-(3-hydroxy-4,4-dimethylpentyl)-3-methylphenyl]-propyl}-phenoxy)-propane-1,2(S)-diol F. In a manner similar to that described for Examples 4A-D, the title compound was prepared by replacing o-cresol with 2-ethylphenol and by replacing ethyl 4-bromobenzoate with methyl 4-bromo-3-methylbenzoate: $^{13}$C-NMR (CDCl$_3$) δ 152.5, 144.9, 139.7, 136.2, 133.5, 130.0, 128.5, 127.7, 126.6, 125.0, 124.3, 108.9, 78.3, 69.1, 67.6, 62.3, 47.5, 33.7, 30.8, 29.1, 27.9, 24.4, 22.3, 18.3, 13.3, 7.1; MS(ESI): 488 (M+NH$_4^+$).

EXAMPLE 5

Preparation of 4-[1-ethyl-1-(4-methoxyphenyl)-propyl]-2-methylphenol

A. In a manner similar to that described for Example 4A, the title compound was prepared from methyl p-anisate: $^1$H-NMR (CDCl$_3$) δ 6.98 (2H, d, J=8.8), 6.80 (1H, d, J=2.3), 6.77 (1H, dd, J=2.3, 8.3), 6.69 (2H, d, J=8.8), 6.56 (1H, d, J=8.3), 3.69 (3H, s), 2.10 (3H, s), 1.93 (4H, q, J=7.3), 0.51 (6H, t, J=7.3).

Preparation of 1-{4-[1-ethyl-1-(4-methoxyphenyl)-propyl]-2-methylphenyl}-4,4-dimethylpent-1-yn-3-ol B. In a manner similar to that described for Examples 1C-D, but replacing 2-methyl-3-butyn-2-ol with 4,4-dimethylpent-1-yn-3-ol, the title compound was prepared from 4-[1-ethyl-1-(4-methoxyphenyl)-propyl]-2-methylphenol: $^1$H-NMR (CDCl$_3$) δ 7.29 (1H, d, J=8.1), 7.05 (2H, d, J=8.8), 7.00 (1H, d, J=2.3), 6.94 (1H, dd, J=2.3, 8.1), 6.78 (2H, d, J=8.8), 4.26 (1H, s), 3.78 (3H, s), 2.38 (3H, s), 2.05(4H, q, J=7.3), 1.06 (9H, s), 0.60 (6H, t, J=7.3).

Preparation of 4-{1-ethyl-1-[4-(3-hydroxy-4,4-dimethylpentyl)-3-methyl-phenyl]-propyl}-phenol C. In a manner similar to that described for Example 1F, 1-{4-[1-ethyl-1-(4-methoxyphenyl)-propyl]-2-methylphenyl}-4,4-dimethylpentan-3-ol was prepared from 1-{4-[1-ethyl-1-(4-methoxyphenyl)-propyl]-2-methylphenyl}-4,4-dimethylpent-1-yn-3-ol: $^1$H-NMR (CDCl$_3$) δ 7.00 (2H, d, J=8.8), 6.93 (1H, d, J=8.6), 6.81-6.85 (2H, m), 6.69 (2H, d, J=8.8), 3.69 (3H, s), 3.16 (1H, dd, J=1.8, 10.4), 2.77 (1H, m), 2.46 (1H, m), 2.16 (3H, s), 1.96 (4H, q, J=7.3), 1.70 (1H, m), 1.41 (1H, m), 0.80 (9H, m), 0.51 (6H, t, J=7.3).

A stirred suspension of NaH (60% dispersion in mineral oil, 80 mg, 2.0 mmol) in anhyd DMF (0.5 mL) was chilled to 0° C. and charged dropwise with ethanethiol (74 μL, 1.0 mmol). The reaction mixture was removed from the ice-bath and stirred at ambient temperature. After 10 min, additional DMF (0.5 mL) was added to facilitate stirring. To the resulting mixture was added dropwise a solution of 1-{4-[1-ethyl-1-(4-methoxyphenyl)-propyl]-2-methylphenyl}-4,4-dimethylpentan-3-ol (0.10 g, 0.26 mmol) in anhyd DMF (0.7 mL). The reaction mixture was transferred to an oil bath and heated at reflux. After 3 h the mixture was cooled, quenched with satd NH$_4$Cl (50 mL), extracted with Et$_2$O (2×50 mL). The combined extracts were washed with H$_2$O (2×50 mL) and brine, then dried (Na$_2$SO$_4$), concentrated under reduced pressure and chromatographed (silica, EtOAC/Hex, 0:100 to 25:75) to give the title compound (36 mg, 37% non-optimized) as a tacky white solid: $^1$H-NMR (CD$_2$Cl$_2$) δ 7.00-7.06 (3H, m), 6.90-6.94 (2H, m), 6.71 (2H, d), 4.95 (1H, br s), 3.24 (1H, dd, J=1.8, 10.6), 2.85 (1H, ddd, J=5.1, 10.6, 13.9), 2.54 (1H, ddd, J=6.1, 10.4, 13.9), 2.24 (3H, s), 2.05 (4H, q, J=7.3), 1.72-1.84 (1H, m), 1.42-1.54 (1H, m), 0.88 (9H, s), 0.59 (6H, t, J=7.3).

Preparation of 3-(4-{1-ethyl-1-[4-(3-hydroxy-4,4-dimethylpentyl)-phenyl]-propyl}-2-methylphenoxy)-propane-1,2(S)-diol D. In a manner similar to that described for Example 1H, the title compound was prepared from 41-ethyl-1-[4-(3-hydroxy-4,4-dimethylpentyl)-3-methyl-phenyl]-propyl}-phenol: $^1$H-NMR (CDCl$_3$) δ 7.10 (2H, d, J=8.8), 7.04 (1H, d, J=8.6), 6.90-6.94 (2H, m), 6.81 (2H, d, J=8.8), 4.02-4.13 (3H, m), 3.85 (1H, dd, J=3.8, 11.4), 3.76 (1H, dd, J=5.3, 11.4), 3.26 (1H, dd, J=1.5, 10.6), 2.87 (1H, ddd, J=5.1, 10.6, 13.9), 2.56 (1H, ddd, J=5.8, 10.1, 13.9), 2.26 (3H, s), 2.06 (4H, q, J=7.3), 1.75-1.85 (1H, m), 1.45-1.57 (1H, m), 0.90 (9H, s), 0.61 (6H, t, J=7.3); $^{13}$C-NMR (CDCl$_3$) δ 156.5, 146.7, 142.4, 138.1, 135.5, 130.4, 129.7, 128.5, 126.2, 114.1, 80.6, 70.9, 69.7, 64.3, 49.4, 35.6, 32.6, 31.0, 29.8, 26.3, 20.3, 9.0.

EXAMPLE 6

Preparation of 4,4-bis(4-hydroxy-3-methylphenyl)-piperidin-1-yl}-ethanone

A. In a manner similar to that described for Example 1A, the title compound was prepared by replacing 3-pentanone with 1-acetyl-4-piperidone: $^1$H-NMR (DMSO-d$_6$) δ 9.03 (2H, s), 6.95 (2H, d, J=2.3), 6.87 (2H, dd, J=2.3, 8.3), 6.65 (2H, d, J=8.3), 3.33-3.42 (4H, m), 2.24 (2H, m), 2.15 (2H, m), 2.05 (6H, s), 1.96 (3H, s).

Preparation of 1-(4-{1-acetyl-4-[4-(3,3-dimethyl-2-oxobutoxy)-3-methylphenyl]-piperidin-4-yl}-2-methylphenoxy)-3,3-dimethylbutan-2-one B. To a solution of 4,4-bis(4-hydroxy-3-methylphenyl)piperidin-1-yl}ethanone (1.0 g, 3.0 mmol) and 1-bromopinacolone (0.87 mL, 6.5 mmol) in anhyd THF (30 mL) was added 60% w/w NaH (suspension in oil, 0.52 g, 13 mmol) and NaI (0.1 g). The reaction mixture was heated at 50° C. After 30min the mixture was cooled, quenched with satd NH$_4$Cl (30 mL) and extracted with EtOAc (2×50 mL). The combined extracts were washed with 5% NaOH and brine, then dried (anhyd Na$_2$SO$_4$), concentrated under reduced pressure and chromatographed (silica, EtOAc/Hex, 50:50 to 100:0) to provide the title compound (1.2 g, 76%) as a white solid: $^1$H-NMR (CDCl$_3$) δ 6.99 (2H, d, J=2.3), 6.93 (2H, dd, J=2.3, 8.3), 6.51 (2H, d, J=8.3), 4.83 (4H, m), 3.62 (2H, m), 3.46 (2H, m), 2.26-2.34 (4H, m), 2.25 (6H, s), 2.07 (3H, s), 1.24 (18H, s).

Preparation of 1-(4-{4-[2(S),3-dihydroxy-propoxy]-3-methylphenyl}-4-[4-(2-hydroxy-3,3-dimethylbutoxy)-3-methylphenyl]-piperidin-1-yl)-ethanone C. In a manner similar to that described for Example 6B, 1-{4-[1-acetyl-4-(4-hydroxy-3-methylphenyl)-piperidin-4-yl]-2-methylphenoxy}-3,3-dimethylbutan-2-one was prepared by using 1 equiv of 1-chloropinacolone and cesium carbonate. 1-{4-[1-Acetyl-4-(4-hydroxy-3-methylphenyl)-piperidin-4-yl]-2-methylphenoxy}-3,3-dimethylbutan-2-one was then alkylated with (S)-glycidol as in Example 1H to yield 1-(4-(1-acetyl-4-[4-(2,3-dihydroxypropoxy)-3-methylphenyl]-piperidin-4-yl}-2-methylphenoxy)-3,3-dimethylbutan-2-one.

To a solution of 1-(4-{1-acetyl-4-[4-(2,3-dihydroxypropoxy)-3-methylphenyl]-piperidin-4-yl}-2-methylphenoxy)-3,3-dimethylbutan-2-one (0.14 g, 0.28 mmol) in anhyd MeOH (3 mL) cooled to 0° C. was added sodium borohydride (11 mg, 0.29 mmol). After 8 h the reaction was quenched with water and extracted with EtOAc (2×20 mL). The combined extracts were washed with brine, dried (anhyd Na$_2$SO$_4$), concentrated under reduced pressure and purified by reverse-phase HPLC (C18 column), eluting with 0.05% TFA in MeCN—H$_2$O (1:9 to 9:1) to provide the title compound (0.10 g, 73%) as a white solid: $^1$H-NMR (CDCl$_3$) δ 6.96-7.01 (4H, m), 6.74 (2H, d, J=8.3), 4.05-4.14 (2H, m), 4.03 (2H, m), 3.82-3.88 (2H, m), 3.74-3.80 (1H, dd, J=5.3, 11.4), 3.67-3.71 (1H, dd, J=2.8, 8.6), 3.64 (2H, m), 3.47 (2H, m), 2.27-2.36 (4H, m), 2.19 (3H, s), 2.18 (3H, s), 2.08 (3H, s), 1.00 (9H, s).

Preparation of 3-(4-{4-[4-(2-hydroxy-3,3-dimethyl-butoxy)-3-methylphenyl]-piperidin-4-yl}-2-methylphenoxy)-propane-1,2(S)-diol D. To a solution of 1N NaOH (8 mL) in MeOH (2 mL) was added 1-(4-{4-[2(S),3-dihydroxy-propoxy]-3-methylphenyl}-4-[4-(2-hydroxy-3,3-dimethylbutoxy)-3-methylphenyl]piperidin-1-yl)ethanone (30 mg, 0.058 mmol). The reaction mixture was heated at 80° C. for 16 h, cooled, acidified with 1N HCl (8-9 mL), and washed with EtOAc. The aqueous layer was lyophilized and the crude material was purified by reverse-phase HPLC (C18 column), eluting with 0.05% TFA in MeCN—H$_2$O (1:9 to 9:1) to provide the title compound (8.2 mg, 24%) as its TFA salt: $^1$H-NMR (DMSO-d$_6$) δ 8.31 (2H, br s), 7.00 (4H, m), 6.78 (2H, app t), 4.70-4.90 (2H, m), 4.56-4.66 (1H, m), 3.88-4.04 (2H, m), 3.70-3.86 (3H, m), 3.00 (4H, br s), 2.47 (4H, br s), 2.12 (3H, s), 2.11 (3H, s), 2.09 (1H, br s), 0.91 (9H, s); MS(ESI): 472 (MH$^+$).

E. In a manner similar to that described for Examples 6A-6C, the following compounds were prepared by replacing 1-acetyl-4-piperidone with either 2,2,2-trifluoroacetophenone or 2,2,3,3,3-pentafluoropropiophenone, respectively:

3-(2-methyl-4-{2,2,2-trifluoro-1-[4-(2-hydroxy-3,3-dimethylbutoxy)-3-methylphenyl]-1-phenylethyl}-phenoxy)-propane-1,2(S)-diol: $^1$H-NMR (CDCl$_3$) δ 7.31 (2H, d, J=2.3), 7.30 (1H, m), 7.14-7.15 (2H, m), 6.95-6.99 (2H, m), 6.80-6.85 (2H, m), 6.73 (2H, d, J=8.6), 4.09-4.17 (2H, m), 4.07 (2H, m), 3.89 (2H, m), 3.69-3.83 (2H, m), 2.52 (1H, br s), 2.39 (1H, br s), 2.17 (6H, s), 1.96 (1H, br s), 1.01 (9H, s); MS(ESI): 564 (M+NH$_4^+$);

3-(2-methyl-4-{2,2,3,3,3-pentafluoro-1-[4-(2-hydroxy-3,3-dimethylbutoxy)-3-methylphenyl]-1-phenylpropyl}-phenoxy)-propane-1,2(S)-diol: $^1$H-NMR (CDCl$_3$) δ 7.32 (2H, d, J=2.3), 7.29 (1H, m), 7.14-7.15 (2H, m), 6.95-6.99 (2H, m), 6.80-6.85 (2H, m), 6.71 (2H, d, J=8.6), 4.08-4.16 (2H, m), 4.05 (2H, m), 3.88 (2H, m), 3.69-3.81 (2H, m), 2.51 (1H, br s), 2.38 (1H, br s), 2.16 (6H, s), 1.97 (1H, br s), 1.01 (9H, s); MS(ESI): 614 (M+NH$_4^+$).

EXAMPLE 7

Two Hybrid Assay

Compound activity was determined using a modified mammalian two-hybrid assay, using the interaction of VDR to the co-factor SRC-1 to monitor receptor activation.

pCMX-VP16-VDR receptor chimera was constructed by cloning nucleotides encoding amino acids 92-425 of the ligand binding domain of human VDR protein into the Asp718/BamH1 sites of pCMX-VP16 (Umesono et al. *Cell* 65 (7) 1255-66) (1991).

pCMX-GAL4-SCR-1 was constructed by cloning nucleotides encoding amino acids 381-891 of SRC-1 into the vector pCMX-GAL4 (Perlmann et al. *Genes & Development* 7 1411-1422 (1993)) comprising nucleotides encoding for amino acids 1-147 of the GAL4 DNA binding domain.

Gal4-tk-Luc (GAL4$_{UAS}$-Tk-Luciferase) reporter constructs were constructed by insertion of four copies of the Gal4 UAS (Kang et al. *J. Biol. Chem.* 268 9629-9635 (1993)) into the Hind III site of tk-Luc. The parental plasmid tk-Luc was prepared by insertion of the Herpes simplex virus thymidine kinase gene promoter (−105 to +51) obtained from the plasmid pBLCAT2 by digestion with HindIII and XhoI (described in Luckow et al. *Nuc. Acid. Res.* 15 5490 (1987)) into the plasmid MTV-LUC described by Hollenberg and Evans (*Cell* 55 899-906 (1988)) after removal of MTV-LTR promoter sequence from MTV-LUC via digestion with HindIII and XhoI. Correct cloning was confirmed by restriction digestion and or sequencing.

Assays were performed using CV-1 (African Green Monkey Kidney Cells) (ATTC) cells at 70 percent confluency in T175 flasks transiently transfected with the expression plasmieds (pCMX-VP16-VDR (0.5 µg), pCMX-GAL4-SRC-1 (4.9 µg), GAL4$_{UAS}$-Tk-Luciferase (4.9 µg) and pCMX-b-galactosidase (2.7 µg)), using the transfection reagent FuGENE6 (Roche) following recommended protocols and instructions provided by the manufacturer.

Assay plates were prepared by dispensing approximately 0.5 µl of each compound into a well of a 384 well plate to achieve a final compound concentration of approximately 10 µM after addition of cells. Following incubation with transfection reagents for 5 hours at 37° C., transfected cells were trypsinized, centrifuged, resuspended in media and added to the assay plates, (45 µl, 5000 cells per well). The assay plates containing both compounds and screening cells were incubated for approximately 20 hours at 37° C. in a tissue culture incubator.

After incubation of the transfected cells with compounds, media was aspirated and lysis buffer (1% Triton X 100, 10% Glycerol, 5 mM Dithiothreitol,1 mM EGTA, 25 mM Tricine pH 7.8) added. Luciferase activity was measured in the presence of luciferase assay buffer (0.73 mM ATP, 22.3 mM Tricine, 0.11 mM EGTA, 0.55 mM Luciferin, 0.15 mM Coenzyme A, 0.5 mM HEPES, 10 mM magnesium sulfate) using a standard luminometer (PE Biosystems Northstar reader, or equivalent) following recommended operating instructions and conditions. Luciferase values were normalized with β-galactosidase values using the pCMX-GAL4 expression vector, to normalize for transfection efficiency as described previously (Willey et al., *Gene & Development*, 9:1033-1045 (1995)).

No reporter-driven luciferase activity was observed without VDR cotransfection, indicating the VDR-dependency of the compounds. Ligand concentration yielding 50% induction of luciferase activity (EC$_{50}$) of 1,25(OH)$_2$D$_3$ was about 2-10 nM for 1,25(OH)$_2$ D$_3$, whereas EC$_{50}$ for most of the compounds of the invention range from about 10 µM-10 nM.

The following exemplary compounds exhibited agonist activity with EC$_{50}$ of less than 10µM and efficacy at 50 to 100%:

3-(2-Methyl-4-{2,2,2-trifluoro-1-[4-(2-hydroxy-3,3-dimethyl-butoxy)-3-methyl-phenyl]-1-phenyl-ethyl}-phenoxy)-propane-1,2-diol;

3-(2-Methyl-4-{2,2,3,3,3-pentafluoro-1-[4-(2-hydroxy-3,3-dimethyl-butoxy)-3-methyl-phenyl]-1-phenyl-propyl}-phenoxy)-propane-1,2-diol;

1-(4-{1-Acetyl-4-[4-(3,3-dimethyl-2-oxo-butoxy)-3-methyl-phenyl]-piperidin-4-yl}-2-methyl-phenoxy)-3,3-dimethyl-butan-2-one;

3-(4-{1-ethyl-1-[4-(3-hydroxy-3-methylbutyl)-3-methylphenyl]-propyl}-2-methylphenoxy)-propane 1,2(S)-diol;

3-(4-{1-Ethyl-1-[4-(3-hydroxy-4,4-dimethylpentyl)-phenyl]-propyl}-2-methylphenoxy)-propane-1,2(S)-diol;

(Z)-3-(4-{1-ethyl-1-[4-(3-hydroxy-4,4-dimethylpent-1-enyl)-3-methylphenyl]-propyl}-2-methylphenoxy)-propane-1,2(S)-diol;

3-(4-{1-ethyl-1-[4-(3-ethyl-3-hydroxypentyl)-3-methylphenyl]-propyl}-2-methyl-phenoxy)-propane-1,2(S)-diol; and 3-(4-{1-ethyl-1-[4-(3-hydroxy-4,4-dimethylpentyl)-phenyl]-propyl}-2-methylphenoxy)-propane-1,2(S)-diol.

EXAMPLE 8

In Vivo Gene Regulation and Calcium Potential

A (three day) effective dose study was conducted on normal BALB/c mice in order to select a compound for the athymic nude mice study described below. Two-week old male Balb/c mice (Harlan) were weighed and sorted into groups of six according to Day-1 weight. Animals were given a standard diet and housed under normal lighting conditions. Compounds were administered in sesame oil vehicle with 4% ethanol. Ethanol was removed by evaporation by sparging with nitrogen prior to dosing orally by gavage via a 1 cc syringe with a 20 G disposable feeding needle (0.1 mL dose volume). Dosing was daily for three days, with animal weights measured on Days 0, 1 and 3. On the final day of dosing, six hours after the final dose, animals were euthanized and the kidneys collected and sampled for kidney Two week old male athymic nude mice (Charles River, Colo.) were given a standard diet and housed under normal lighting conditions. Compounds were administered in sesame oil vehicle with no more than 4% ethanol. Ethanol was removed by evaporation by sparging with nitrogen prior to dosing orally by gavage via a 1 cc syringe with a 20 G disposable feeding needle (0.1 mL dose volume). Dosing was every other for 14 days (6 animals/dosing group). Animal weights were monitored on Day 3, 7, 10 and 14. On the final day of dosing, 4-6 h after the final dose, animals were euthanized. The kidneys were collected and sampled for 24-hydroxylase gene expression and blood was collected for calcium determination.

For the PCR assay, kidneys were homogenized in guanidine containing buffer and total RNA was isolated from an entire kidney using TRIzol reagent (Invitrogen, CA) and further purified using an RNeasy column (Qiagen) according to the respective manufacturer's protocols. RNA was amplified via reverse transcription using Superscript II RT (Invitrogen, CA)(5 units/5 ul reaction) and the mouse Cyp24 reverse primer (GGGTAGCGTGTATTCACCCA) (SEQ ID NO: 3). RT reactions were performed in triplicate in a 384-well plate using 400 nM of reverse primer, 500 μM dNTPs and the reagent buffers supplied with Superscript II RT. The RT reactions were performed in a DNA Engine thermal cycler (PTC-200, MJ Research) (50° C. 30 minutes; 72° C. 5 minutes)

Real-Time Quantitative PCR was performed in a 384 well assay plate using the Prism 7900HT (ABI) using the entire product from the reverse transcription reaction above (5 uL). Reactions were performed with the reverse and forward primers (CCCAAGTGTGCCATTCACA) (SEQ ID NO: 4) at 400 nM and with the probe (CTCGGACCCTTGACAAGC-CAACC) (SEQ ID NO: 5) at a concentration of 100 nM. Reactions were performed using Native Taq DNA Polymerase (Invitrogen) at a concentration of 0.5 units/20 μL reaction, 200 μM dNTPs and the buffer supplied by Invitrogen. PCR was performed with an initial incubation for one minute at: 95° C. followed by 40 cycles of 95° C.-12 seconds, 60° C. in 60 seconds. A six point standard curve was run in parallel with calibration points from $1.6 \times 10^7$ to $1.6 \times 10^2$ copies ssDNA. Results were analyzed using the data analysis and software packet (SDS) provided with the instrumentation.

Calcium determination was carried out in a micronized plate format with heparinized plasma samples utilizing a colorimetric assay (Sigma 588-3). In this assay, plasma samples (2 μL) prepared from the blood were reacted with a test reagent containing an Arsenazo II dye. When present in an acidic medium, the calcium Arsenazo complex forms a purple color that was determined using a standard plate reader at 600 nM against a standard curve.

Figure 2:
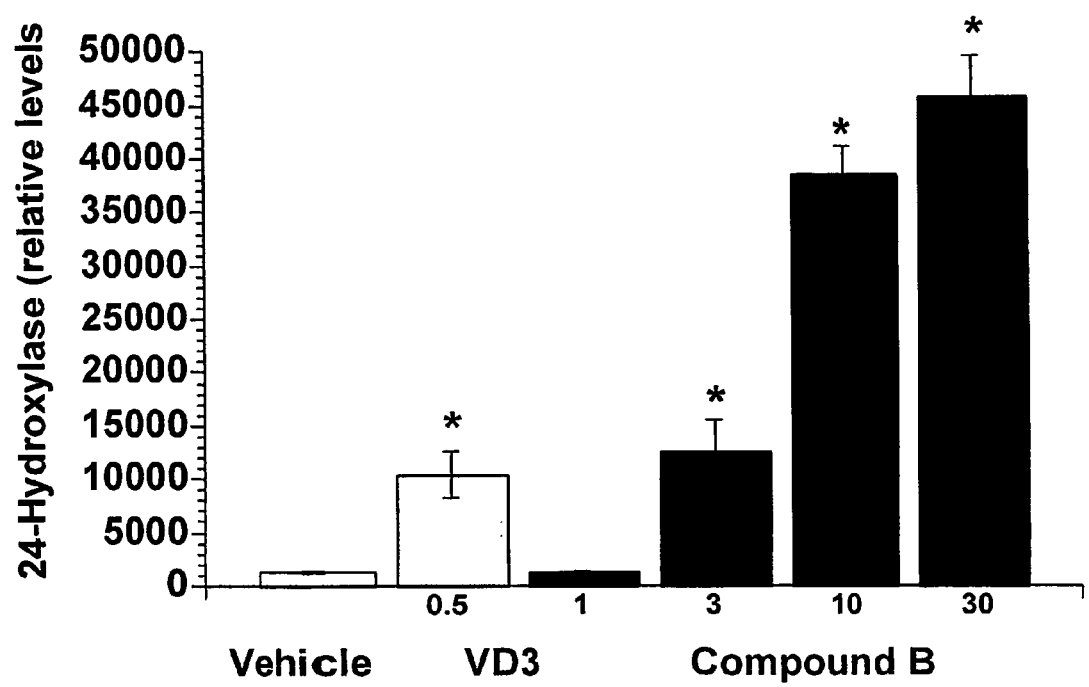
FIG. 2 shows the levels of kidney 24-hydroxylase expression (values normalized relative to cyclophilin) in mice administered one selected compound of the current invention, Compound B, at four different doses (μg/kg) administered every other day for fourteen days.

Results are summarized in FIGS. 1 and 2. FIG. 1 compares the effect of 1α,25-dihydroxyvitamin $D_3$, against four different doses of one selected compound of the current invention, Compound B on plasma calcium levels in athymic nude mice at Day 14 measured 3 hours after final dose. Dosage is measured in μg/kg and plasma calcium levels are in mg/dl. (Asterisks (*) signify P<0.05 compared to vehicle control, student's t-test). FIG. 2 compares the effect of 1α,25-dihydroxyvitamin $D_3$ against four different doses of compound B on kidney 24-hydroxylase gene expression relative to cyclophilin expression (Asterisks (*) signify P<0.05 compared to vehicle control, student's t-test).

The results in FIGS. 1 and 2 show that compound B can induce a dose responsive increase in RNA expression of 24-hydroxylase, a known VDR target gene (FIG. 2), without elevating plasma calcium concentration. (FIG. 1).

EXAMPLE 9

Microarray Analysis

Oligonucleotide microarray experiments may be performed on 10 μg total RNA and analyzed according to protocols developed by Affymetrix (Santa Clarita, Calif.). Briefly, after quality determination on test arrays, the samples from bone, intestine, and kidney are hybridized for 16 h at 45° C. to Affymetrix Mouse Genome arrays (430 set) while tumor RNA will be hybridized to Affymetrix Human Genome arrays (HG-U133 set). The arrays will be washed and then stained with streptavidin-phycoerythrin (genome arrays will be amplified with an anti-streptavidin Ab). The arrays will be scanned with the GeneArray scanner (Agilent Technologies, Palo Alto, Calif.). Raw data will be collected and analyzed by using Affymetrix MICROARRAY SUITE and DATA MINING TOOLS software. Experiments may be done in two replicates from two sample pools. Only genes with 100% concordance in the comparison will be considered significantly different (P<0.05).

Once a set of genes has been identified that is reflective of the ratio of desired (i.e. anti-proliferation or bone formation), to undesired (hypercalcemia) compound activity, in vitro assays such as promoter based co-transfection experiments, can be developed. These assays may be predictive of the in vivo result and can therefore be used as a rational basis for rapidly driving further chemical optimization and identification of improved compounds that have a greater separation of anti-tumor effects from hypercalcemic effects.

The skilled practitioner will understand that many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of the filing of this application.

What is claimed is:

1. A compound having the formula (I):

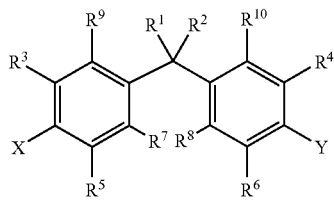

(I)

wherein:

$R^1$ and $R^2$ are each independently halo, haloalkyl, cyanido, cyanato, thiocyanato, selenocyananto, trifluoromethoxy, azido, optionally substituted alkyl, optionally substituted alkenyl, optionally substituted alkynyl, optionally substituted cycloalkyl, optionally substituted heterocyclyl, or optionally substituted heteroaryl; or $R^1$ and $R^2$, together with the carbon atom to which they are attached, form an optionally substituted heterocyclyl selected from a group consisting of:

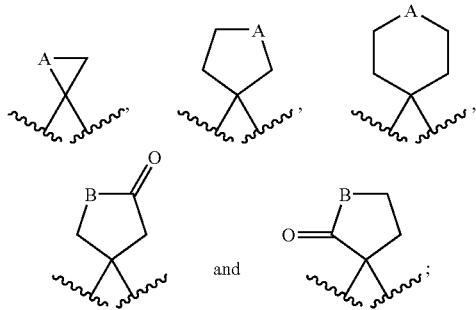

wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$—C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl; and wherein each p is independently 0 to 2;

$R^3$ and $R^4$ are each independently alkyl, alkenyl, cycloalkyl, heterocyclyl, aryl, halo, cyanido, cyanato, thiocyanato, selenocyanato, trifluoromethoxy, azido, haloalkyl, nitro, cyano, azido, —R$^{14}$—R$^{15}$, —R$^{14}$—N(R$^{18}$)R$^{19}$, —R$^{14}$—SR$^{15}$, —R$^{14}$—OC(J)R$^{15}$, —R$^{14}$—NR$^{17}$C(J)R$^{15}$, —R$^{14}$—OC(J)N(R$^{18}$)R$^{19}$, —R$^{14}$—NR$^{17}$C(J)N(R$^{18}$)R$^{19}$, —R$^{14}$—NR$^{17}$C(J)OR$^{15}$, —R$^{14}$—C(J)R$^{15}$, —R$^{14}$—C(J)OR$^{15}$, —R$^{14}$—C(J)SR$^{16}$, —R$^{14}$—C(J)N(R$^{18}$)R$^{19}$ or —R$^{14}$C(J)N(R$^{17}$)N(R$^{18}$)R$^{19}$;

$R^5$, $R^6$, $R^7$, $R^8$, $R^9$, $R^{10}$ are each independently hydrogen, amino, cyanido, cyanato, thiocyanato, selenocyanato, trifluoromethoxy, azido, cyano, nitro, alkyl, haloalkyl, alkoxy or haloalkoxy;

X is $R^{25}$;

Y is independently $R^{30}$, —OR$^{31}$, —SR$^{32}$ or —N(R$^{33}$)(R$^{34}$);

$R^{25}$ and $R^{30}$ are each independently selected from (i) or (ii) as follows:

(i) optionally substituted alkyl that may be substituted with one to ten substituents each independently selected from a group consisting of halo, cyanido, cyanato, thiocyanato, selenocyanato, trifluoromethoxy, azido, nitro, cyano, thioxo, azido, amidino, guanidino, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$ and —C(=NR$^{17}$)N(R$^{18}$)R$^{19}$; or (ii) optionally substituted alkenyl or optionally substituted alkynyl, either of which may be substituted with one to ten substituents each independently selected from a group consisting of oxo, thioxo, halo, cyanido, cyanato, thiocyanato, selenocyanato, trifluoromethoxy, azido, nitro, cyano, azido, amidino, guanidino, —$OR^{15}$, —$OR^{16}OR^{15}$, —$N(R^{18})R^{19}$, —$N(R^{17})N(R^{18})R^{19}$, —$SR^{15}$, —$SR^{16}SR^{15}$, —$S(O)_pR^{20}$, —$N(R^{17})S(O)_pR^{20}$, -$N(R^{17})N(R^{17})S(O)_pR^{20}$, —$OC(J)R^{15}$, —$NR^{17}C(J)R^{15}$, —$OC(J)N(R^{18})R^{19}$, —$NR^{17}C(J)N(R^{18})R^{19}$, —$NR^{17}C(J)OR^{15}$, —$OC(J)OR^{15}$, —$P(R^{21})_2$, —$P(O)(R^{21})_2$, —$OP(O)(R^{21})_2$, —$C(J)R^{15}$, —$C(J)OR^{15}$, —$C(J)SR^{16}$, —$C(J)N(R^{18})R^{19}$, —$C(J)N(R^{17})N(R^{18})R^{19}$, —$C(J)N(R^{17})S(O)_pR^{20}$, —$C(J)N(R^{17})N(R^{17})S(O)_pR^{20}$, —$C(R^{17})=NOR^{15}$, —$C(R^{17})=NR^{17}$, —$C(R^{17})=NN(R^{18})R^{19}$, —$C(=NR^{17})N(R^{18})R^{19}$, alkyl, haloalkyl, cycloalkyl, heterocyclyl, aryl and heteroaryl;

$R^{31}$, $R^{32}$, $R^{33}$ and $R^{34}$ are each independently optionally substituted alkyl, optionally substituted alkenyl, optionally substituted alkynyl or optionally substituted cycloalkyl; all of which, when substituted, are substituted with one to ten substituents each independently selected from a group consisting of oxo, halo, cyanido, cyanato, thiocyanato, selenocyanato, trifluoromethoxy, azido, nitro, cyano, azido, amidino, guanidino, —$OR^{15}$, —$OR^{16}OR^{15}$, —$N(R^{18})R^{19}$, —$N(R^{17})N(R^{18})R^{19}$, —$SR^{15}$, —$SR^{16}SR^{15}$, —$S(O)_pR^{20}$, —$N(R^{17})S(O)_pR^{20}$, —$N(R^{17})N(R^{17})S(O)_pR^{20}$, —$OC(J)R^{15}$, —$NR^{17}C(J)R^{15}$, —$OC(J)N(R^{18})R^{19}$, —$NR^{17}C(J)N(R^{18})R^{19}$, —$NR^{17}C(J)OR^{15}$, —$OC(J)OR^{15}$, —$P(R^{21})_2$, —$P(O)(R^{21})_2$, —$OP(O)R^{21})_2$, —$C(J)R^{15}$, —$C(J)OR^{15}$, —$C(J)SR^{16}$, —$C(J)N(R^{18})R^{19}$, —$C(J)N(R^{17})N(R^{18})R^{19}$, —$C(J)N(R^{17})S(O)_pR^{20}$, —$C(J)N(R^{17})N(R^{17})S(O)_pR^{20}$, —$C(R^{17})=NOR^{15}$, —$C(R^{17})=NR^{17}$, —$C(R^{17})=NN(R^{18})R^{19}$, —$C(=NR^{17})N(R^{18})R^{19}$, alkyl, cycloalkyl, heterocyclyl, aryl and heteroaryl, and $R^{34}$ can additionally be hydrogen;

where each $R^{14}$ is independently a direct bond or alkylene;

where each $R^{15}$ and $R^{17}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, cyano, hydroxy and amino;

where each $R^{16}$ and $R^{20}$ is independently optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino; and where each $R^{18}$ and $R^{19}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino;

or where $R^{18}$ and $R^{19}$, together with the nitrogen atom to which they are attached, form a heterocyclyl or heteroaryl;

each $R^{21}$ is independently alkyl, —$OR^{22}$ or —$N(R^{23})R^{24}$;

$R^{22}$ is hydrogen, alkyl, haloalkyl, alkenyl, alkynyl, cycloalkyl, heterocyclyl, aryl, heteroaryl or aralkyl;

$R^{23}$ and $R^{24}$ are each independently hydrogen, alkyl, haloalkyl, alkenyl, alkynyl or cycloalkyl;

or $R^{23}$ and $R^{24}$, together with the nitrogen atom to which they are attached, form a heterocyclyl or heteroaryl;

each J is independently O or S;

as a single isomer, a mixture of isomers, or as a racemic mixture of isomers; as a solvate or polymorph; or as a prodrug or metabolite; or as a pharmaceutically acceptable salt thereof;

provided that when $R^1$ and $R^2$ form a substituted cyclohexyl, said cyclohexyl, when substituted at the 4-position relative to the gem-diaryl substituents, is substituted with a substituent selected from the group consisting of halo, cyano, optionally substituted alkyl, optionally substituted alkenyl, optionally substituted alkynyl, optionally substituted aryl and optionally substituted heteroaryl; and provided that neither $R^{25}$ nor $R^{30}$ is:
—$CH_2COOH$;
—$CH_2$-5-tetrazolyl;
—$CH_2COOMe$;
—$CH_2COOEt$;
—$CH_2NH(CH_2COOH)$;
—$CH_2N(C(O)Me)(CH_2COOH)$;
—$CH_2$—N-pyrrolidin-2-one;
—$CH_2$-(1-methylpyrrolidin-2-one-3-yl);
—$CH_2COOH$;
—$CH_2C(O)NH_2$;
—$CH_2C(O)NMe_2$;
—$CH_2C(O)NHMe$;
—$CH_2C(O)$—N-pyrrolidine;
—$CH(OH)COOH$;
—$CH(OH)C(O)NH_2$;
—$CH(OH)C(O)NHMe$;
—$CH(OH)C(O)NMe_2$;
—$CH(OH)C(O)NEt_2$;
—$CH_2CH_2COOH$;
—$CH_2CH_2COOMe$;
—$CH_2CH_2COOEt$;
—$CH_2CH_2COOMe$;
—$CH_2CH_2COOEt$;
—$CH_2CH_2C(O)NH_2$;
—$CH_2CH_2C(O)NHMe$;
—$CH_2CH_2C(O)NMe_2$; or
—$CH_2CH_2$-5-tetrazolyl.

2. The compound of claim 1 wherein:

$R^1$ and $R^2$ are each independently halo, haloalkyl, cyanido, cyanato, thiocyanato, selenocyanato, trifluoromethoxy, azido, optionally substituted alkyl, optionally substituted alkenyl, optionally substituted alkynyl, optionally substituted cycloalkyl, optionally substituted heterocyclyl, or optionally substituted heteroaryl; or $R^1$ and $R^2$, together with the carbon atom to which they are attached, form an optionally substituted heterocyclyl selected from a group consisting of:

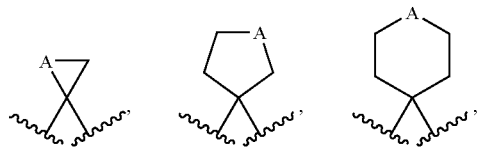

-continued

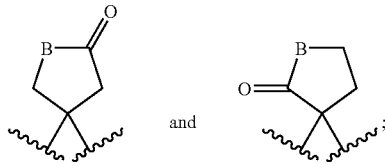

and wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$—C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl; and wherein each p is independently 0 to 2;

R$^{25}$ and R$^{30}$ are each independently selected from (i), (ii) or (iii) as follows:

(i) optionally substituted alkyl that may be substituted with one to ten substituents each independently selected from a group consisting of halo, cyanido, cyanato, thiocyanato, selenocyanato, trifluoromethoxy, azido, nitro, cyano, thioxo, azido, amidino, guanidino, optionally substituted cycloalkyl, optionally substituted heterocyclyl, optionally substituted aryl, optionally substituted heteroaryl, optionally substituted heteroaralkyl, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)SR$^{16}$, —C(J)N(R$^{17}$)N(R$^{18}$)R$^{19}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$ and —C(=NR$^{17}$)N(R$^{18}$)R$^{19}$;

(ii) substituted propyl, substituted butyl or substituted pentyl, wherein said optionally substituted propyl, said optionally substituted butyl or said optionally substituted pentyl can additionally be substituted with substituents selected from the group consisting of —C(J)OR$^{15}$, —C(J)N(R$^{18}$)R$^{19}$ and optionally substituted heteroaryl; or (iii) optionally substituted alkenyl or optionally substituted alkynyl, either of which may be substituted with one to ten substituents each independently selected from a group consisting of oxo, thioxo, halo, cyanido, cyanato, thiocyanato, selenocyanato, trifluoromethoxy, azido, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N($^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$, —C(=NR$^{17}$)N(R$^{18}$)R$^{19}$, alkyl, haloalkyl, cycloalkyl, heterocyclyl, aryl and heteroaryl;

R$^{31}$, R$^{32}$, R$^{33}$ and R$^{34}$ are each independently optionally substituted alkyl, optionally substituted alkenyl, optionally substituted alkynyl or optionally substituted cycloalkyl; all of which, when substituted, are substituted with one to ten substituents each independently selected from a group consisting of oxo, halo, cyanido, cyanato, thiocyanato, selenocyanato, trifluoromethoxy, azido, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$, —C(=NR$^{17}$)N(R$^{18}$)R$^{19}$, alkyl, cycloalkyl, heterocyclyl, aryl and heteroaryl, and R$^{34}$ can additionally be hydrogen;

where R$^{15}$, R$^{16}$, R$^{17}$, R$^{18}$, R$^{19}$, R$^{20}$ and R$^{21}$ are as described in claim 1.

3. The compound of claim 2 wherein R$^{25}$, R$^{30}$, R$^{31}$, R$^{32}$, R$^{33}$ and R$^{34}$ are Each independently optionally substituted alkyl selected from group a) or group b), optionally substituted alkenyl selected from group c) or group d) or optionally substituted alkynyl selected from group e) or group f);

wherein R$^{31}$, R$^{32}$, R$^{33}$ and R$^{34}$ can additionally be optionally substituted cycloalkyl selected from group g);

and wherein R$^{34}$ can additionally be hydrogen;

wherein group (a) consists of:

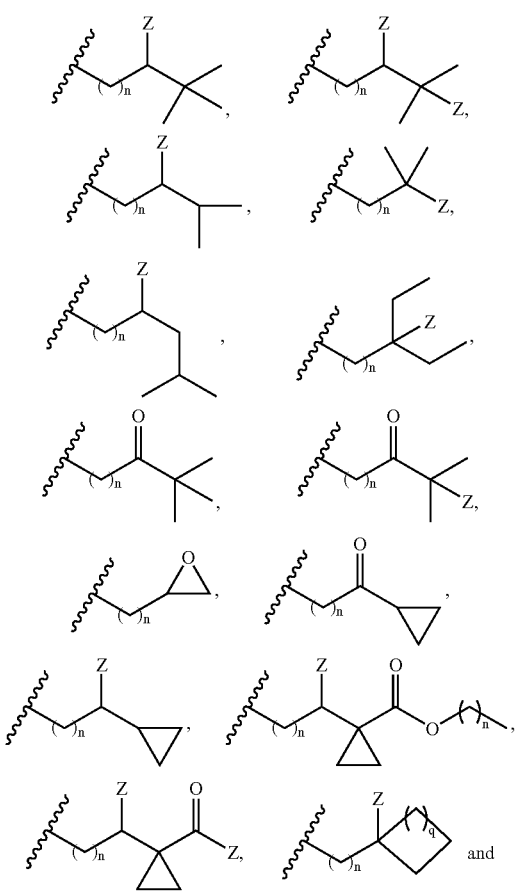

-continued
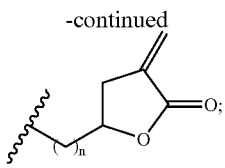
wherein group (b) consists of:
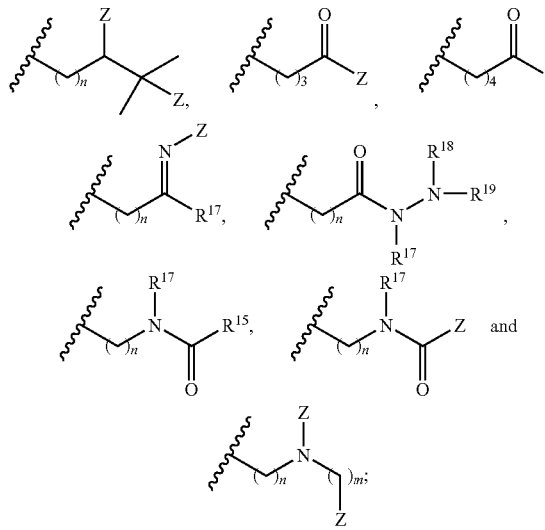
wherein group (c) consists of both cis and trans conformations of:
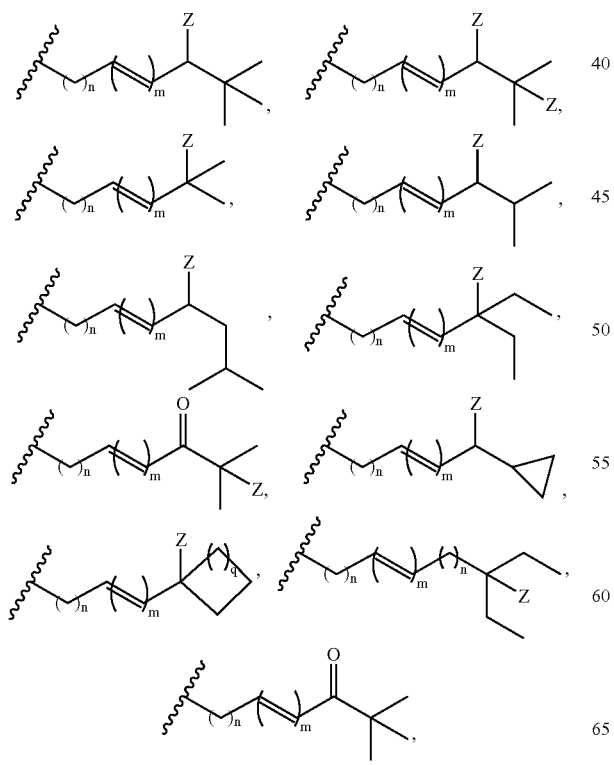
-continued
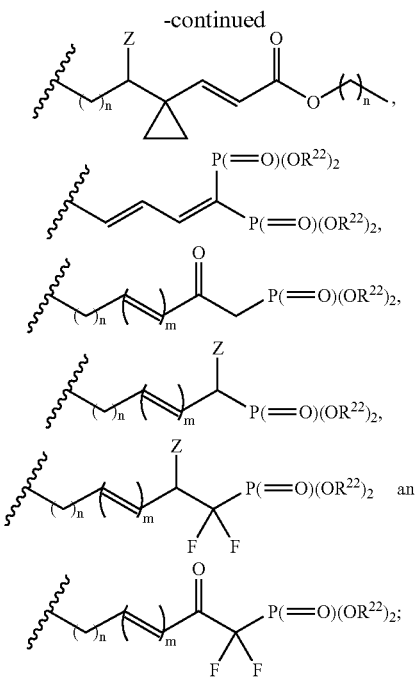
and group (d) consists of both cis and trans conformations of:
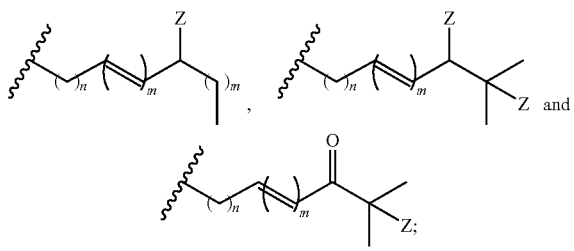
wherein group (e) consists of:
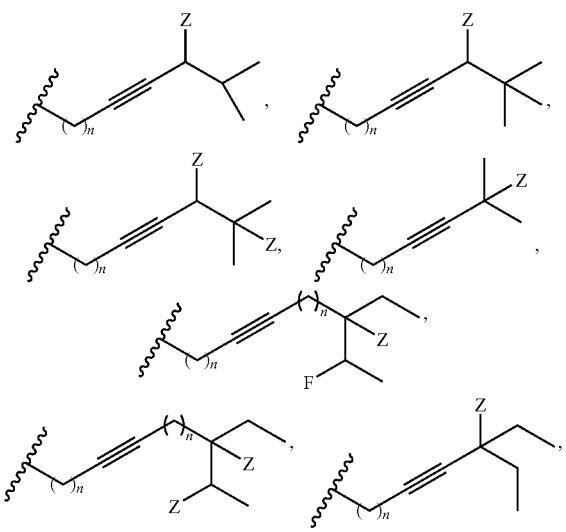

-continued

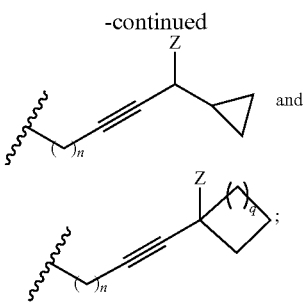

wherein group (f) consists of:

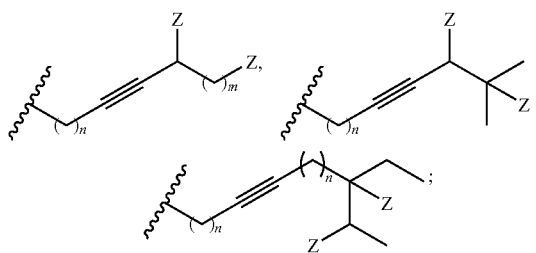

and wherein group (g) consists of:

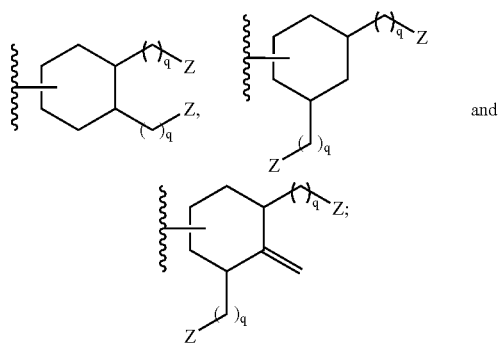

wherein each Z is independently OH, OR, $NH_2$, NHR, N(R)(R) wherein R is each independently alkyl or haloalkyl; each n is independently an integer from 0 to 4; each m is independently an integer from 1 to 2 and each q is independently an integer from 0 to 4;

and wherein any member of groups a), b) c), d), e), f) and g) may optionally be halogenated.

4. The compound of claim 3 wherein:
X is $R^{25}$;
Y is —$SR^{32}$ or —$N(R^{33})(R^{34})$;
$R^1$ and $R^2$ are each independently alkyl or haloalkyl;
$R^3$ and $R^4$ are each independently , halo, cyanido, cyanato, thiocyanato, selenocyanato, trifluoromethoxy, azido, alkyl or haloalkyl;
$R^5$, $R^6$, $R^7$, $R^8$, $R^9$, $R^{10}$ are hydrogen; and
$R^{25}$, $R^{32}$, $R^{33}$ and $R^{34}$ are as described in claim 3.

5. The compound of claim 3 wherein:
X is $R^{25}$;
Y is —$OR^{31}$;
$R^1$ and $R^2$ are each independently alkyl or haloalkyl;
$R^3$ and $R^4$ are each independently halo, cyanido, cyanato, thiocyanato, selenocyanato, trifluoromethoxy, azido, alkyl or haloalkyl;
$R^5$, $R^6$, $R^7$, $R^8$, $R^9$, $R^{10}$ are hydrogen; and
$R^{25}$ and $R^{31}$ are as described in claim 3.

6. The compound of claim 5 wherein $R^{25}$ is optionally substituted alkyl Selected from group (a) and $R^{31}$ is optionally substituted alkyl selected from group (b).

7. The compound of claim 6 wherein $R^3$ and $R^4$ are each independently halo, alkyl or haloalkyl.

8. The compound of claim 7 wherein the compounds are selected from a group consisting of:
   3-(4-{1-ethyl-1-[4-(3-hydroxy-3-methylbutyl)-3-methylphenyl]-propyl}-2-methylphenoxy)-propane-1,2(S)-diol;
   3-(4-{1-ethyl-1-[4-(3-ethyl-3-hydroxypentyl)-3-methylphenyl]-propyl}-2-methyl-phenoxy)-propane-1,2(S)-diol;
   3-(4-{1-ethyl-1-[4-(3-hydroxy-5-methylhexyl)-3-methylphenyl]-propyl}-2-methyl-phenoxy)-propane-1,2(S)-diol;
   3-(4-{1-ethyl-1-[4-(3-hydroxy-4-methylpentyl)-3-methylphenyl]-propyl}-2-methyl-phenoxy)-propane-1,2(S)-diol;
   3-(2-ethyl-4-{1-ethyl-1-[4-(3-hydroxy-4,4-dimethylpentyl)-3-methylphenyl]-propyl}-phenoxy)-propane-1,2(S)-diol;
   3-(4-{1-ethyl-1-[4-(3-hydroxy-4,4-dimethylpentyl)-3-methylphenyl]-propyl}-2-methyl-phenoxy)-propane-1,2(S)-diol;
   3-[4-(1-ethyl-1-{4-[3(S)-hydroxy-4,4-dimethylpentyl]-3-methylphenyl}-propyl) 2-methyl-phenoxy]-propane-1,2(S)-diol; and
   3-[4-(1-ethyl-1-{4-[3(R)-hydroxy-4,4-dimethylpentyl]-3-methylphenyl}-propyl) 2-methyl-phenoxy]-propane-1,2(S)-diol.

9. The compound of claim 6 wherein $R^3$ is halo and $R^4$ is alkyl, halo or haloalkyl.

10. The compound of claim 6 wherein $R^3$ is alkyl, halo or haloalkyl and $R^4$ is halo.

11. The compound of claim 5 wherein $R^{25}$ is optionally substituted alkenyl selected from group (c) or group (d) and $R^{31}$ is optionally substituted alkyl selected from group (a) or group (b).

12. The compound of claim 11 wherein $R^3$ and $R^4$ are each independently alkyl or haloalkyl.

13. The compound of claim 12, selected from the group consisting of:
   (Z)-3-(4-{1-ethyl-1-[4-(3-hydroxy-4,4-dimethylpent-1-enyl) -3-methylphenyl]-propyl}-2-methylphenoxy)-propane-1,2(S)-diol;
   (E)-3-(4-{1-ethyl-1-[4-(3-hydroxy-4,4-dimethylpent-1-enyl)-3-methylphenyl]-propyl}-2-methylphenoxy)-propane-1,2(S)-diol; and
   (E)-3-(4-{1-ethyl-1-[4-(3-ethyl-3-hydroxypent-1-enyl)-3-methylphenyl]-propyl}-2-methylphenoxy)-propane-1,2(S)-diol.

14. The compound of claim 11 wherein $R^3$ is alkyl or haloalkyl and $R^4$ is halo.

15. The compound of claim 5 wherein $R^{25}$ is optionally substituted alkynyl selected from group (e) or group (f) and $R^{31}$ is optionally substituted alkyl selected from group (a) or group (b).

16. The compound of claim 15 wherein $R^3$ and $R^4$ are each independently alkyl or haloalkyl.

17. The compound of claim 16 selected from the group consisting of
- 3-(4-{1-ethyl-1-[4-(3-hydroxy-4,4-dimethylpent-1-ynyl)-3-methylphenyl]-propyl}-2-methylphenoxy)-propane-1,2(S)-diol;
- 3-(4-{1-ethyl-1-[4-(3(R)-hydroxy-4,4-dimethylpent-1-ynyl)-3-methylphenyl]-propyl}-2-methylphenoxy)-propane-1,2(S)-diol;
- 3-(4-{1-ethyl-1-[4-(3(S)-hydroxy-4,4-dimethylpent-1-ynyl)-3-methylphenyl]-propyl}-2-methylphenoxy)-propane-1,2(S)-diol; and
- 3-(4-{1-ethyl-1-[4-(3-ethyl-3-hydroxypent-1-ynyl)-3-methyl-phenyl]-propyl}-2-methylphenoxy)-propane-1,2 (S)-diol.

18. The compound of claim 1 wherein:
X is $R^{25}$;
Y is $R^{30}$; and
$R^{25}$ and $R^{30}$ are as described in claim 1.

19. The compound of claim 18 wherein:
$R^1$ and $R^2$ are each independently optionally substituted alkyl or haloalkyl;
$R^3$ and $R^4$ are each independently halo, cyanido, cyanato, thiocyanato, selenocyanato, trifluoromethoxy, azido, alkyl or haloalkyl;
$R^5$, $R^6$, $R^7$, $R^8$, $R^9$, $R^{10}$ are hydrogen;
$R^{25}$ and $R^{30}$ are each independently substituted alkyl selected from group a) or group b), substituted alkenyl selected from group c) or group d) or substituted alkynyl selected from group e) or group f);
wherein group (a) consists of:

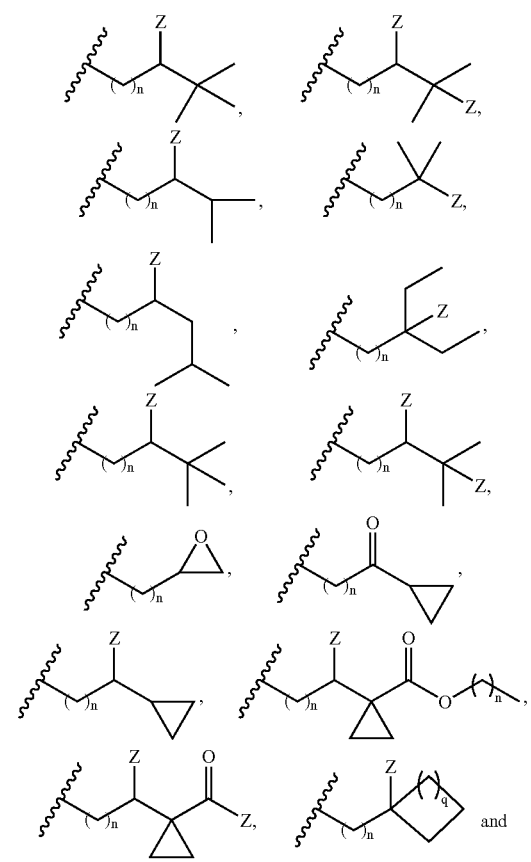

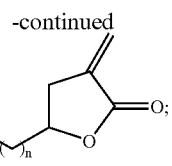

wherein group (b) consists of:

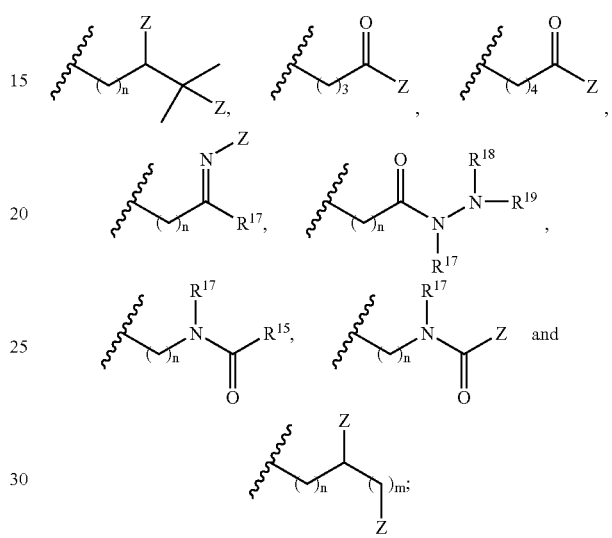

wherein group (c) consists of both cis and trans conformations of:

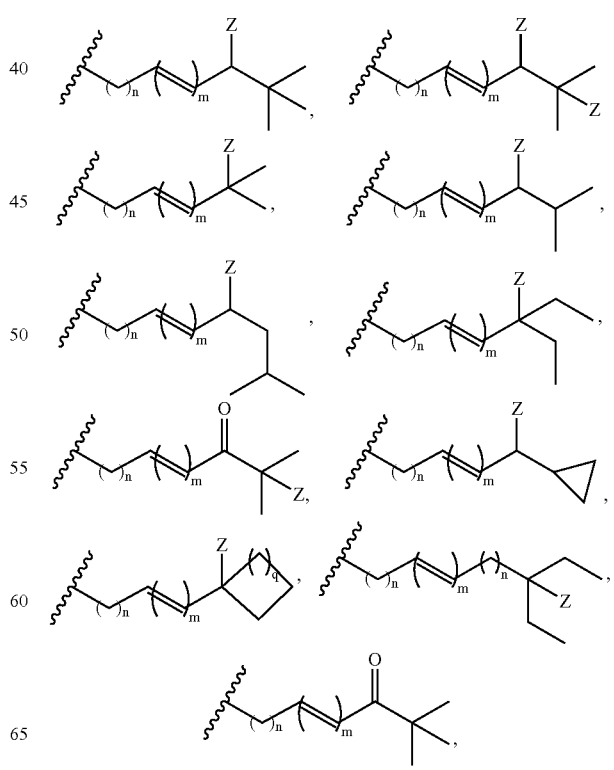

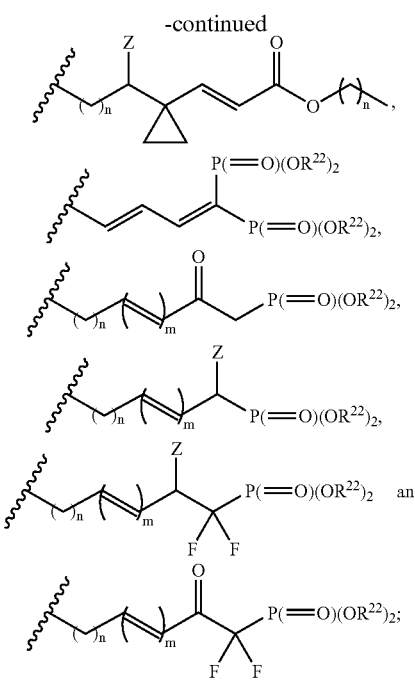

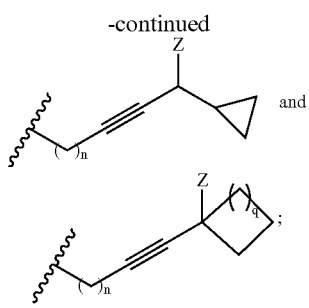

wherein group (f) consists of:

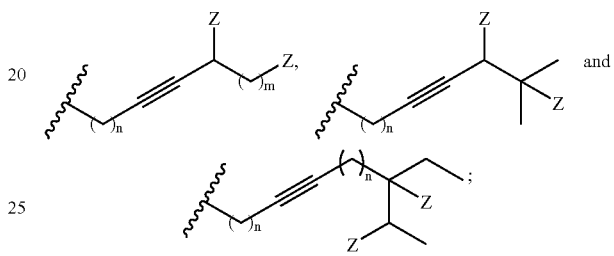

wherein group (d) consists of both cis and trans conformations of:

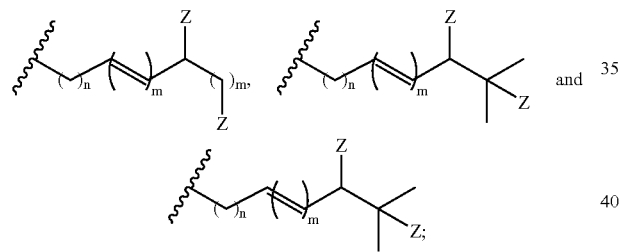

wherein group (e) consists of:

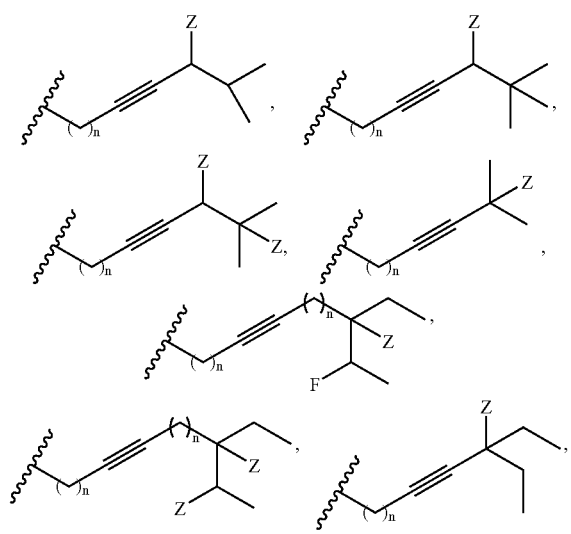

wherein each Z is independently OH, OR, $NH_2$, NHR, N(R)(R) wherein R is independently alkyl or haloalkyl; each n is independently an integer from 0 to 4; each m is independently an integer from 1 to 2 and each q is independently an integer from 0 to 4;

and wherein any member of groups a), b) c), d), e), f) and g) may optionally be halogenated.

20. The compound of claim 19 wherein $R^{25}$ is optionally substituted alkyl selected from group a), optionally substituted alkenyl selected from group c) or optionally substituted alkynyl selected from group e) and $R^{30}$ is optionally substituted alkyl selected from group b).

21. The compound of claim 20 wherein $R^3$ and $R^4$ are each independently alkyl or haloalkyl.

22. The compound of claim 20 wherein $R^3$ is alkyl or haloalkyl and $R^4$ is hydrogen.

23. The compound of claim 1 wherein

X is $R^{25}$;

Y is —$OR^{31}$;

$R^1$ and $R^2$ are ethyl;

$R^3$ and $R^4$ are methyl;

$R^{25}$ is selected from the group consisting of:

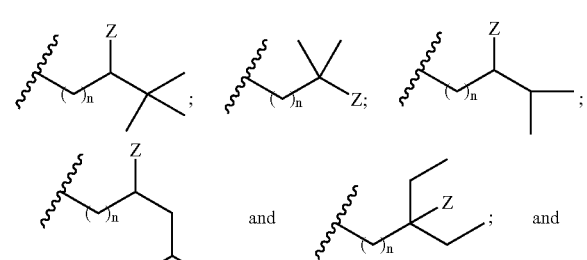

$R^{31}$ is selected from the group consisting of:

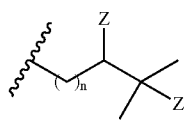 and 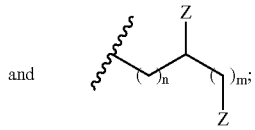

wherein each Z is independently OH, OR, $NH_2$, NHR, N(R)(R) wherein R is independently alkyl or haloalkyl; each n is independently an integer from 0 to 4 and each m is independently an integer from 1 to 2.

24. The compound of claim 1 wherein:
X is $R^{25}$;
Y is —$OR^{31}$;
$R^1$ and $R^2$ are ethyl;
$R^3$ and $R^4$ are methyl;
$R^{25}$ is selected from the group consisting of both cis and trans conformations of:

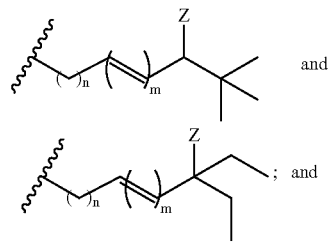

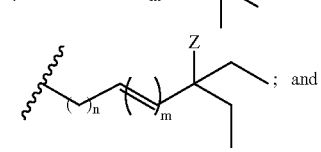

$R^{31}$ is selected from the group consisting of both cis and trans conformations of:

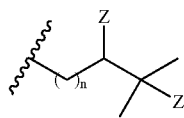 and 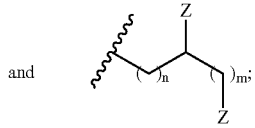

wherein each Z is independently OH, OR, $NH_2$, NHR, N(R)(R) wherein R is independently alkyl or haloalkyl; each n is independently an integer from 0 to 4 and each m is independently an integer from 1 to 2.

25. The compound of claim 1 wherein:
X is $R^{25}$;
Y is —$OR^{31}$;
$R^1$ and $R^2$ are ethyl;
$R^3$ and $R^4$ are methyl;
$R^{25}$ is selected from the group consisting of:

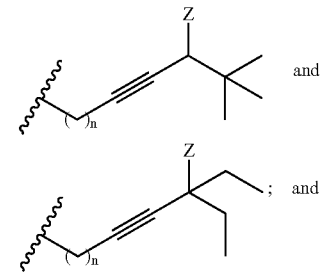

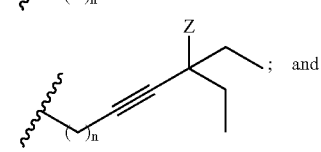

$R^{31}$ is selected from the group consisting of:

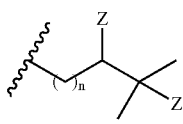 and 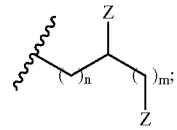

wherein each Z is independently OH, OR, $NH_2$, NHR, N(R)(R) wherein R is independently alkyl or haloalkyl; each n is independently an integer from 0 to 4 and each m is independently an integer from 1 to 2.

26. A pharmaceutical composition comprising a compound of claim 1 and one or more additional ingredient selected from the group consisting of an anticancer agent, an anti-autoimmune agent, a parathyroid hormone, a calcium supplement, an anti-arthritic compound, an anti-inflammatory compound, a matrix metalloproteinase inhibitor, an inhibitor of pro-inflammatory cytokines, an NSAID, a corticosteroid, a COX-1 inhibitor, a COX-2 inhibitor, acetaminophen and ibuprofen.

27. A method of supplementing treatment of a disease or disorder selected from the group consisting of hyperparathyroidism, renal failure, osteomalacia, intestinal malabsorption syndrome, osteoporosis, Alzheimers disease, hyperproliferative skin diseases, psoriasis, pruritis, acne and seborrheic dermatitis, comprising administering to a subject in need thereof an effective amount of a compound of claim 1.

28. A method of supplementing treatment of breast cancer colon cancer, prostate cancer, ovarian cancer, brain glial tumors, squamous cell carcinoma, ovarian cancer, myeloid leukemia, osteosarcoma; myelofibrosis and melanoma, comprising administering to a subject in need thereof an effective amount of a compound of claim 1.

29. The method of claim 28 wherein said method further comprises administering one additional active ingredient selected from a group comprising 5-fluoro-uracil, methotrexate, fludarabine, antimicrotubule agents, vincristine, vinblastine, taxanes, paclitaxel, docetaxel, alkylating agent, cyclophasphamide, melphalan, biochoroethylnitrosurea, hydroxyurea, platinum agents, cisplatin, carboplatin, oxaliplatin, JM-216, Cl-973, anthracyclines, doxrubicin, daunorubicin, antibiotics, mitomycin, idarubicin, adriamycin, daunomycin), topoisomerase inhibitiors, etoposide, camptothecins, or any other cytotoxic agents, estramustine phosphate, prednimustine, steroids, anti-steroids, estrogens, anti-estrogens, androgens, anti-androgens, glucocorticoids and dexamethasone.

30. The method of claim 29 wherein said method further comprises the administration in conjunction with chemotherapy or radiation therapy of a compound of formula (I)

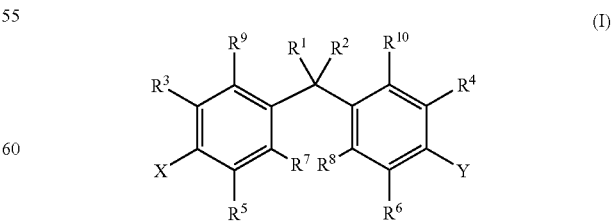

(I)

wherein:
$R^1$ and $R^2$ are each independently halo, haloalkyl, cyanido, cyanato, thiocyanato, selenocyanato, trifluoromethoxy, azido, optionally substituted alkyl, optionally substituted alkenyl, optionally substituted alkynyl, optionally substituted cycloalkyl, optionally substituted heterocyclyl, or optionally substituted heteroaryl; or $R^1$ and $R^2$, together with the carbon atom to which they are attached, form an optionally substituted heterocyclyl selected from a group consisting of:

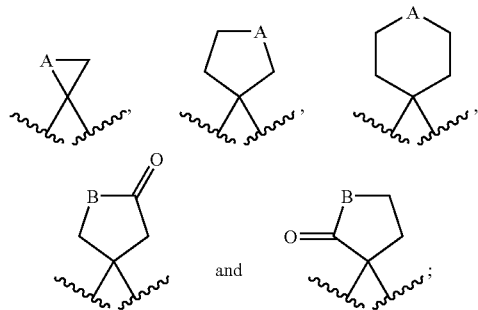

wherein A is —O—, —NR$^x$—, —S—, —S(O)— or —S(O)$_2$— wherein R$^x$ is hydrogen, alkyl, haloalkyl, cycloalkyl, heterocyclyl, aryl, heteroaryl, —R$^{14}$—C(J)R$^{15}$, —R$^{14}$—C(J)OR$^{15}$, —R$^{14}$—C(J)R$^{16}$OR$^{15}$, —R$^{14}$—C(J)SR$^{16}$, —R$^{14}$—C(J)N(R$^{18}$)R$^{19}$, —R$^{14}$—C(J)N(R$^{17}$)N(R$^{18}$)R$^{19}$, —R$^{14}$—C(J)N(R$^{17}$)S(O)$_p$R$^{20}$, —R$^{14}$—S(O)$_p$N(R$^{18}$)R$^{19}$ or —R$^{14}$—S(O)$_p$R$^{20}$; and wherein B is —O—, —S— or —NR$^y$— wherein R$^y$ is hydrogen, alkyl, haloalkyl, aryl or heteroaryl: and wherein each p is independently 0 to 2;

$R^3$ and $R^4$ are each independently alkyl, alkenyl, alkynyl, cycloalkyl, heterocyclyl, aryl, heteroaryl, halo, cyanido, cyanato, thiocyanato, selenocyanato, trifluoromethoxy, azido, haloalkyl, nitro, cyano, azido, —R$^{14}$-R$^{15}$, —R$^{14}$—N(R$^{18}$)R$^{19}$, —R$^{14}$—SR$^{15}$, —R$^{14}$—OC(J)R$^{15}$, —R$^{14}$—NR$^{17}$C(J)R$^{15}$, —R$^{14}$—OC(J)N(R$^{18}$)R$^{19}$, —R$^{14}$—NR$^{17}$C(J)N(R$^{18}$)R$^{19}$, —R$^{14}$—NR$^{17}$C(J)OR$^{15}$, —R$^{14}$—C(J)R$^{15}$, —R$^{14}$—C(J)OR$^{15}$, —R$^{14}$—C(J)SR$^{16}$, —R$^{14}$—C(J)N(R$^{18}$)R$^{19}$ or —R$^{14}$C(J)N(R$^{17}$)N(R$^{18}$)R$^{19}$;

$R^5, R^6, R^7, R^8, R^9, R^{10}$ are each independently hydrogen, amino, cyanido, cyanato, thiocyanato, selenocyanato, trifluoromethoxy, azido, cyano, nitro, alkyl, haloalkyl, alkoxy or haloalkoxy;

X is $R^{25}$;

Y is independently $R^{30}$, —OR$^{31}$, —SR$^{32}$ or —N(R$^{33}$)(R$^{34}$);

$R^{25}$ and $R^{30}$ are each independently selected from (i) or (ii) as follows:

(i) optionally substituted alkyl that may be substituted with one to ten substituents each independently selected from a group consisting of halo, cyanido, cyanato, thiocyanato, selenocyanato, trifluoromethoxy, azido, nitro, cyano, thioxo, azido, amidino, guanidino, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{15}$, —OR$^{16}$OR$^{15}$, —N(R$^{18}$OR$^{19}$, —N(R$^{17}$)N(R$^{18}$)R$^{19}$, —SR$^{15}$, —SR$^{16}$SR$^{15}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)N(R$^{18}$)R$^{19}$, —C(J)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$ and —C(=NR$^{17}$)N(R$^{18}$)R$^{19}$; or (ii) optionally substituted alkenyl or optionally substituted alkynyl, either of which may be substituted with one to ten substituents each independently selected from a group consisting of oxo, thioxo, halo, cyanido, cyanato, thiocyanato, selenocyanato, trifluoromethoxy, azido, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$, —C(=NR$^{17}$)N(R$^{18}$)R$^{19}$, alkyl, haloalkyl, cycloalkyl, heterocyclyl, aryl and heteroaryl;

$R^{31}, R^{32}, R^{33}$ and $R^{34}$ are each independently optionally substituted alkyl, optionally substituted alkenyl, optionally substituted alkynyl or optionally substituted cycloalkyl: all of which, when substituted, are substituted with one to ten substituents each independently selected from a group consisting of oxo, halo, cyanido, cyanato, thiocyanato, selenocyanato, trifluoromethoxy, azido, nitro, cyano, azido, amidino, guanidino, —OR$^{15}$, —OR$^{16}$OR$^{15}$, —N(R$^{18}$)R$^{19}$, —N(R$^{17}$)N(R$^{18}$)R$^{19}$, —SR$^{15}$, —SR$^{16}$SR$^{15}$, —S(O)$_p$R$^{20}$, —N(R$^{17}$)S(O)$_p$R$^{20}$, —N(R$^{17}$)N(R$^{17}$)S(O)$_p$R$^{20}$, —OC(J)R$^{15}$, —NR$^{17}$C(J)R$^{15}$, —OC(J)N(R$^{18}$)R$^{19}$, —NR$^{17}$C(J)N(R$^{18}$)R$^{19}$, —NR$^{17}$C(J)OR$^{15}$, —OC(J)OR$^{15}$, —P(R$^{21}$)$_2$, —P(O)(R$^{21}$)$_2$, —OP(O)(R$^{21}$)$_2$, —C(J)R$^{15}$, —C(J)OR$^{15}$, —C(J)SR$^{16}$, —C(J)N(R$^{18}$)R$^{19}$, —C(J)N(R$^{17}$)N(R$^{18}$)R$^{19}$, —C(J)N(R$^{17}$)S(O)$_p$R$^{20}$, —C(J)N(R$^{17}$)N(R$^{17}$)S(O)$_p$R$^{20}$, —C(R$^{17}$)=NOR$^{15}$, —C(R$^{17}$)=NR$^{17}$, —C(R$^{17}$)=NN(R$^{18}$)R$^{19}$, —C(=NR$^{17}$)N(R$^{18}$)R$^{19}$, alkyl, cycloalkyl, heterocyclyl, aryl and heteroaryl, and $R^{34}$ can additionally be hydrogen:

where each $R^{14}$ is independently a direct bond or alkylene;

where each $R^{15}$ and $R^{17}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, cyano, hydroxy and amino;

where each $R^{16}$ and $R^{20}$ is independently optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino; and where each $R^{18}$ and $R^{19}$ is independently hydrogen, optionally substituted alkyl, optionally substituted alkenyl, optionally substituted alkynyl, optionally substituted cycloalkyl, optionally substituted heterocyclyl, optionally substituted aryl or optionally substituted heteroaryl, all of which, when substituted, are substituted with one to five substituents each independently selected from halo, hydroxy, alkoxy and amino;

or where $R^{18}$ and $R^{19}$, together with the nitrogen atom to which they are attached, form a heterocyclyl or heteroaryl;

each $R^{21}$ is independently alkyl, —$OR^{22}$ or —$N(R^{23})R^{24}$;

$R^{22}$ is hydrogen, alkyl, haloalkyl, alkenyl, alkynyl, cycloalkyl, heterocyclyl, aryl, heteroaryl or aralkyl;

$R^{23}$ and $R^{24}$ are each independently hydrogen, alkyl, haloalkyl, alkenyl, alkynyl or cycloalkyl;

or $R^{23}$ and $R^{24}$, together with the nitrogen atom to which they are attached, form a heterocyclyl or heteroaryl;

each J is independently O or S:

as a single isomer, a mixture of isomers, or as a racemic mixture of isomers; as a solvate or polymorph; or as a prodrug or metabolite: or as a pharmaceutically acceptable salt thereof;

provided that when $R^1$ and $R^2$ form a substituted cyclohexyl, said cyclohexyl, when substituted at the 4-position relative to the gem-diaryl substituents, is substituted with a substituent selected from the group consisting of halo, cyano, optionally substituted alkyl, optionally substituted alkenyl, optionally substituted alkynyl, optionally substituted aryl and optionally substituted heteroaryl; and provided that neither $R^{25}$ nor $R^{30}$ is:

—$CH_2COOH$;
—$CH_2$-5-tetrazolyl;
—$CH_2COOMe$;
—$CH_2COOEt$;
—$CH_2NH(CH_2COOH)$;
—$CH_2N(C(O)Me)(CH_2COOH)$;
—$CH_2$-N-pyrrolidin-2-one;
—$CH_2$-(1-methylpyrrolidin-2-one-3-yl);
—$CH_2COOH$;
—$CH_2C(O)NH_2$;
—$CH_2C(O)NMe_2$;
—$CH_2C(O)NHMe$;
—$CH_2C(O)$—N-pyrrolidine;
—$CH(OH)COOH$;
—$CH(OH)C(O)NH_2$;
—$CH(OH)C(O)NHMe$;
—$CH(OH)C(O)NMe_2$;
—$CH(OH)C(O)NEt_2$;
—$CH_2CH_2COOH$;
—$CH_2CH_2COOMe$;
—$CH_2CH_2COOEt$;
—$CH_2CH_2COOMe$;
—$CH_2CH_2COOEt$;
—$CH_2CH_2C(O)NH_2$;
—$CH_2CH_2C(O)NHMe$;
—$CH_2CH_2C(O)NMe_2$; or
—$CH_2CH_2$-5-tetrazolyl.

31. A compound which is:
3-(4-{1-ethyl-1-[4-(3-hydroxy-4,4-dimethylpentyl)-phenyl]-propyl}-2-methylphenoxy)-propane-1,2(S)-diol; or
3-(4-{1-ethyl-1-[4-(3-hydroxy-4,4-dimethyl-pentyl)-3-methyl-phenyl]-propyl}-phenoxy)-propane-1,2(S)-diol.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Artificial
<220> FEATURE:
<223> OTHER INFORMATION: Receptor interacting domain of a co-activator peptide
<220> FEATURE:
<221> NAME/KEY: MISC_FEATURE
<222> LOCATION: (2)..(3)
<223> OTHER INFORMATION: Xaa = any amino acid

<400> SEQUENCE: 1

Leu Xaa Xaa Leu Leu
1               5

<210> SEQ ID NO 2
<211> LENGTH: 17
<212> TYPE: DNA
<213> ORGANISM: Artificial
<220> FEATURE:
<223> OTHER INFORMATION: GAL4 UAS sequence
<220> FEATURE:
<221> NAME/KEY: misc_feature
<222> LOCATION: (4)..(4)
<223> OTHER INFORMATION: n = A or G
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (7)..(7)
<223> OTHER INFORMATION: n = A or G
<220> FEATURE:
<221> NAME/KEY: misc_feature
<222> LOCATION: (9)..(9)
<223> OTHER INFORMATION: n = C or T
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n = C or T
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 2
cggnnnncnn nncnccg                                              17

<210> SEQ ID NO 3
<211> LENGTH: 20
<212> TYPE: DNA
<213> ORGANISM: Artificial
<220> FEATURE:
<223> OTHER INFORMATION: mouse Cyp24 reverse primer

<400> SEQUENCE: 3
gggtagcgtg tattcaccca                                           20

```
<210> SEQ ID NO 4
<211> LENGTH: 19
<212> TYPE: DNA
<213> ORGANISM: Artificial
<220> FEATURE:
<223> OTHER INFORMATION: PCR primer

<400> SEQUENCE: 4
cccaagtgtg ccattcaca                                              19

<210> SEQ ID NO 5
<211> LENGTH: 23
<212> TYPE: DNA
<213> ORGANISM: Artificial
<220> FEATURE:
<223> OTHER INFORMATION: PCR probe

<400> SEQUENCE: 5
ctcggaccct tgacaagcca acc                                         23
```